US008165819B2

(12) United States Patent
Clermont et al.

(10) Patent No.: US 8,165,819 B2
(45) Date of Patent: Apr. 24, 2012

(54) MODELING WOUND HEALING

(75) Inventors: Gilles Clermont, Fombell, PA (US);
Patricia A. Hebda, Sarver, PA (US); Yee Key Li, Pittsburgh, PA (US); Qi Mi, Pittsburgh, PA (US); David L. Steed, Pittsburgh, PA (US); Joshua Thomas Sullivan, Butler, PA (US); Katherine Verdolini Abbott, Cheswick, PA (US); Yoram Vodovotz, Sewickley, PA (US); Ivan Petrov Yotov, Pittsburgh, PA (US); Gary An, Chicago, IL (US)

(73) Assignee: The University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 1117 days.

(21) Appl. No.: 11/869,852

(22) Filed: Oct. 10, 2007

(65) Prior Publication Data
US 2008/0228456 A1 Sep. 18, 2008

Related U.S. Application Data

(60) Provisional application No. 60/850,690, filed on Oct. 10, 2006, provisional application No. 60/850,896, filed on Oct. 11, 2006.

(51) Int. Cl.
| G06F 19/10 | (2011.01) |
| G01N 33/50 | (2006.01) |
| G06G 7/58 | (2006.01) |
| A61K 38/00 | (2006.01) |
| A61K 38/18 | (2006.01) |
| A61P 17/02 | (2006.01) |

(52) U.S. Cl. .............. 702/19; 703/11; 514/1.4; 514/7.6; 514/9.4

(58) Field of Classification Search .................. None
See application file for complete search history.

(56) References Cited

U.S. PATENT DOCUMENTS
2003/0087285 A1 5/2003 Chow et al.

OTHER PUBLICATIONS

Raud et al. (Agents and Actions (1989) vol. 26, pp. 42-44).*
Adelmann-Grill BC, Hein R, Wach F, Krieg T. Inhibition of fibroblast chemotaxis by recombinant human interferon gamma and interferon alpha. J Cell Physiol. Feb. 1987;130(2):270-5.
Agrawal RP, Agrawal S, Beniwal S, Joshi CP, Kochar DK. Granulocyte-macrophage colony-stimulating factor in foot ulcers. Diabetic Foot 2003;6:93.
Albertson S, Hummel RP 3rd, Breeden M, Greenhalgh DG. PDGF and FGF reverse the healing impairment in protein-malnourished diabetic mice. Surgery. Aug. 1993;114(2):368-72.
American Soc of Plastic Surgeons. Everyday wounds . . . Accessed Aug 9, 2006. http://www.plasticsurgery.org/medical_professionals/publications/Everyday-Wounds-Ch02-How-do-Wounds-Heal.cfm.
An G. Agent-based computer simulation and sirs: building a bridge between basic science and clinical trials. Shock. Oct. 2001;16(4):266-73.
An G. In silico experiments of existing and hypothetical cytokine-directed clinical trials using agent-based modeling. Crit Care Med. Oct. 2004;32(10):2050-60.
An G. Mathematical modeling in medicine: a means, not an end. Crit Care Med. Jan. 2005;33(1):253-4.
Annes JP, Munger JS, Rifkin DB. Making sense of latent TGFbeta activation. J Cell Sci. Jan. 15, 2003;116(Pt 2):217-24.
Atri SC, Misra J, Bisht D, Misra K. Use of homologous platelet factors in achieving total healing of recalcitrant skin ulcers. Surgery. Sep. 1990;108(3):508-12.
Barcellos-Hoff MH, Derynck R, Tsang ML, Weatherbee JA. Transforming growth factor-beta activation in irradiated murine mammary gland. J Clin Invest. Feb. 1994;93(2):892-9.
Barcellos-Hoff MH, Dix TA. Redox-mediated activation of latent transforming growth factor-beta 1. Mol Endocrinol. Sep. 1996;10(9):1077-83.
Baugh JA, Bucala R. Mechanisms for modulating TNF alpha in immune and inflammatory disease. Curr Opin Drug Discov Devel. Sep. 2001;4(5):635-50.
Bayat A, et al. Genetic susceptibility to keloid disease and hypertrophic scarring: transforming growth factor beta1 common polymorphisms and plasma levels. Plast Reconstr Surg. Feb. 2003;111(2):535-43.
Bennett SP, Griffiths GD, Schor AM, Leese GP, Schor SL. Growth factors in the treatment of diabetic foot ulcers. Br J Surg. Feb. 2003;90(2):133-46.
Bitar MS, Labbad ZN. Transforming growth factor-beta and insulin-like growth factor-I in relation to diabetes-induced impairment of wound healing. J Surg Res. Feb. 15, 1996;61(1):113-9.
Bogdan C, Vodovotz Y, Nathan C. Macrophage deactivation by interleukin 10. J Exp Med. Dec. 1, 1991;174(6):1549-55.
Bonabeau E. Agent-based modeling: methods and techniques for simulating human systems. Proc Natl Acad Sci U S A. May 14, 2002;99 Suppl 3:7280-7.
Border WA, Noble NA. Transforming growth factor beta in tissue fibrosis. N Engl J Med. Nov. 10, 1994;331(19):1286-92.
Bostman OM, Pihlajamaki HK. Adverse tissue reactions to bioabsorbable fixation devices. Clin Orthop Relat Res. Feb. 2000;(371):216-27.
Boulton AJ, Meneses P, Ennis WJ. Diabetic foot ulcers: A framework for prevention and care. Wound Repair Regen. Jan.-Feb. 1999;7(1):7-16.
Boyko EJ, Ahroni JH, Smith DG, Davignon D. Increased mortality associated with diabetic foot ulcer. Diabet Med. Nov. 1996;13(11):967-72.

(Continued)

Primary Examiner — Lori A Clow
(74) Attorney, Agent, or Firm — The Webb Law Firm

(57) ABSTRACT

Provided are methods of simulating tissue healing. The methods comprise using a mechanistic computer model of the interrelated effects of inflammation, tissue damage or dysfunction and tissue healing to predict an outcome of healing of damaged tissue in vivo, thereby predicting the outcome of healing of damaged tissue in vivo. Implementations of these methods on a computing device also are provided. Non-limiting examples of diseases and/or conditions that are amenable to simulation according to the methods described herein include: a diabetes, diabetic foot ulcers, necrotizing enterocolitis, ulcerative colitis, Crohn's disease, inflammatory bowel disease, restenosis (post-angioplasty or stent implantation), incisional wounding, excisional wounding, surgery, accidental trauma, pressure ulcer, stasis ulcer, tendon rupture, vocal fold phonotrauma, otitis media and pancreatitis.

70 Claims, 38 Drawing Sheets

OTHER PUBLICATIONS

Branski RC, Rosen CA, Verdolini K, Hebda PA. Acute vocal fold wound healing in a rabbit model. Ann Otol Rhinol Laryngol. Jan. 2005;114(1 Pt 1):19-24.
Branski RC, Rosen CA, Verdolini K, Hebda PA. Biochemical markers associated with acute vocal fold wound healing: a rabbit model. J Voice. Jun. 2005;19(2):283-9.
Branski RC, Rosen CA, Verdolini K, Hebda PA. Markers of wound healing in vocal fold secretions from patients with laryngeal pathology. Ann Otol Rhinol Laryngol. Jan. 2004;113(1):23-9.
Branski RC, Verdolini K, Sandulache V, Rosen CA, Hebda PA. Vocal fold wound healing: a review for clinicians. J Voice. Sep. 2006;20(3):432-42. Epub Dec. 1, 2005.
Braun J, Sieper J. Overview of the use of the anti-TNF agent infliximab in chronic inflammatory diseases. Expert Opin Biol Ther. Feb. 2003;3(1):141-68.
Broadley KN, et al. Growth factors bFGF and TGB beta accelerate the rate of wound repair in normal and in diabetic rats. Int J Tissue React. 1988;10(6):345-53.
Broadley KN, et al. The diabetic rat as an impaired wound healing model: stimulatory effects of transforming growth factor-beta and basic fibroblast growth factor. Biotechnol Ther. 1989-1990;1(1):55-68.
Browne AC, Sibbald RG. The diabetic neuropathic ulcer: an overview. Ostomy Wound Manage. Jan. 1999;45(1A Suppl):6S-20S; quiz 21S-22S.
Buchman TG, Cobb JP, Lapedes AS, Kepler TB. Complex systems analysis: a tool for shock research. Shock. Oct. 2001;16(4):248-51.
Calamia KT. Current and future use of anti-TNF agents in the treatment of autoimmune, inflammatory disorders, Adv Exp Med Biol. 2003;528:545-9.
Caplan MS, Kelly A, Hsueh W. Endotoxin and hypoxia-induced intestinal necrosis in rats: the role of platelet activating factor. Pediatr Res. May 1992;31(5):428-34.
Caplan MS, Sun XM, Hseuh W, Hageman JR. Role of platelet activating factor and tumor necrosis factor-alpha in neonatal necrotizing enterocolitis. J Pediatr. Jun. 1990;116(6):960-4.
Caplan MS, Sun XM, Hsueh W. Hypoxia causes ischemic bowel necrosis in rats: the role of platelet-activating factor (PAF-acether). Gastroenterology. Oct. 1990;99(4):979-86.
Carter K. Growth factors: the wound healing therapy of the future. Br J Community Nurs. Sep. 2003;8(9):S15-6, S18-9, S22-3.
Chow CC, et al. The acute inflammatory response in diverse shock states. Shock. Jul. 2005;24(1):74-84.
Clark RAF. Wound Repair. Overview and General Considerations. In: Clark RAF, editor. The Molecular and Cellular Biology of Wound Repair. New York: Plenum Press Inc. 1988 (pp. 3-33).
Clermont G, Bartels J, Kumar R, Constantine G, Vodovotz Y, Chow C. In silico design of clinical trials: a method coming of age. Crit Care Med. Oct. 2004;32(10):2061-70.
Cobbold CA, Sherratt JA. Mathematical modelling of nitric oxide activity in wound healing can explain keloid and hypertrophic scarring. J Theor Biol. May 21, 2000;204(2):257-88.
Cockbill S. Wound: the healing process. Hospital Pharmacist Oct. 2002;9:255-260.
Consensus Development Conference on Diabetic Foot Wound Care. Apr. 7-8, 1999, Boston, Massachusetts. American Diabetes Association J Am Podiatr Med Assoc 1999;89(9):475-83.
Cook J. A mathematical model for dermal wound healing: wound contraction and scar formation. Ph.D. Thesis. University of Washington (Seattle). 1995.
Csete ME, Doyle JC. Reverse engineering of biological complexity. Science. Mar. 1, 2002;295(5560):1664-9.
Dallon JC, Sherratt JA, Maini PK. Modeling the effects of transforming growth factor-beta on extracellular matrix alignment in dermal wound repair. Wound Repair Regen. Jul.-Aug. 2001;9(4):278-86.
Day J, et al. A reduced mathematical model of the acute inflammatory response II. Capturing scenarios of repeated endotoxin administration. J Theor Biol. Sep. 7, 2006;242(1):237-56. Epub Apr. 17, 2006.
de Boissieu D, et al. Effect of BN 50727 on pathological findings and tissue platelet activating factor levels during ileal ischemia in newborn piglets. J Pediatr Surg. Dec. 1996;31(12):1675-9.
de la Torre J, et al. Wound healing, chronic wounds. eMedicine. Last updated on May 26, 2006. Available at: http://www.emedicine.com/plastic/topic477.htm.
de Lalla F, et al. Randomized prospective controlled trial of recombinant granulocyte colony-stimulating factor as adjunctive therapy . . . Antimicrob Agents Chemother. Apr. 2001;45(4):1094-8.
DeLustro F, Dasch J, Keefe J, Ellingsworth L Immune responses to allogeneic and xenogeneic implants of collagen and collagen derivatives. Clin Orthop Relat Res. Nov. 1990;(260):263-79.
DeVore DP. Long-term compatibility of intraocular lens implant materials. J Long Term Eff Med Implants. 1991;1(2):205-16.
D'Haens GR. Infliximab as disease-modifying therapy. Eur J Gastroenterol Hepatol. Mar. 2003;15(3):233-7.
d'Hemecourt PA, Smiell JM, Karim MR. Sodium carboxymethylcellulose aqueous-based gel versus becaplermin gel in patients with non-healing lower extremity ulcers. Wounds 1998;10:69-75.
Diegelmann RF, Evans MC. Wound healing: an overview of acute, fibrotic and delayed healing. Front Biosci. Jan. 1, 2004;9:283-9.
Edelson MB, Bagwell CE, Rozycki HJ. Circulating pro- and counterinflammatory cytokine levels and severity in necrotizing enterocolitis. Pediatrics. Apr. 1999;103(4 Pt 1):766-71.
Ermentrout GB, Edelstein-Keshet L. Cellular automata approaches to biological modeling. J Theor Biol 1993;160(1):97-133.
Fahey TJ 3rd, Sadaty A, Jones WG 2nd, Barber A, Smoller B, Shires GT. Diabetes impairs the late inflammatory response to wound healing. J Surg Res. Apr. 1991;50(4):308-13.
Fast C, Rosegger H. Necrotizing enterocolitis prophylaxis: oral antibiotics and lyophilized enterobacteria vs oral immunoglobulins. Acta Paediatr Suppl. 1994;396:86-90. (See comments).
Flaumenhaft R, Kojima S, Abe M, Rifkin DB. Activation of latent transforming growth factor beta. Adv Pharmacol. 1993;24:51-76.
Food and Drug Administration. Innovation or Stagnation: Challenge and Opportunity on the Critical Path to New Medical Products. Report on Mar. 2004: i-31.
Ford H, Watkins S, Reblock K, Rowe M. The role of inflammatory cytokines and nitric oxide in the pathogenesis of necrotizing enterocolitis. J Pediatr Surg. Feb. 1997;32(2):275-82.
Ford HR, Sorrells DL, Knisely AS. Inflammatory cytokines, nitric oxide, and necrotizing enterocolitis. Semin Pediatr Surg. Aug. 1996;5(3):155-9.
Freeman BD, Natanson C. Anti-inflammatory therapies in sepsis and septic shock. Expert Opin Investig Drugs. Jul. 2000;9(7):1651-63.
Gallucci RM, et al. Impaired cutaneous wound healing in interleukin-6-deficient and immunosuppressed mice FASEB J. Dec. 2000;14(15):2525-31.
Gallucci RM, et al. Interleukin-6 treatment augments cutaneous wound healing in immunosuppressed mice. J Interferon Cytokine Res. Aug. 2001;21(8):603-9.
Gene ID No. 7040: TGFB1 transforming growth factor, beta 1 [Homo sapiens ]. NCBI Database, National Center for Biotechnology Information, NIH (Bethesda, MD, USA), last updated Aug. 14, 2006.
Goldring SR. Inflammatory mediators as essential elements in bone remodeling. Calcif Tissue Int. Aug. 2003;73(2):97-100.
Goodacre CJ, Kan JY, Rungcharassaeng K. Clinical complications of osseointegrated implants. J Prosthet Dent. May 1999;81(5):537-52.
Goodson WH 3rd, Hunt TK. Wound collagen accumulation in obese hyperglycemic mice. Diabetes. Apr. 1986;35(4):491-5.
Gough A, et al. Randomised placebo-controlled trial of granulocyte-colony stimulating factor in diabetic foot infection. Lancet. Sep. 20, 1997;350(9081):855-9.
Granstein RD, et al. The systemic administration of gamma interferon inhibits collagen synthesis and acute inflammation in a murine skin wounding model. J Invest Dermatol. Jul. 1989;93(1):18-27.
Gray S, Titze I. Histologic investigation of hyperphonated canine vocal cords. Ann Otol Rhinol Laryngol Jul.-Aug. 1988;97(4 Pt 1):381-8.
Gray SD, Titze IR, Alipour F, Hammond TH. Biomechanical and histologic observations of vocal fold fibrous proteins. Ann Otol Rhinol Laryngol. Jan. 2000;109(1):77-85.
Gray SD. Basement membrane zone injury in vocal nodules. In: Guaffin J, Hammarberg B. eds. Vocal Fold Physiology. San Diego: Singular Press, 1991: 21-27.

Greenhalgh DG, Sprugel KH, Murray MJ, Ross R. PDGF and FGF stimulate wound healing in the genetically diabetic mouse. Am J Pathol. Jun. 1990;136(6):1235-46.

Grylack L, Scanlon JW. Necrotizing enterocolitis prophylaxis. Acta Paediatr. Jan. 1995;84(1):21.

Guilak F, Fermor B, Keefe FJ, Kraus VB, Olson SA, Pisetsky DS, Setton LA, Weinberg JB. The role of biomechanics and inflammation in cartilage injury and repair. Clin Orthrop Relat Res. Jan. 2004;(423):17-26.

Hamilton JA. Nondisposable materials, chronic inflammation, and adjuvant action. J Leukoc Biol. Jun. 2003;73(6):702-12.

Hampton CR, Verrier ED. Systemic consequences of ventricular assist devices: alterations of coagulation, immune function, inflammation, and the neuroendocrine system. Artif Organs. Nov. 2002;26(11):902-8.

Harris MC, et al. Cytokine elevations in critically ill infants with sepsis and necrotizing enterocolitis. J. Pediatr. Jan. 1994;124(1):105-11. (See comments).

Harris MC, et al. Cytokine elaboration in critically ill infants with bacterial sepsis, necrotizing entercolitis, or sepsis syndrome: correlation with clinical parameters . . . J Pediatr. Oct. 2005;147(4):462-8.

Harris MI, et al. Prevalence of diabetes, impaired fasting glucose, and impaired glucose tolerance . . . Third National Health & Nutrition Examination Survey, 1988-1994. Diabetes Care. Apr. 1998;21(4):518-24.

Harsch IA, et al. Impaired gastric ulcer healing in diabetic rats: role of heat shock protein, growth factors, prostaglandins and proinflammatory cytokines. Eur J Pharmacol. Nov. 28, 2003;481(2-3):249-60.

Hart J. Inflammation. 1: Its role in the healing of acute wounds. J Wound Care. Jun. 2002;11(6):205-9.

Hart J. Inflammation. 2: Its role in the healing of chronic wounds. J Wound Care. Jul. 2002;11(7):245-9.

Heldin CH, Westermark B. Mechanism of action and in vivo role of platelet-derived growth factor. Physiol Rev. Oct. 1999;79(4):1283-316.

Holloway G, et al. A randomized, controlled multicenter, dose response trial of activated platelet supernatant, topical CT-102 in chronic, non-healing, diabetic wounds. Wounds 1993;5:198-206.

Holzer SE, et al. Costs and duration of care for lower extremity ulcers in patients with diabetes. Clin Ther. Jan.-Feb. 1998;20(1):169-81. Erratum in: Clin Ther Mar.-Apr. 1998;20(2):373.

Hussain MJ, et al. Elevated serum levels of macrophage-derived cytokines precede and accompany the onset of IDDM. Diabetologia. Jan. 1996;39(1):60-9.

Jacobson BH, et al. (1997). The voice handicap index (VHI): Development and validation. Am J Speech Lang Pathol. Aug. 1997;6(3):66-70.

Jude EB, Blakytny R, Bulmer J, Boulton AJ, Ferguson MW. Transforming growth factor-beta 1, 2, 3 and receptor type I and II in diabetic foot ulcers. Diabet Med. Jun. 2002;19(6):440-7.

Kamimura D, Ishihara K, Hirano T. IL-6 signal transduction and its physiological roles: the signal orchestration model. Rev Physiol Biochem Pharmacol. 2003;149:1-38. Epub Apr. 5, 2003.

Karas SP, et al. Coronary intimal proliferation after balloon injury and stenting in swine: an animal model of restenosis. J Am Coll Cardiol. Aug. 1992;20(2):467-74.

Kim BS, Nikolovski J, Bonadio J, Mooney DJ. Cyclic mechanical strain regulates the development of engineered smooth muscle tissue. Nat Biotechnol. Oct. 1999;17(10):979-83.

Kitano H. Systems biology: a brief overview. Science. Mar. 1, 2002;295(5560):1662-4.

Klingbeil CK, Cesar LB, Fiddes JC. Basic fibroblast growth factor accelerates tissue repair in models of impaired wound healing. Prog Clin Biol Res. 1991;365:443-58.

Knighton DR, et al. Classification and treatment of chronic nonhealing wounds. Successful treatment with autologous platelet-derived wound healing factors (PDWHF). Ann Surg. Sep. 1986;204(3):322-30.

Koivukangas V, Annala AP, Salmela PI, Oikarinen A. Delayed restoration of epidermal barrier function after suction blister injury in patients with diabetes mellitus. Diabet Med. Jul. 1999;16(7):563-7.

Koli K, Saharinen J, Hyytiainen M, Penttinen C, Keski-Oja J. Latency, activation, and binding proteins of TGF-beta. Microsc Res Tech. Feb. 15, 2001;52(4):354-62.

Krediet TG, et al. Microbiological factors associated with neonatal necrotizing enterocolitis: protective effect of early antibiotic treatment. Acta Paediatr. Oct. 2003;92(10):1180-2.

Krischel V, et al. Biphasic effect of exogenous nitric oxide on proliferation and differentiation in skin derived keratinocytes but not fibroblasts. Invest Dermatol. Aug. 1998;111(2):286-91.

Krishnamoorthy L, Morris HL, Harding KG. Specific growth factors and the healing of chronic wounds. Wound Care. May 2001;10(5):173-8.

Kuhry E, Jeekel J, Bonjer HJ. Effect of laparoscopy on the immune system. Semin Laparosc Surg. Mar. 2004;11(1):37-44.

Kulkarni AB, Thyagarajan T, Letterio JJ. Function of cytokines within the TGF-beta superfamily as determined from transgenic and gene knockout studies in mice. Curr Mol Med. May 2002;2(3):303-27.

Kumar R, Clermont G, Vodovotz Y, Chow CC. The dynamics of acute inflammation. J Theor Biol. Sep. 21, 2004;230(2):145-55.

Lagoa CE, et al. The role of initial trauma in the host's response to injury and hemorrhage: insights from a correlation of mathematical simulations and hepatic transcriptomic analysis. Shock. Dec. 2006;26(6):592-600.

Lauterbach R, et al. Effect of the immunomodulating agent, pentoxifylline, in the treatment of sepsis in prematurely delivered infants: a placebo-controlled, double-blind. . . Crit Care Med. Apr. 1999;27(4):807-14.

Lauterbach R, Zembala M. Pentoxifylline reduces plasma tumour necrosis factor-alpha concentration in premature infants with sepsis. Eur J Pediatr. May 1996;155(5):404-9.

Levin ME. Diabetic foot ulcers: pathogenesis and management. J ET Nurs. Sep.-Oct. 1993;20(5):191-8.

Lin HC, Su BH, Chen AC, Lin TW, Tsai CH, Yeh TF, Oh W. Oral probiotics reduce the incidence and severity of necrotizing enterocolitis in very low birth weight infants. Pediatrics, Jan. 2005;115(1):1-4.

Lin ZQ, Kondo T, Ishida Y, Takayasu T, Mukaida N. Essential involvement of IL-6 in the skin wound-healing process as evidenced by delayed wound healting in IL-6-deficient mice. J Leukoc Biol. Jun. 2003;73(6):713-21.

Luckhart S, et al. Mammalian transforming growth factor beta 1 activated after ingestion by Anopheles stephensi modulates mosquito immunity. Infect Immun. Jun. 2003;71(6):3000-9.

Ma EP, Yiu EM. Voice activity and participation profile: assessing the impact of voice disorders on daily activities. J Speech Lang Hear Res. Jun. 2001;44(3):511-24.

Martin P. Wound healing—aiming for perfect skin regeneration. Science. Apr. 4, 1997;276(5309):75-81.

Masters KS, et al. Effects of nitric oxide releasing poly(vinyl alcohol) hydrogel dressings on dermal wound healing in diabetic mice. Wound Repair Regen. Sep.-Oct. 2002;10(5):286-94.

Matzinger P. The danger model: a renewed sense of self. Science. Apr. 12, 2002;296(5566):301-5.

McCloy MP, Roberts IA, Howarth U, Watts TL, Murray NA. Interleukin-11 levels in healthy and thrombocytopenic neonates. Pediatr Res. Jun. 2002;51(6):756-60.

Miles RH, Paxton TP, Zacheis D, Dries DJ, Gamelli RL. Systemic administration of interferon-gamma impairs wound healing. J Surg Reg. Mar. 1994;56(3):288-94.

Morain WD, Colen LB. Wound healing in diabetes mellitus. Clin Plast Surg. Jul. 1990;17(3):493-501.

Morecroft JA, Spitz L, Hamilton PA, Holmes SJ. Plasma cytokine levels in necrotizing enterocolitis. Acta Paediatr Suppl. 1994;396:18-20.

Morecroft JA, Spitz L, Hamilton PA, Holmes SJ. Plasma interleukin-6 and tumour necrosis factor levels as predictors of disease severity and outcome in necrotizing. . . J Pediatr Surg. Jun. 1994;29(6):798-800.

Morrison M, Rammage L. The Management of Voice Disorders. San Diego: Singular Publishing Group Inc, 1994: vi-xi, 80-109.

Moulin V, Lawny F, Barritault D, Caruelle JP. Platelet releasate treatment improves skin healing in diabetic rats through endogenous growth factor secretion. Cell Mol Biol (Noisy-le-grand). Sep. 1998;44(6):961-71.

Muguruma K, Gray PW, Tjoelker LW, Johnston JM. The central role of PAF in necrotizing enterocolitis development. Adv Exp Med Biol. 1997;407:379-82.

Mulder GD, et al. Enhanced healing of ulcers in patients with diabetes by topical treatment with glycyl-l-histidyl-l-lysine copper. Wound Repair Regen. Oct. 1994:2(4):259-69.

Murray JD, Maini PK, Tranquillo R. Mechanochemical models for generating biological pattern and form in development. Physics Reports Dec. 1988;171(2):59-84.

Murray JD. Mathematical Biology. Heidelberg (Germany): Springer-Verlag, 1989:IX-XIV, 525-609.

Mutlu LK, Woiciechowsky C, Bechmann I. Inflammatory response after neurosurgery. Best Pract Res Clin Anaesthesiol. Sep. 2004;18(3):407-24.

Nadler EP, et al. Expression of inducible nitric oxide synthase and interleukin-12 in experimental necrotizing enterocolitis. J Surg Res. Jul. 2000;92(1):71-7.

Nadler EP, et al. Intestinal cytokine gene expression in infants with acute necrotizing enterocolitis: interleukin-11 mRNA expression inversely correlates with extent of disease. J Pediatr Surg. Aug. 2001;36(8):1122-9.

Naka T, Nishimoto N, Kishimoto T. The paradigm of IL-6: from basic science to medicine. Arthritis Res. 2002;4 Suppl 3:S233-42. Epub May 9, 2002.

Nathan C. Points of control in inflammation. Nature. Dec. 19-26, 2002;420(6917):846-52.

NCBI Accession No. AAC55944. NCBI Database, National Center for Biotechnology Information, NIH (Bethesda, MD, USA), last updated Oct. 24, 1996.

Nian M, Lee P, Khaper N, Liu P. Inflammatory cytokines and postmyocardial infarction remodeling. Circ Res. Jun. 25, 2004;94(12):1543-53.

Nieman G, Bartels J, Wei J, et al. Mathematical simulation of inflammation in porcine septic shock and ARDS. Shock, Jun. 2005;23(Supplement 3):3, Abstract No. 7.

Nose Y, Okubo H. Artificial organs versus regenerative medicine: is it true? Artif Organs. Sep. 2003;27(9):765-71.

O'Connor-McCourt MD, Wakefield LM. Latent transforming growth factor-beta in serum. A specific complex with alpha 2-macroglobulin. J Biol Chem. Oct. 15, 1987;262(29):14090-9.

Ohshima T, Sato Y. Time-dependent expression of interleukin-10 (IL-10) mRNA during the early phase of skin wound healing as a possible indicator of wound vitality. Int J Legal Med. 1998;111(5):251-5.

Olsen L, Sherratt JA, Maini PK. A mechanochemical model for adult dermal wound contraction and the permanence of the contracted tissue displacement profile. J Theor BIol. Nov. 21, 1995;177(2):113-28.

Opal SM, DePalo VA. Anti-inflammatory cytokines. Chest. Apr. 2000;117(4):1162-72.

Parelman AG. Sterile uveitis and intraocular lens implantation. J Am Intraocul Implant Soc. Oct. 1979;5(4):301-6.

Pecoraro RE, Ahroni JH, Boyko EJ, Stensel VL. Chronology and determinants of tissue repair in diabetic lower-extremity ulcers. Diabetes. Oct. 1991;40(10):1305-13.

Peter CS, Feuerhahn M, Bohnhorst B, Schlaud M, Ziesing S, von der Hardt H, Poets CF. Necrotising enterocolities: is there a relationship to specific pathogens? Eur J Pediatr. Jan. 1999;158(1):67-70.

Philip AG. Correction: neutrophil values in neonates with sepsis. J Pediatr. Jul. 1994;125(1):176.

Popovich PG, Jones TB. Manipulating neuroinflammatory reactions in the injured spinal cord: back to basics. Trends Pharmacol Sci. Jan. 2003;24(1):13-7.

Prince JM, et al. In silico and in vivo approach to elucidate the inflammatory complexity of CD14-deficient mice. Mol Med. Apr.-Jun. 2006;12(4-6):88-96.

R&D Systems. Cytokines in wound healing. First printed in 2002 R&D annual catalog. Available at: http://www.rndsystems.com/mini_review_detail_objectname_MR02_CytokineWoundHealing.aspx.

Raaijmakers MF, Dekker J, Dejonckere PH. Diagnostic assessment and treatment goals in logopedics: impairments, disabilities and handicaps. Folia Phoniatr Logop. 1998;50(2):71-9.

Railsback SF. Getting "results": the pattern-oriented approach to analyzing natural systems with individual-based models. Natural Resource Modeling 2001;14(3):465-474.

Ramadori G, Saile B. Inflammation, damage repair, immune cells, and liver fibrosis: specific or nonspecific, this is the question. Gastroenterology. Sep. 2004;127(3):997-1000.

Ramsey SD, Newton K, Blough D, McCulloch DK, Sandhu N, Reiber GE, Wagner EH. Incidence, outcomes, and cost of foot ulcers in patients with diabetes. Diabetes Care. Mar. 1999;22(3):382-7.

Rapala K. The effect of tumor necrosis factor-alpha on wound healing. An experimental study. Ann Chir Gynaecol Suppl. 1996;211:1-53.

Redd MJ, Cooper L, Wood W, Stramer B, Martin P. Wound healing and inflammation: embryos reveal the way to perfect repair. Philos Trans R Soc Lond B Biol Sci. May 29, 2004;359(144):777-84.

Ren Y, et al. Up-regulation of macrophage migration inhibitory factor in infants with acute neonatal necrotizing enterocolitis. Histopathology. Jun. 2005;46(6):659-67.

Reynolds A, et al. A reduced mathematical model of the acute inflammatory response: I. Derivation of model and analysis of anti-inflammation. J Theor Biol. Sep. 7, 2006;242(1):220-36. Epub Apr. 3, 2006.

Reynolds C. Individual-based models. Last updated on Oct. 22, 1999. Available at: http://www.red3d.com/cwr/ibm.html.

Richard JL, et al. Effect of topical basic fibroblast growth factor on the healing of chronic diabetic neuropathic ulcer of the foot. A pilot, randomized, double-blind . . . Diabetes Care. Jan. 1995;18(1):64-9.

Roberts AB, Sporn MB. Transforming growth factor-b. In: Clark RAF, editor. The Molecular and Cellular Biology of Wound Repair. New York: Plenum Press, 1996:275-308.

Robinson, K.A. Pig coronary artery model of post-angioplasty restenosis. In: Waksman R, King SB, Crocker IR, Mould RF, eds. Vascular Brachytherapy. Armonk, NY: Futura Publishing Co,1996:30-40.

Robson MC, Hill DP, Woodske ME, Steed DL. Wound healing trajectories as predictors of effectiveness of therapeutic agents. Arch Surg. Jul. 2000;135(7):773-7.

Robson MC, et al. Integrating the results of Phase IV (postmarketing) clinical trial with four previous trials reinforces the position that Regranex (becaplemin) gel 0.01% is an effective . . . J Appl Res 2005;5(1):35-45.

Robson MC, Steed DL, Franz MG. Wound healing: biologic features and approaches to maximize healing trajectories. Curr Probl Surg. Feb. 2001;38(2):72-140.

Robson MC, Steed DL, McPherson JM, Prett BM. Effects of transforming growth factors b2 on wound healing in diabetic foot ulcers. J Appl Res 2002;2(2):133-45.

Romagnoli C, et al. Plasma levels of interleukin-6 and interleukin-10 in preterm neonates evaluated for sepsis. Eur J Pediatr. Jun. 2001;160(6):345-50.

Sataloff, R. T. Voice rest. In: RT Sataloff, ed., Professional Voice: The Science and Art of Clinical Care (2nd ed.), Singular Publishing Group, San Diego (2nd ed.), 1997: 987-991.

Sato Y, Ohshima T, Kondo T. Regulatory role of endogenous interleukin-10 in cutaneous inflammatory response of murine wound healing. Biochem Biophys Res Commun. Nov. 1999;265(1):194-9.

Schaffer MR, et al. Diabetes-impaired healing and reduced wound nitric oxide synthesis: a possible pathophysiologic correlation. Surgery. May 1997;121(5):513-9.

Schaffer MR, Tantry U, Gross SS, Wasserburg HL, Barbul A. Nitric oxide regulates wound healing. J Surg Res. Jun. 1996;63(1):237-40.

Schwentker A, Vodovotz Y, Weller R, Billiar TR. Nitric oxide and wound repair: role of cytokines? Nitric Oxide. Aug. 2002;7(1):1-10.

Sherratt JA, Dallon JC. Theoretical models of wound healing: past successes and future challenges. C R Biol. May 2002;325(5):557-64.

Sherratt JA, Murray JD. Models of epidermal wound healing. Proc R Soc London Biol. Jul. 23, 1990;241(1300):29-36.

Sido B, Teklote JR, Hartel M, Friess H, Buchler MW. Inflammatory response after abdominal surgery. Best Pract Res Clin Anaesthesiol. Sep. 2004;18(3):439-54.

Smallwood RH, Holcombe WM, Walker DC. Development and validation of computational models of cellular interaction. J Mol Histol. Sep. 2004;35(7):659-65.

Smiell JM, et al. Efficacy and safety of becaplermin (recombinant human platelet-derived growth factor-BB) in patients with nonhealing, lower extremity diabetic . . . Wound Repair Regen. Sep.-Oct. 1999;7(5):335-46.

Smith E, Verdolini K, Gray SD, Nichols S, Lemke, J. Effect of voice disorders on quality of life. Journal of Medical Speech Language Pathology. 1996;4, 223-44.

Steed DL, Donohoe D, Webster MW, Lindsley L. Effect of extensive debridement and treatment on the healing of diabetic foot ulcers. Diabetic Ulcer Study Group. J Am Coll Surg. Jul. 1996;183(1):61-4.

Steed DL, et al. Randomized prospective double-blind trial in healing chronic diabetic foot ulcers. CT-102 activated platelet supernatant, topical versus plabebo. Diabetes Care. Nov. 1992;15(11):1598-604.

Steed DL. Clinical evaluation of recombinant human platelet-derived growth factor for the treatment of lower extremity diabetic ulcers. Diabetic Ulcer Study Group. J Vasc Surg. Jan. 1995;21(1):71-8.

Steed DL. Modifying the wound healing response with exogenous growth factors. Clin Plast Surg. Jul. 1998;25(3):397-405.

Steed DL. Wound-healing trajectories. Surg Clin North Am. Jun. 2003;83(3):547-55, vi-vii.

Stemple JC, Lee L, D'Amico B, Pickup B. Efficacy of vocal function exercises as a method of improving voice production. J Voice. Sep. 1994;8(3):271-8.

Stratakis CA, Mastorakos G, Chrousos GP. Interleukin-6 elevation in critically ill infants with sepsis and necrotizing enterocolitis. J Pediatr. Sep. 1994;125(3):504.

Tang L, Eaton JW. Inflammatory responses to biomaterials. Am J Clin Pathol. Apr. 1995;103(4):466-71.

Thompson LO, Loebe M, Noon GP. What price support? Ventricular assist device induced systemic response. ASAIO J. Sep.-Oct. 2003;49(5):518-26.

Titze IR, et al. Design and validation of a bioreactor for engineering vocal fold tissues under combined tensile and vibrational stresses. J Biomech. Oct. 2004;37(10):1521-9.

Tjardes T, Neugebauer E. Sepsis research in the next millennium: concentrate on the software rather than the hardware. Shock. Jan. 2002;17(1):1-8.

Tranquillo RT, Murray JD. Continuum model of fibroblast-driven wound contraction: inflammation-mediation. J Theor Biol. Sep. 21, 1992;158(2):135-72.

Tranquillo RT, Murray JD. Mechanistic model of wound contraction. J Surg Res. Aug. 1993;55(2):233-47.

Tsang MW, et al. Human epidermal growth factor enhances healing of diabetic foot ulcers. Diabetes Care Jun. 2003;26(6):1856-61.

Upperman JS, et al. Mathematical modeling in necrotizing enterocolitis—a new look at an ongoing problem. J Pediatr Surg. Mar. 2007;42(3):445-53.

Upperman JS, Potoka D, Grishin A, Hackam D, Zamora R, Ford HR. Mechanisms of nitric oxide-mediated intestinal barrier failure in necrotizing enterocolitis. Semin Pediatr Surg. Aug. 2005;14(3):159-66.

Van Dyke Parunak H, et al. Agent-Based Modeling . . . Proc. of Multi-agent Sys & Agent-based Simulation 1st Nat'l Workshop, Paris, France, Jul. 4-6, 1988. Lecture Notes in Comp Sci, vol. 1534, pp. 10-25.

Verdolini K, et al. Shifts in biochemical markers associated with wound healing in laryngeal secretions following phonotrauma: a preliminary study. Ann Otol Rhinol Laryngol. Dec. 2003;112(12):1021-5.

Verdolini, K. (2000). Case Study: Resonant Voice Therapy. In: J. Stemple, ed., Voice therapy: Clinical Studies (2nd ed.) San Diego: Singular Publishing Inc.: 46-62.

Viscardi RM, et al. Inflammatory cytokine mRNAs in surgical specimens of necrotizing enterocolitis and normal newborn intestine. Pediatr Pathol Lab Med. Jul.-Aug. 1997;17(4):547-59.

Vodovotz Y, et al. Regulation of transforming growth factor beta1 by nitric oxide. Cancer Res. May 1, 1999;59(9):2142-9.

Vodovotz Y, Clermont G, Chow C, An G. Mathematical models of the acute inflammatory response. Curr Opin Crit Care. Oct. 2004;10(5):383-90.

Vodovotz Y, Waksman R, Kim WH, Bhargava B, Chan RC, Leon M. Effects of intracoronary radiation on thrombosis after balloon overstretch injury in the porcine model. Circulation. Dec. 1999;100(25):2527-33.

Vodovotz Y. Deciphering the complexity of acute inflammation using mathematical models. Immunol Res. 2006;36(1-3):237-45.

Wahl SM, McCartney-Francis N, Mergenhagen SE. Inflammatory and immunomodulatory roles of TGF-beta. Immunol Today. Aug. 1989;10(8):258-61.

Wahl SM. Transforming growth factor beta: the good, the bad, and the ugly. J Exp Med. Nov. 1, 1994;180(5):1587-90.

Wakefield LM, et al. Recombinant latent transforming growth factor beta 1 has a longer plasma half-life in rats than active transforming growth factor beta 1 . . . J Clin Invest. Dec. 1990;86(6):1976-84.

Waksman R. Late thrombosis after radiation. Sitting on a time bomb. Circulation. Aug. 24, 1999;100(8):780-2.

Walker DC, Hill G, Wood SM, Smallwood RH, Southgate J. Agent-based computational modeling of wounded epithelial cell monolayers. IEEE Trans Nanobioscience. Sep. 2004;3(3):153-63.

Walker DC, et al. The epitheliome: agent-based modelling of the social behaviour of cells. Biosystems. Aug.-Oct. 2004;76(1-3):89-100.

Whitcomb DC, Aoun E, Vodovotz Y, Clermont G, Barmada MM. Evaluating disorders with a complex genetics basis, the future roles of meta-analysis and systems biology. Dig Dis Sci. Dec. 2005;50(12):2195-202.

Wieman TJ, et al. Efficacy and safety of a topical gel formulation of recombinant human platelet-derived growth factor-BB (becaplermin) in patients with chronic . . . Diabetes Care. May 1998;21(5):822-7.

Wilensky, U. (1999). NetLogo® 3.1.2 Users Manual. Center for Connected Learning and ComputerBased Modeling, Northwestern University, Evanston, IL. Available at: http://ccl.northwestern.edu/netlogo/.

Witte MB, Barbul A. General principles of wound healing. Surg Clin North Am. Jun. 1997;77(3):509-28.

Yamasaki K, et al. Reversal of impaired wound repair in iNOS-deficient mice by topical adenoviral-mediated iNOS gene transfer. J Clin Invest. Mar. 1, 1998;101(5):967-71.

Zamora R et al. Plasma cytokine levels in experimental necrotizing . . . Proc of 4th Int'l Conf. on Complexity in Acute Illness. Sep. 29-Oct. 1, 2005. Cologne, Germany, reprinted in J Crit Care. Dec. 2005;20(4):397.

Zamora R, Vodovotz Y. Transforming growth factor-beta in critical illness. Crit Care Med. Dec. 2005;33(12 Suppl):S478-81.

Zimmerman JJ. Appraising the potential of pentoxifylline in septic premies. Crit Care Med. Apr. 1999;27(4):695-7.

Hotchkiss JR et al. An agent-based and spatially explicit model of pathogen dissemination in the intensive care unit. Crit Care Med. 2005;33(1):168-176.

Vodovotz Y et al. In silico models of acute inflammation in animals. Shock. 2006;26(3):235-44.

Folcik et al., The Basic Immune Simulator: An agent-based model to study the interactions between innate and adaptive immunity, Theoretical Biology and Medical Modelling 2007, 4:39.

Orosz, et al. Simulating the Complexity of Immune Responses, Workshop 5: Immunology Models: Cell Signalling and Immune Dynamics (May 10-14, 2004), Mathematical Biosciences Institute. The Ohio State University.

Schedule, Workshop 5: Immunology Models: Cell Signalling and Immune Dynamics (May 10-14, 2004), Mathematical Biosciences Institute. The Ohio State University. (http://mbi.osu.edu/2003/ws5description.html#schedule).

Abstracts, Workshop 5: Immunology Models: Cell Signalling and Immune Dynamics (May 10-14, 2004), Mathematical Biosciences Institute. The Ohio State University. (http://mbi.osu.edu/2003/ws5abstracts.html).

Orosz et al. The Immune System Behaves like a Complex System and a Scale-free Network, Tenth Annual Swarm Agent-Based Simulation Meeting, SwarmFest 2006, Jun. 23-24, 2006, University of Notre Dame.

The Basic Immune Simulator, Web-archive (Aug. 24, 2006, http://web.archive.org/web/20060901113830/digitalunion.osu.edu/r2/summer06/sass/).

* cited by examiner

MODELING WOUND HEALING

CROSS REFERENCE TO RELATED APPLICATIONS

This application claims the benefit under 35 U.S.C. §119 (e) to U.S. Provisional Patent Application No. 60/850,690, filed Oct. 10, 2006 and U.S. Provisional Patent Application No. 60/850,896, filed Oct. 11, 2006, both of which are incorporated herein by reference in their entirety.

STATEMENT REGARDING FEDERAL FUNDING

The U.S. Government has a paid-up license in this invention and the right in limited circumstances to require the patent owner to license others on reasonable terms as provided for by the terms of Grant No(s). P50GM 53789-09 and R01DC005643, awarded by the National Institutes of Health.

BACKGROUND

Methods of simulating wound healing and associated inflammation using agent-based models and, optionally mathematical (differential equation-based) modeling are described herein.

Various approaches have been used to construct simulations of complex biologic processes. All these methods have distinct advantages and disadvantages. In vitro biological systems work well in many situations, but require physical facilities and often are not complex enough or accurate enough to effectively model in vivo systems. In silico (computer simulated) systems are becoming more sophisticated and, as described below, are becoming increasingly able to model biological systems. Two modeling systems are commonly, but not exclusively, utilized to model biological systems: equation-based modeling (EBM), or more specifically ordinary differential equations (ODE), and agent-based modeling (ABM).

The ODE type of modeling is a type of equation-based modeling that consists of establishing a series of differential equations that describe the sequential change in the states of the components of the system over time. The differential equations are derived from known and hypothesized kinetics of the components of the biologic system. This approach has been used for many years to describe chemical systems, for example Michaelis-Menten kinetics. The variables of the equations generally represent average concentrations of the various components. These systems of equations are generally most accurate in settings in which large numbers of individuals of these components are assumed to exist and to exert their effects in aggregate. When the numbers become small, differential equation descriptions break down. The behavior of the system with limited spatial information (e.g. compartments) can be characterized with ODE; if more precise spatial resolution is desired, partial differential equations (PDE) are more commonly used. If simple enough, ODE can be solved analytically. If not, they can be easily solved computationally using a variety of commercially available and free software, as well as proprietary designed for specific implementations of ODE models. Additionally, methods from nonlinear analysis can explore the properties of ODE without completely solving them. Because these equations are based on and describe biologic interactions, these models can potentially predict outcomes beyond the range of data on which these models were initially calibrated. In this latter aspect, EBM are different from statistical models. Furthermore, manipulation of a biologic mechanism can be entered into the model and an outcome derived (predicted).

The ABM type of modeling focuses on the rules and mechanisms of behavior of the individual components of a system, and may be more accurate than EBM in settings in which the stochastic actions of these agents is a better approximation of biological reality as compared to the actions of these components in aggregate. The components of a system are classified into types of "agents" by virtue of shared mechanisms that have been identified experimentally. The mechanisms are expressed as a series of conditional ("if-then") statements, and computer programs are written to describe the rules of behavior. An example would be the sequence of receptor activation involved in neutrophil adhesion. The model defines a "virtual world" based on characteristics of the reference system and generates populations of the various types of agents. The agents interact based on responses (defined by their rule systems) to inputs and outputs from their environment. For example, simulated cells would respond to variables in their immediate neighborhood, representing the extent of a cell's interaction with its extracellular milieu. The agents run in a parallel fashion to simulate simultaneous behavior, and the dynamics of the system are allowed to emerge from the multiple interactions among the agents over time. Consequently, all measured parameters and outcomes from the model are generated by the actions of the agents. The rules governing the behavior of agents should ideally be well-vetted, simple rules. Because ABMs are mechanistic models, any intervention that deals with a defined mechanism in the model can be simulated. Because they are based on rules, ABMs are often more intuitive to non-mathematicians than EBM (Ermentrout, G. B., et al. (1993). Journal of Theoretical Biology, 160(1), 97-133; An G. Agent-based computer simulation and SIRS: building a bridge between basic science and clinical trials. Shock 2001; 16(4):266-73; Vodovotz Y, Clermont G, Chow C, An G. Mathematical models of the acute inflammatory response. Curr Opin Crit. Care 2004; 10:383-90).

Wound healing is a complex, multi-step process that occurs in many tissues and organs in the body. In epithelial tissues, wound healing typically occurs in the following stages: platelet activation and cytokine release, inflammation, re-epithelialization, formation of granulation tissue and angiogenesis, matrix production, and scar formation and a remodeling phase (See, e.g., Hart J. Inflammation. 1: Its role in the healing of acute wounds. J Wound Care 2002; 11(6):205-9; Hart J. Inflammation. 2: Its role in the healing of chronic wounds. J Wound Care 2002; 11(7):245-9; Goldring S R. Inflammatory mediators as essential elements in bone remodeling. Calcif Tissue Int 2003; 73(2):97-100; Guilak F, Fermor B, Keefe F J, Kraus V B, Olson S A, Pisetsky D S, Setton L A, Weinberg J B. The role of biomechanics and inflammation in cartilage injury and repair. Clin Orthop 2004(423): 17-26; Ramadori G, Saile B. Inflammation, damage repair, immune cells, and liver fibrosis: specific or nonspecific, this is the question. Gastroenterology 2004; 127(3):997-1000; Redd M J, Cooper L, Wood W, Stramer B, Martin P. Wound healing and inflammation: embryos reveal the way to perfect repair. Philos Trans R Soc Lond B Biol Sci 2004; 359(1445):777-84 and Diegelmann R F, Evans M C. Wound healing: an overview of acute, fibrotic and delayed healing. Front Biosci 2004; 9:283-9). These processes represent "snapshots" of a continuum, which may take different amounts of time depending on the tissue being examined. Importantly, these ordered steps can become disrupted in many disease settings that are broadly characterized as exhibiting impaired or aberrant wound healing. Typically, in these settings inflammation is also deranged, as might be expected given the linkage between inflammation and wound healing described above.

SUMMARY

Presented herein are several examples of aberrant wound healing and the simulations that we have used to gain insight into the operant mechanisms as well as potential novel therapies for these conditions. Therefore, according to one embodiment of the present invention, a method is provided of simulating tissue healing. The method comprises using a mechanistic computer model of the interrelated effects of inflammation, tissue damage or dysfunction, and tissue healing to predict an outcome of healing of damaged tissue in vivo, thereby facilitating the prediction the outcome of healing of damaged tissue in clinical settings. The method typically is modeled on a computing device using an agent-based and/or equation-based modeling software and thus the modeling can be agent-based and/or equation-based. The model typically comprises a feed-forward loop of inflammation to damage to inflammation, wherein the feed-forward loop is regulated by one or more anti-inflammatory agents. In certain embodiments, the model comprises anti-inflammatory agents, such as, without limitation one of active TGF-β1 latent TGF-β1 and IL-10 or pro-inflammatory agents. Elements of the simulations may include, without limitation, one or more of active TGF-β1, latent TGF-β1, a TGF-β1 binding protein, IL-1β, TNF, TGF, IL-6, IL-8, IL-12, IFN-γ, VEGF, IL-10, TGF-α, EGF, IGF-1, basic FGF, acidic FGF, a prostaglandin (e.g., $PGE_2$), a matrix metalloproteinase (e.g., MMP-2, MMP-8, MMP-9, and their precursors), tissue inhibitor of a metalloproteinases, including (TIMP-1 and TIMP-2), HMGB1, RAGE (receptor for advanced glycation endproducts), or another alarm/danger signal (marker/mediator of tissue damage [P. Matzinger. The danger model: a renewed sense of self. Science 296 (5566):301-305, 2002]; e.g., urate crystals in gout, biological correlate of tissue damage heat shock protein 70, exctracellular matrix fragments, hyaluronic acid, advanced glycation endproducts), a soluble receptor for a biological agent (e.g., cytokines, "alarm/danger signals"), platelets, macrophages, neutrophils, B-cells, T-cells, dendritic cells, fibroblasts, keratinocytes, endothelial cells, smooth muscle cells, a microbe, and collagen.

The model may comprise a therapeutic or diagnostic agent as an element in order to simulate the action of that agent in the simulation. Thus, according to one embodiment, the model can simulate the impact of a therapeutic strategy for a disease or condition involving the interrelations among inflammation, tissue damage or dysfunction and tissue healing. In another non-limiting embodiment, the model is used to rationally design a drug, device, diagnostic, prophylaxis or therapeutic strategy for a disease or condition involving the interrelations among inflammation, tissue damage or dysfunction and tissue healing. In yet another non-limiting embodiment, the method is used in the diagnosis of a disease involving the interrelations among inflammation, tissue damage or dysfunction and tissue healing.

A non-limiting list of systems and disease states associated with wounds and wound healing that can be simulated according to various embodiments of the methods provided herein includes: diabetes, diabetic foot ulcers, necrotizing enterocolitis, ulcerative colitis, Crohn's disease, inflammatory bowel disease, restenosis (post-angioplasty or stent implantation), incisional wounding, excisional wounding, surgery, accidental trauma, pressure ulcer, stasis ulcer, tendon rupture, vocal fold phonotrauma, otitis media and pancreatitis and most of these, as well as others not listed herein, are well-characterized and are amenable to the methods described herein.

As each disease or condition can involve the interaction of different elements, the simulation/model of each disease or condition would include certain unique elements. For example and without limitation, the simulation/modeling methods and systems described herein can be used to model the following disease/condition and element pairs:

1. Diabetic foot ulcers and TNF as a pro-inflammatory agent, TGF-β1 as an anti-inflammatory agent, and advanced glycation end products as alarm/danger signals (markers of tissue damage).
2. Tissue healing in vocal folds and IL-1β and TNF as pro-inflammatory elements and IL-13 as an anti-inflammatory element.
3. Necrotizing enterocolitis and TNF as a pro-inflammatory element, IL-10 as an anti-inflammatory element, and HMGB1 as an alarm/danger signal (marker of tissue damage).
4. Post-angioplasty or post-stenting restenosis and TNF as a pro-inflammatory element, TGF-β1 as an anti-inflammatory element, and advanced glycation end products as alarm/danger signals.
5. An inflammatory bowel disease, such as Crohn's disease or ulcerative colitis and TNF as a pro-inflammatory element, TGF-β1 as an anti-inflammatory element, and HMGB1 as an alarm/danger signal.
6. Pancreatitis and TNF as a pro-inflammatory element, IL-10 as an anti-inflammatory element, and hyaluronic acid as an alarm/danger signal.
7. Tissue healing in external tissue trauma and TNF as a pro-inflammatory element, IL-10 as an anti-inflammatory element, and HMGB1 as an alarm/danger signal.
8. Healing of connective tissues of skin, mucosa, and other soft tissues and TNF and IL-1β as pro-inflammatory elements, $PGE_2$ as an anti-inflammatory element, and HMGB1 as an alarm/danger signal.
9. Otitis media with effusion, due to Eustachian tube obstruction and in the absence of infection or other causal agents, and IL-1β and TNF as pro-inflammatory elements, TGF-β and IL-10 as anti-inflammatory elements, and hyaluronic acid as an alarm/danger signal.

Also provided are computer implementations of any of the models/methods described herein. Thus provided according to one embodiment, is a computing device comprising a process implementing (comprising and embodying for purposes of implementation on the computing device) a mechanistic computer model of the interrelated effects of inflammation, tissue damage or dysfunction and tissue healing to predict an outcome of healing of damaged tissue in vivo.

BRIEF DESCRIPTION OF THE DRAWINGS

In FIG. 20, system state at time=50 for Case 1. The simulation domain is a cross-section consisting of a lumen layer (top), an epithelial layer, two tissue layers, and a blood layer (bottom). The system components are c_a—anti-inflammatory cytokines, d—damage, e_c—epithelial cells, b—bacteria, c—cytokines, m—resting macrophages, m_a—activated macrophages, NO—nitric oxide, ZO1—tight junction protein, N_a—activated neutrophils. At t=50 the bacteria has diffused through the tissue and has started an inflammation process. Damage-dependent endothelial barrier controls the movement into and out of the blood compartment. Some cytokines have penetrated into the blood, activating a small amount of neutrophils. FIG. 21 shows a time history of averaged component values in the epithelial layer for Case 1—partial hole. The initial level of epithelial cells is ⅓ in the hole and 1 for the rest of the layer. The inflammation process in the epithelial peaks around time=50. At that time the bacteria and inflammatory agents (c, m_a) start to decrease and the epithelial layer starts to heal (e_c, ZO1). The damage starts to decrease at around t=100. The system is close to a healthy state at the end of the simulation. FIG. 22 is a time history of averaged component values in the epithelial layer for Case 2—completely missing portion of the wall. The initial level of epithelial cells is 0 in the hole and 1 for the rest of the layer. The hole is closing much more slowly in this case. The inflammation persists and the damage increases throughout the simulation. In FIGS. 20-22 all numbers are unitless.

DETAILED DESCRIPTION

Figure 1:
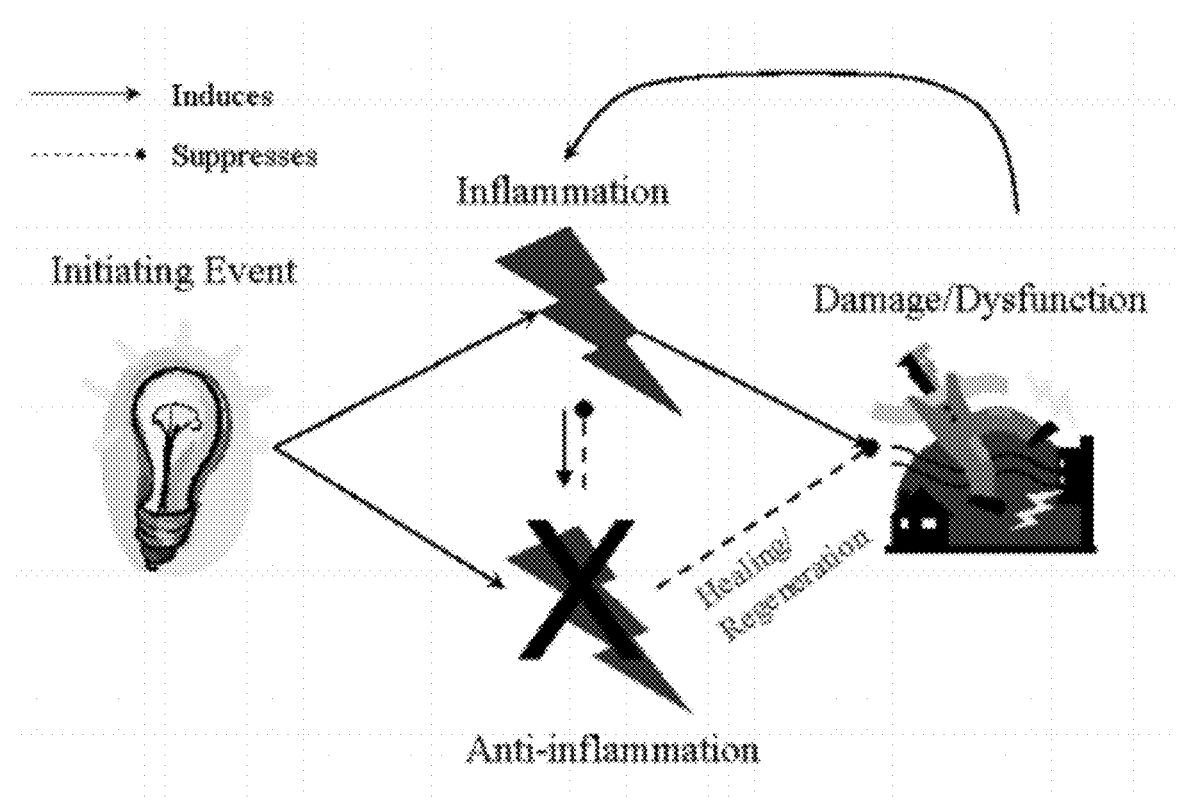
FIG. 1 is a schematic of the interplay among pro-inflammatory, anti-inflammatory, and wound healing processes. Solid arrow: induction; dashed line: suppression. In our model, an initiating stimulus (e.g. endotoxin or trauma) stimulates both pro- and anti-inflammatory pathways. Pro-inflammatory agents (e.g. TNF) cause tissue damage/dysfunction, which in turn stimulates further inflammation (e.g. through the release of "danger signals"). Anti-inflammatory agents (e.g. TGF-β1) both suppress inflammation and stimulate healing.

The human body has the inherent ability to heal a wide variety of its organs and tissues following damage from both chronic disease processes and acute traumatic injury. One goal of medicine has been to facilitate this intrinsic self-renewing ability by relieving damaged tissues from their functional burden and providing what was empirically perceived to be the ideal environment for tissue healing. Historically, emphasis has been placed upon replacing diseased tissues with synthetic, or more recently, transplanted or engineered tissues. While some tissues may indeed be irreparably damaged and thus require implantation or transplantation in order for the organism to regain even a modicum of the organ's function, a large fraction of patients on the cusp of organ failure would be better served by developing treatment modalities that embrace the historic principles of medicine: optimization of the regenerative potential intrinsic to many organ systems.

To achieve this goal, the pivotal role of inflammation must be recognized and understood in the context of both the initial damage process and in the various aspects of the healing response and tissue remodeling following injury (Hart, J. Inflammation. 1: Its role in the healing of acute wounds. J. Wound. Care 11, 205-209 (2002); Hart, J. Inflammation. 2: Its role in the healing of chronic wounds. J. Wound. Care 11, 245-249 (2002); Goldring, S. R. Inflammatory mediators as essential elements in bone remodeling. Calcif. Tissue Int. 73, 97-100 (2003); Guilak, F. et al. The role of biomechanics and inflammation in cartilage injury and repair. Clin. Orthop. 17-26 (2004); Ramadori, G. & Saile, B. Inflammation, damage repair, immune cells, and liver fibrosis: specific or non-specific, this is the question. Gastroenterology 127, 997-1000 (2004) and Redd, M. J., Cooper, L., Wood, W., Stramer, B., & Martin, P. Wound healing and inflammation: embryos reveal the way to perfect repair. Philos. Trans. R. Soc. Lond B Biol. Sci. 359, 777-784 (2004)). Moreover, therapeutic approaches involving temporary organ support, designed to allow the injured organ to regain function, (Nose, Y. & Okubo, H. Artificial organs versus regenerative medicine: is it true? Artif. Organs 27, 765-771 (2003)) themselves often cause additional inflammation due to the techniques/devices used and/or the surgical procedures necessary to implement these therapies (Hamilton, J. A. Nondisposable materials, chronic inflammation, and adjuvant action. J. Leukoc. Biol. 73, 702-712 (2003); Bostman, O. M. & Pihlajamaki, H. K. Adverse tissue reactions to bioabsorbable fixation devices. Clin. Orthop. 216-227 (2000); Goodacre, C. J., Kan, J. Y., & Rungcharassaeng, K. Clinical complications of osseointegrated implants. J. Prosthet. Dent. 81, 537-552 (1999); Tang, L. & Eaton, J. W. Inflammatory responses to biomaterials. Am. J. Clin. Pathol. 103, 466-471 (1995); DeVore, D. P. Long-term compatibility of intraocular lens implant materials. J. Long. Term. Eff. Med. Implants. 1, 205-216 (1991); DeLustro, F., Dasch, J., Keefe, J., & Ellingsworth, L. Immune responses to allogeneic and xenogeneic implants of collagen and collagen derivatives. Clin. Orthop. 263-279 (1990); Parelman, A. G. Sterile uveitis and intraocular lens implantation. J. Am. Intraocul. Implant. Soc. 5, 301-306 (1979); Thompson, L. O., Loebe, M., & Noon, G. P. What price support? Ventricular assist device induced systemic response. ASAIO J. 49, 518-526 (2003); Hampton, C. R. & Verrier, E. D. Systemic consequences of ventricular assist devices: alterations of coagulation, immune function, inflammation, and the neuroendocrine system. Artif. Organs 26, 902-908 (2002); Popovich, P. G. & Jones, T. B. Manipulating neuroinflammatory reactions in the injured spinal cord: back to basics. Trends Pharmacol. Sci. 24, 13-17 (2003); Kuhry, E., Jeekel, J., & Bonjer, H. J. Effect of laparoscopy on the immune system. Semin. Laparosc. Surg. 11, 37-44 (2004); Mutlu, L. K., Woiciechowsky, C., & Bechmann, I. Inflammatory response after neurosurgery. Best. Pract. Res. Clin. Anaesthesiol. 18, 407-424 (2004); Nian, M., Lee, P., Khaper, N., & Liu, P. Inflammatory cytokines and postmyocardial infarction remodeling. Circ. Res. 94, 1543-1553 (2004) and Sido, B., Teklote, J. R., Hartel, M., Friess, H., & Buchler, M. W. Inflammatory response after abdominal surgery. Best. Pract. Res. Clin. Anaesthesiol. 18, 439-454 (2004)). However, inflammation, both in its acute and chronic phases, is a highly complex process that: 1) is induced by a variety of stimuli, 2) is modulated by numerous cells and their products, and 3) affects different tissues in diverse ways (Nathan, C. Points of control in inflammation. Nature 420, 846-852 (2002)). Indeed, a holistic understanding of human immune/inflammatory function is lacking, despite enormous progress in studying the molecular and cellular substrates of the human immune system. This lack of a comprehensive framework has hindered the optimal design of pre-clinical and clinical studies aimed at the development of effective curative and regenerative medical therapies.

We have developed a series of mathematical models of the innate immune response as well as the effect of these mechanisms on organ function (Kumar, R., Clermont, G., Vodovotz, Y., & Chow, C.C. The dynamics of acute inflammation. J. Theoretical Biol. 230, 145-155 (2004); Clermont, G. et al. In silico design of clinical trials: a method coming of age. Crit. Care Med. 32, 2061-2070 (2004); Chow, C. C. et al. The acute inflammatory response in diverse shock states. Shock 24, 74-84 (2005); Reynolds, A. et al. A reduced mathematical model of the acute inflammatory response: I. Derivation of model and analysis of anti-inflammation. J. Theor. Biol. (2006, 242:220-236); Day, J. et al. A reduced mathematical model of the acute inflammatory response: II. Capturing scenarios of repeated endotoxin administration. J. Theor. Biol. (2006, 242:237-256); Prince, J. M. et al. In silico and in vivo approach to elucidate the inflammatory complexity of CD14-deficient mice. Mol. Med. (2006, 12:88-96) and Lagoa, C. E. et al. The role of initial trauma in the host's response to injury and hemorrhage: Insights from a comparison of mathematical simulations and hepatic transcriptomic analysis. Shock. (2006, 26:592-600); Kumar, R.; Chow, C. C.; Bartels, J.; Clermont, G.; Vodovotz, Y. A mathematical simulation of the inflammatory response to anthrax infection. Shock. 2007. (In Press)). Though in some cases informed by circulating mediators, all of these models express the physiological derangement experienced by individual organs in terms of a global tissue damage/dysfunction equation. These models share the feed-forward loop of inflammation→damage→inflammation, which is kept in check by the actions of anti-inflammatory agents (FIG. 1). The close correlation between the output of the mathematical model of inflammation and experimental data suggests that a common inflammatory response underlies diverse shock states, (Chow, C. C. et al. Shock 24, 74-84 (2005)) and raises the possibility of modeling the inflammatory process in silico (Clermont, G. et al. Crit. Care Med. 32, 2061-2070 (2004)).

In the context of the present disclosure, the modeling approach of interest involves Agent-Based Models (ABMs). In such models, individual components of a given complex system interact based on rules whose outcomes are partially based on stochastic processes (Ermentrout, G. B., et al. (1993). Journal of Theoretical Biology, 160(1), 97-133). More specifically, ABM involves discrete event simulation to study the behavior of complex systems. "Agents" in ABM represent the component parts of the system that contribute to the system's behavior. The rules can involve mathematical equations or "If . . . . Then" conditional statements. On the basis of these rules, a simulated environment is created to allow agents to respond and interact, and to allow for quantitative outputs of the simulation. The relative importance of various rules is dictated by model parameters.

ABM is the most direct initial approach to simulate the temporal evolution of a complex system and to encode complicated time-dependent cellular and molecular events that occur during inflammation and wound healing (An, G. (2005). Mathematical modeling in medicine: a means, not an end. Critical Care Medicine, 33(1), 253-254; Smallwood, R. H., Holcombe, W. M. L., & Walker, D. C. (2004). Development and validation of computational models of cellular interaction. Journal of Molecular Histology, 35, 659-665; Vodovotz, Y., et al. (2004). Current Opinion in Critical Care, 10(5), 383-390 and Walker, D. C., et al. (2004). IEEE Transactions on Nanobioscience, 3(3), 153-163). ABM is also a flexible platform that allows for the addition of new components in evolving models. Because ABM is stochastic in nature, it provides an elegant means of introducing inter-individual variability in the healing process.

It needs to be emphasized that EBM, or more specifically ODE, and ABM methods of modeling are complementary, and both can, and in many instances, preferably would be used to provide mathematical characterization of a complex dynamical system (see, for example, Vodovotz, Y, et al.

"Mathematical Models of the Acute Inflammatory Process," Curr. Op. Crit. Care 2004, 10:383-390 (outlining ABM and ODE methods and describing ODE and ABM models of the Acute Inflammatory Response associated with sepsis) and Bonabeau, E. "Agent-based modeling: Methods of Techniques for simulating human systems," Proc. Nat'l Acad. Sci. U.S.A. 2002 99(Suppl. 3):7280-7287). EBM or ODE models focus on the collective behavior of a population of individual components (e.g., concentrations). Consequently, the values of parameters (e.g. half-lives of various components) in EBM or ODE models can often be directly obtained from experiments. Agent-based models simulate the behavior of actual individuals and can easily encode complicated, history-dependent internal states of cells that are not easily captured in EBM or ODE models. Additionally, the ABM approach provides a very intuitive means of translation of basic science data (for a non-mathematician) and allows flexibility in proposing interventions. The downside is that extensive computational power may be required to simulate large numbers representative of real systems, and thus the values of many parameters in ABM can be difficult to obtain directly from experiments. It is therefore sometimes more difficult to validate and calibrate ABM directly with experimental data. The recognition that both approaches have their advantages and limitations has placed emphasis on cross-platform validation (see below). This disclosure describes specific models of wound healing using ODE and ABM, validation strategies for both, and a series of in silico experiments and results that demonstrate the potential uses of these forms of analysis.

Figure 10:
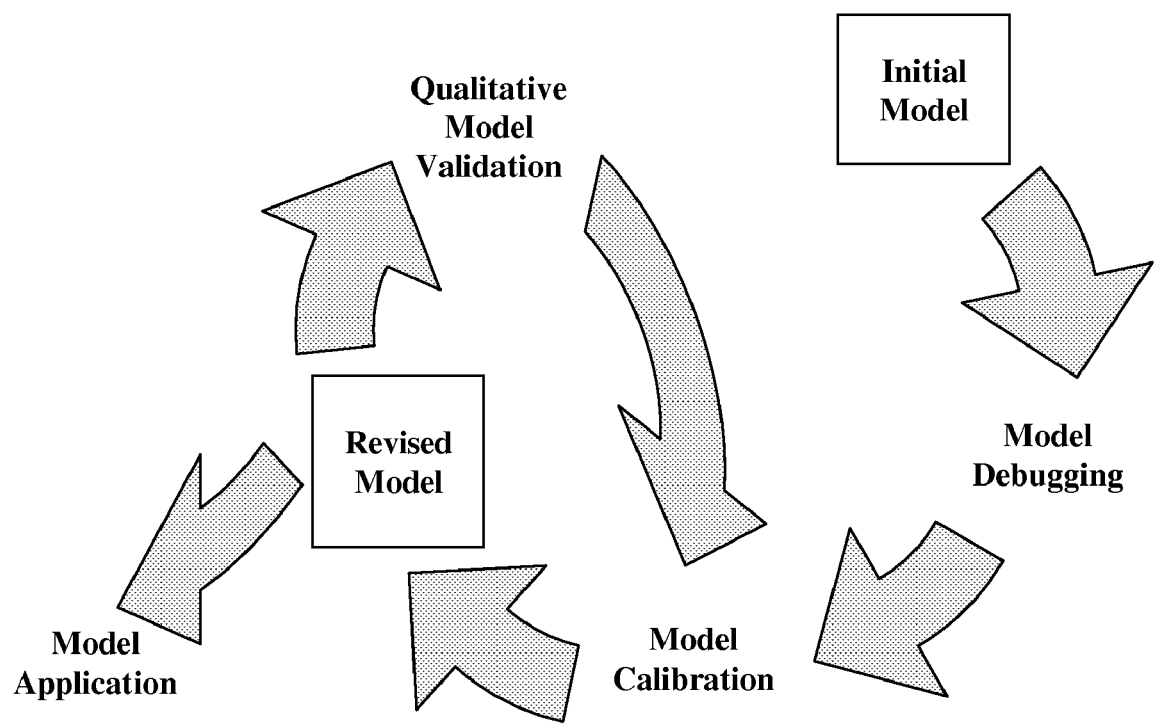
FIG. 10 illustrates the iterative processes in model building. To create an initial model, some of the model's parameters are estimated through an iterative validation and calibration process. The aim is to develop a model that can represent the reality of interest accurately. First, model debugging is carried out to ensure that the model implements its code correctly. Then, a qualitative validation is carried out to test whether the model reproduces trends in empirical observations. If the two data sets fail to match according to pre-specified criteria, the model is calibrated to obtain values of parameters that minimize the difference between model predictions and observations. If the match is inadequate, the rules of the model are revisited to produce a better qualitative match. The qualitative validation-calibration iterative process continues until it eventually yields a satisfactory revised model. The final model is applied for simulations and subsequent in silico experiments.

FIG. 10 describes the basic procedures involved in building and calibrating an ABM. The steps involve (1) initial model construction using empirical input (generally based on the consensus in the scientific literature), which is subjected to rules for interactions among inputs, followed by an iterative process of (2) qualitative validation and (3) calibration to revise the model. Validation typically involves the satisfactory comparison of data predicted by the model to known empirical data. Calibration typically involves iterative adjustment of model parameters needed to achieve validation. Finally, the calibrated model is tested by comparing its quantitative predictions against data from experiments carried out specifically for the purpose of model validation (and, importantly, which were not used as part of the calibration process).

As used herein "agent-based modeling" is a rules-based, stochastic modeling framework in which agents obey simple rules that, as a whole, generate complex system behavior.

As used herein, a "differential equation" is an equation in which the derivatives of a function appear as variables. In equation-based modeling (EBM), the model is a set of equations, and execution consists of evaluating them. An ordinary differential equation (or ODE) is a relation that contains functions of only one independent variable, and one or more of its derivatives with respect to that variable.

As used herein a "biological system" is a subset or microcosm of the physical structure and/or activities that are present in a living organism, such as a cell, plant, animal, vertebrate or invertebrate. A biological system may be, without limitation, an organ, a biochemical or biological process, a biochemical process present in an organ, tissue or organism, a pathogen and infected tissue, diseased tissue, etc. In the context of the present disclosure, biological systems include, for example and without limitation, cells, tissue, organs, cells and factors (chemical compounds, proteins such as cytokines, DNA, RNA, and other cellular and non-cellular elements) involved in any fashion with the process of tissue healing in any context. As such, "tissue healing" refers to the repair of any tissue (e.g. skin, blood vessels, vocal folds, and any organ), and generally encompasses the components listed above. Generally, cells involved in tissue healing include cells associated with blood vessels (e.g., platelets, red blood cells, and endothelial cells); inflammatory cells (e.g., neutrophils, monocytes, macrophages, eosinophils, basophils, T cells, B cells, and dendritic cells); and cells involved in the tissue repair (e.g. fibroblasts, myofibroblasts, and tissue-specific epithelial cells such as keratinocytes in skin). Examples of tissue healing include the repair of skin lesions (either acute [e.g. cuts] or more chronic [e.g. diabetic foot ulcers, pressure ulcers]); vocal folds; mucosa of the head and neck (e.g., subglottic mucosa, middle ear mucosa); intestine (e.g. necrotizing enterocolitis); blood vessels (e.g. restenosis following angioplasty or stenting of blood vessels occluded by atherosclerotic plaque). Elements thereof include organs, tissue, cells and factors that are physically present and/or active in the biological system. As used herein, the phrases "wound healing" and "tissue healing" both refer to healing of damaged tissue, no matter the cause of the damage.

As used herein a "modeling system" is a computational framework by which a biological system is modeled. A modeling system embodies various elements of a biological system. As used herein an "element," in the context of modeling a biological system, means any components of the model, as described above.

A modeling system may be "calibrated" by assigning, relating, comparing, or otherwise comporting elements of a modeled system with actual data values obtained directly or in any other manner from actual data values, for example and without limitation, by statistical computation methods or other mathematical methods. Calibration typically involves iterative adjustment of model parameters needed to achieve a situation in which the output of a mathematical model matches the experimentally determined time courses of the analytes (variables) in the model. The quality of the model and the calibration procedure are typically assessed by a process of "validation", in which predictions of the model are tested against data withheld from the calibration procedure.

Figure 17:
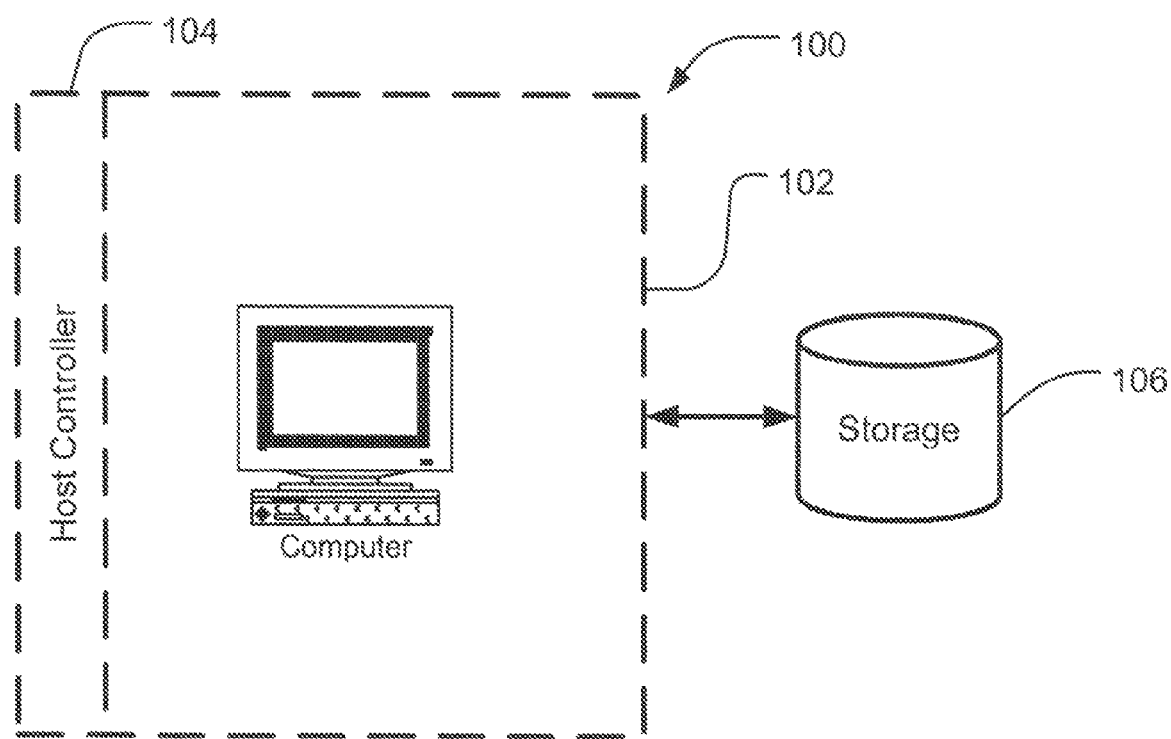
FIG. 17 illustrates one embodiment of a computer system for implementing a modeling system as described below.

Modeling systems are implemented on a computing device (computer) as processes. In the context of computing, a process is, broadly speaking any computer-implemented activity that generates an outcome, such as implementation of a mathematical or logical formula or operation, algorithm, etc. FIG. 17 illustrates one embodiment of a system 100 for implementing a modeling system. The system 100 may include a device 102 operating under the command of a controller 104. Device 102 may be referred to herein, without limitation, as a computer or computing device. The broken lines are intended to indicate that in some implementations, the controller 104, or portions thereof considered collectively, may instruct one or more elements of the device 102 to operate as described. Accordingly, the functions associated with the modeling methods (e.g., processes, software, programs) described herein may be implemented as software executing in the system 100 and controlling one or more elements thereof. An example of a device 102 in accordance with one embodiment of the present invention is a general-purpose computer capable of responding to and executing instructions in a defined manner. Other examples include a special-purpose computer including, for example, a personal computer (PC), a workstation, a server, a laptop computer, a web-enabled telephone, a web-enabled personal digital assistant (PDA), a microprocessor, an integrated circuit, an application-specific integrated circuit, a microprocessor, a microcontroller, a network server, a Java virtual machine, a logic array, a programmable logic array, a micro-computer, a mini-computer, or a large frame computer, or any other component, machine, tool, equipment, or some combination thereof capable of responding to and executing instructions. In one non-limiting embodiment, system 100 is implemented as a PC. Furthermore, the system 100 may include a central processing engine including a baseline processor, memory, and communications capabilities. The system 100 also may include a communications system bus to enable multiple processors to communicate with each other. In addition, the system 100 may include storage 106 in the form of a disk drive, cartridge drive, and control elements for loading new software. In embodiments of the invention, one or more reference values may be stored in a memory associated with the device 102.

Embodiments of the controller 104 may include, for example, a program, code, a set of instructions, or some combination thereof, executable by the device 102 for independently or collectively instructing the device 102 to interact and operate as programmed. One example of a controller 104 is a software application (for example, operating system, browser application, client application, server application, proxy application, on-line service provider application, and/or private network application) installed on the device 102 for directing execution of instructions. In one embodiment, the controller 104 may be a Windows™ based operating system. The controller 104 may be implemented by utilizing any suitable computer language (e.g., C\C++, UNIX SHELL SCRIPT, PERL, JAVA, JAVASCRIPT, HTML/DHTML/XML, FLASH, WINDOWS NT, UNIX/LINUX, APACHE, RDBMS including ORACLE, INFORMIX, and MySQL) and/or object-oriented techniques.

In one embodiment, the controller 104 may be embodied permanently or temporarily in any type of machine, component, physical or virtual equipment, storage medium, or propagated signal capable of delivering instructions to the device 102. In particular, the controller 104 (e.g., software application, and/or computer program) may be stored on any suitable computer readable media (e.g., disk, device, or propagated signal), readable by the device 102, such that if the device 102 reads the storage medium, the functions described herein are performed. For example, in one embodiment, the controller 104 may be embodied in various computer-readable media for performing the functions associated with processes embodying the modeling methods.

Processes for implementing modeling systems are typically embodied in software programs. Non-limiting examples of suitable software programs for developing the modeling systems described herein include: StarLogo®, NetLogo®, Swarm (Swarm Development Group wiki), XPPAUT (an ODE simulation program), Mathematica®; an ABM simulation program and MATLAB®; an ODE simulation program. These programs are agent-based modeling systems, though, as is typical of such software, elements of EBM or ODE modeling can be readily implemented within the software.

Therefore, according to one embodiment of the present invention, a method is provided of simulating tissue healing. The method comprises using a mechanistic computer model of the interrelated effects of inflammation, tissue damage or dysfunction and tissue healing to predict an outcome of healing of damaged tissue in vivo, thereby predicting the outcome of healing of damaged tissue in vivo. The method typically is modeled on a computing device using an agent-based and/or equation-based modeling software and thus the modeling can be agent-based and/or equation-based. The model typically comprises a feed-forward loop of inflammation to damage to inflammation, wherein the feed-forward loop is regulated by one or more anti-inflammatory agents. In certain embodiments, the model comprises anti-inflammatory agents, such as, without limitation one of active TGF-β1 latent TGF-β1 and IL-10 or pro-inflammatory agents. Elements of the simulations may include, without limitation, one or more of active TGF-β1, latent TGF-β1, a TGF-β1 binding protein, IL-1β, TNF, TGF, IL-6, IL-8, IL-12, IFN-γ, VEGF, IL-10, TGF α, EGF, IGF-1, basic FGF, acidic FGF, a prostaglandin (e.g., PGE2), a matrix metalloproteinase (e.g., MMP-2, MMP-8, MMP-9, and their precursors), tissue inhibitor of a metalloproteinases, including (TIMP-1 and TIMP-2), HMGB1, RAGE (receptor for advanced glycation endproducts), or another alarm/danger signal (e.g., urate crystals in gout, biological correlate of tissue damage heat shock protein 70, extracellular matrix fragments, hyaluronic acid, advanced glycation endproducts), a soluble receptor for a biological agent (e.g., cytokines, "alarm/danger signals"), platelets, macrophages, neutrophils, B-cells, T-cells, dendritic cells, fibroblasts, keratinocytes, endothelial cells, smooth muscle cells, a microbe, and collagen.

The model may comprise a therapeutic or diagnostic agent as an element in order to simulate the action of that agent in the simulation. By accurately simulating the impact of such an agent on a biological system, much of the cost, time, labor and resources, such as laboratory animals involved with early-stage research can be avoided by the in silico modeling. Thus, the model can simulate the impact of a therapeutic strategy for a disease or condition involving the interrelations among inflammation, tissue damage or dysfunction and tissue healing. In another non-limiting embodiment, the model is used to rationally design a drug, device, diagnostic, prophylaxis or therapeutic strategy for a disease or condition involving the interrelations among inflammation, tissue damage or dysfunction and tissue healing. In yet another embodiment, the method is used in the diagnosis of a disease involving the interrelations among inflammation, tissue damage or dysfunction and tissue healing.

A large variety of systems and disease states associated with wounds and wound healing can be simulated according to the methods described herein. A non-limiting list of these disease states includes: diabetes, diabetic foot ulcers, necrotizing enterocolitis, ulcerative colitis, Crohn's disease, inflammatory bowel disease, restenosis (post-angioplasty or stent implantation), incisional wounding, excisional wounding, surgery, accidental trauma, pressure ulcer, stasis ulcer, tendon rupture, vocal fold phonotrauma, otitis media and pancreatitis and most of these, as well as others not listed herein, are well-characterized and are amenable to the methods described herein.

As each disease or condition can involve the interaction of different elements, the simulation/model of each disease or condition would include certain unique elements. For example and without limitation, the following disease/condition and element pairs are relevant:
1. Diabetic foot ulcers and TNF as a pro-inflammatory agent, TGF-β1 as an anti-inflammatory agent, and advanced glycation end products as alarm/danger signals (markers of tissue damage).
2. Tissue healing in vocal folds and IL-1β and TNF as pro-inflammatory elements and IL-13 as an anti-inflammatory element.
3. Necrotizing enterocolitis and TNF as a pro-inflammatory element, IL-10 as an anti-inflammatory element, and HMGB1 as an alarm/danger signal (marker of tissue damage).
4. Post-angioplasty or post-stenting restenosis and TNF as a pro-inflammatory element, TGF-β1 as an anti-inflammatory element, and advanced glycation end products as alarm/danger signals.
5. An inflammatory bowel disease, such as Crohn's disease or ulcerative colitis and TNF as a pro-inflammatory element TGF-β1 as an anti-inflammatory element, and HMGB1 as an alarm/danger signal.
6. Pancreatitis and TNF as a pro-inflammatory element, IL-10 as an anti-inflammatory element, and hyaluronic acid as an alarm/danger signal.

7. Tissue healing in external tissue trauma and TNF as a pro-inflammatory element, IL-10 as an anti-inflammatory element, and HMGB1 as an alarm/danger signal.
8. Healing of connective tissues of skin, mucosa, and other soft tissues and TNF and IL-1β as pro-inflammatory elements, $PGE_2$ as an anti-inflammatory element, and HMGB1 as an alarm/danger signal.
9. Otitis media with effusion, due to Eustachian tube obstruction and in the absence of infection or other causal agents, and IL-1β and TNF as pro-inflammatory elements, TGF-β and IL-10 as anti-inflammatory elements and hyaluronic acid as an alarm/danger signal.

As described above, all of these methods can be simulated by modeling on a computer system. Thus, also provided is a computing device comprising a process comprising a mechanistic computer model of the interrelated effects of inflammation, tissue damage or dysfunction and tissue healing to predict an outcome of healing of damaged tissue in vivo. As mentioned above, a process is a computer implementation of the methods, typically involving software and hardware configurations embodying and implementing those processes.

The following provides further detail on three disease states modeled in the Examples.

Diabetic Ulcers

Tissue healing is a process that involves both inflammation and the resolution of the inflammatory response, which culminates in collagen deposition and remodeling (Hart J. Inflammation. 1: Its role in the healing of acute wounds. J Wound Care 2002; 11(6):205-9; Hart J. Inflammation. 2: Its role in the healing of chronic wounds. J Wound Care 2002; 11(7):245-9; Goldring S R. Inflammatory mediators as essential elements in bone remodeling. Calcif Tissue Int 2003; 73(2):97-100; Guilak F, Fermor B, Keefe F J, Kraus V B, Olson S A, Pisetsky D S, Setton L A, Weinberg J B. The role of biomechanics and inflammation in cartilage injury and repair. Clin Orthop 2004(423): 17-26; Ramadori G, Saile B. Inflammation, damage repair, immune cells, and liver fibrosis: specific or nonspecific, this is the question. Gastroenterology 2004; 127(3):997-1000; Redd M J, Cooper L, Wood W, Stramer B, Martin P.

Wound healing and inflammation: embryos reveal the way to perfect repair. Philos Trans R Soc Lond B Biol Sci 2004; 359(1445):777-84 and Diegelmann R F, Evans M C. Wound healing: an overview of acute, fibrotic and delayed healing. Front Biosci 2004; 9:283-9). The first phase of the wound healing response involves the degranulation of platelets and infiltration of inflammatory cells, followed by proliferation of fibroblasts and epithelial cells that deposit collagen and cause contraction of wounds. Wound healing is dysfunctional as a consequence of many diseases and stresses to a given tissue or organ. Below, we discuss several such conditions and the simulations we have created in an attempt to drive the creation of new therapeutics for these conditions. Rodent models of diabetes display impaired wound repair, with decreased wound tensile strength and collagen deposition in implanted sponges (Broadley K N, Aquino A M, Hicks B, Ditesheim J A, McGee G S, Demetriou A A, Woodward S C, Davidson J M. Growth factors bFGF and TGF beta accelerate the rate of wound repair in normal and in diabetic rats. Int J Tissue React 1988; 10(6):345-53; Bitar M S, Labbad Z N. Transforming growth factor-beta and insulin-like growth factor-I in relation to diabetes-induced impairment of wound healing. J Surg Res 1996; 61(1): 113-9; Broadley K N, Aquino A M, Hicks B, Ditesheim J A, McGee G S, Demetriou A A, Woodward S C, Davidson J M. The diabetic rat as an impaired wound healing model: stimulatory effects of transforming growth factor-beta and basic fibroblast growth factor. Biotechnol Ther 1989; 1(1):55-68; Schaffer M R, Tantry U, Efron P A, Ahrendt G M, Thornton F J, Barbul A. Diabetes-impaired healing and reduced wound nitric oxide synthesis: a possible pathophysiologic correlation. Surgery 1997; 121(5):513-9 and Goodson W H, III, Hunt T K. Wound collagen accumulation in obese hyperglycemic mice. Diabe 1986; 35(4):491-5). Collagen organization in healing wounds is also poor (Broadley K N, Int J Tissue React 1988; 10(6):345-53). Furthermore, diabetic wounds have deficits in neovascularization (Fahey T J, III, Sadaty A, Jones W G, Barber A, Smoller B, Shires G T. Diabetes impairs the late inflammatory response to wound healing. J Surg Res 1991; 50(4):308-13) and decreased levels of DNA and protein (Broadley K N, Aquino A M, Hicks B, Ditesheim J A, McGee G S, Demetriou A A, Woodward S C, Davidson J M. Growth factors bFGF and TGF beta accelerate the rate of wound repair in normal and in diabetic rats. Int J Tissue React 1988; 10(6):345-53 and Broadley K N, Aquino A M, Hicks B, Ditesheim J A, McGee G S, Demetriou A A, Woodward S C, Davidson J M. The diabetic rat as an impaired wound healing model: stimulatory effects of transforming growth factor-beta and basic fibroblast growth factor. Biotechnol Ther 1989; 1(1):55-68). Pro-inflammatory cytokines such as tumor necrosis factor-α (TNF) (Rapala K. The effect of tumor necrosis factor-alpha on wound healing. An experimental study. Ann Chir Gynaecol Suppl 1996; 211:1-53) and interferon-γ (IFN-γ) (Adelmann-Grill B C, Hein R, Wach F, Krieg T. Inhibition of fibroblast chemotaxis by recombinant human interferon gamma and interferon alpha. J Cell Physiol 1987; 130(2):270-5; Granstein R D, Deak M R, Jacques S L, Margolis R J, Flotte T J, Whitaker D, Long F H, Amento E P. The systemic administration of gamma interferon inhibits collagen synthesis and acute inflammation in a murine skin wounding model. J Invest Dermatol 1989; 93(1):18-27 and Miles R H, Paxton T P, Zacheis D, Dries D J, Gamelli R L. Systemic administration of interferon-gamma impairs wound healing. J Surg Res 1994; 56(3):288-94) inhibit wound healing both in vitro and in vivo. Interleukin-6 (IL-6), a cytokine central to inflammation (Kamimura D, Ishihara K, Hirano T. IL-6 signal transduction and its physiological roles: the signal orchestration model. Rev Physiol Biochem Pharmacol 2003; 149:1-38 and Naka T, Nishimoto N, Kishimoto T. The paradigm of IL-6: from basic science to medicine. Arthritis Res 2002; 4 Suppl 3:S233-S242) but whose role may switch from pro- to anti-inflammatory during the inflammatory response (Opal S M, DePalo V A. Anti-inflammatory cytokines. Chest 2000; 117(4): 1162-72), is also necessary for proper healing (Gallucci R M, Simeonova P P, Matheson J M, Kommineni C, Guriel J L, Sugawara T, Luster M I. Impaired cutaneous wound healing in interleukin-6-deficient and immunosuppressed mice. FASEB J 2000; 14(15):2525-31; Gallucci R M, Sugawara T, Yucesoy B, Berryann K, Simeonova P P, Matheson J M, Luster M I. Interleukin-6 treatment augments cutaneous wound healing in immunosuppressed mice. J Interferon Cytokine Res 2001; 21(8):603-9 and Lin Z Q, Kondo T, Ishida Y, Takayasu T, Mukaida N. Essential involvement of IL-6 in the skin wound-healing process as evidenced by delayed wound healing in IL-6-deficient mice. J Leukoc Biol 2003; 73(6):713-21). Interleukin-10 (IL-10), a potent anti-inflammatory cytokine, appears to suppress inflammation and induce the remodeling necessary for proper wound healing (Ohshima T, Sato Y. Time-dependent expression of interleukin-10 (IL-10) mRNA during the early phase of skin wound healing as a possible indicator of wound vitality. Int J Legal Med 1998; 111(5):251-5 and Sato Y, Ohshima T, Kondo T. Regulatory role of endogenous interleukin-10 in cutaneous inflammatory response of murine wound healing. Biochem Biophys Res Commun 1999; 265(1): 194-9). One cytokine that is central to the wound healing cascade is transforming growth factor-β1 (TGF-β1) (Roberts A B, Sporn M B. Transforming growth factor-b. In: Clark R A F, editor. The Molecular and Cellular Biology of Wound Repair. New York: Plenum Press, 1996:275-308 and Kulkarni A B, Thyagarajan T, Letterio J J. Function of cytokines within the TGF-beta superfamily as determined from transgenic and gene knockout studies in mice. Curr Mol Med 2002; 2(3):303-27). TGF-β1, like all isoforms of TGF-β, is produced in a latent form, which must be activated in order to exert its biological effects. The TGF-β1 precursor homodimerizes intracellularly, and is then cleaved extracellularly to yield the active TGF-β1 dimer as well as the remaining portion of its dimerized precursor, the latency-associated peptide (LAP). Under physiological conditions, TGF-β1 is expressed almost completely in its latent form, which consists of the active TGF-β1 dimer bound non-covalently to LAP. Additional proteins such as α2-macroglobulin, latent TGF-β1 binding proteins (Koli K, Saharinen J, Hyytiainen M, Penttinen C, Keski-Oja J. Latency, activation, and binding proteins of TGF-beta. Microsc Res Tech 2001; 52(4):354-62), or proteoglycans (e.g. decorin) (Border W A, Noble N A. Transforming growth factor b in tissue fibrosis. N Engl J Med 1994; 331:1286-92) are bound to latent TGF-β1 in what is known as the large latent complex. Latency-associated peptide and other proteins must be dissociated from latent TGF-β1, in a process known as activation, before TGF-β1 gains biological activity (Flaumenhaft R, Kojima S, Abe M, Rifkin D B. Activation of latent transforming growth factor b. Advances in Pharmacology 1993; 24:51-76). Numerous agents, including plasmin, transglutaminase Flaumenhaft R, et al. 1993; 24:51-76, cytokines Flaumenhaft R, et al. 1993; 24:51-76, radiation (Barcellos-Hoff M H, Derynck R, Tsang ML-S, Weatherbee J A. Transforming growth factor-b activation in irradiated murine mammary gland. J Clin Invest 1994; 93:892-9), oxygen free radicals (Barcellos-Hoff M H, Dix T A. Redox mediated activation of latent transforming growth factor-b1. Mol Endocrinol 1996; 10:1077-83), and nitric oxide (NO) (Vodovotz Y, Chesler L, Chong H, Kim S J, Simpson J T, DeGraff W, Cox G W, Roberts A B, Wink D A, Barcellos-Hoff M H. Regulation of transforming growth factor-b1 by nitric oxide. Cancer Res 1999; 59:2142-9) can activate latent TGF-β1. Of note, there are multiple regulatory intersections among TNF, IL-6, IL-10, IFN-γ, and TGF-β1 (Nathan C. Points of control in inflammation. Nature 2002; 420(6917):846-52), and much of this complexity has been captured in our equation-based models of inflammation (Vodovotz Y, Clermont G, Chow C, An G. Mathematical models of the acute inflammatory response. Curr Opin Crit. Care 2004; 10:383-90 and Chow C C, Clermont G, Kumar R, Lagoa C, Tawadrous Z, Gallo D, Betten B, Bartels J, Constantine G, Fink M P, Billiar T R, Vodovotz Y. The acute inflammatory response in diverse shock states. Shock 2005; 24:74-84).

Below are described several specific examples of deranged inflammation and wound healing in humans, and how computer simulations of inflammation and healing can yield novel insights into therapeutic modalities.

Deranged Inflammation and Wound Healing in Diabetic Foot Ulcers

Both inflammation and wound healing are deranged in chronic, non-healing foot ulcers, constituting a major complication of diabetes. Diabetic foot ulcers (DFU) are caused by both vascular and neurologic complications of diabetes, in combination with persistent opportunistic infections (Boulton A J, Meneses P, Ennis W J. Diabetic foot ulcers: A framework for prevention and care. Wound Repair Regen 1999; 7(1):7-16 and Browne A C, Sibbald R G. The diabetic neuropathic ulcer: an overview. Ostomy Wound Manage 1999; 45(1A Suppl):6S-20S) and deficient wound healing (Diegelmann R F, et al. Front Biosci 2004; 9:283-9; Koivukangas V, Annala A P, Salmela P I, Oikarinen A. Delayed restoration of epidermal barrier function after suction blister injury in patients with diabetes mellitus. Diabet Med 1999; 16(7):563-7; Pecoraro R E, Ahroni J H, Boyko E J, Stensel V L. Chronology and determinants of tissue repair in diabetic lower-extremity ulcers. Diabe 1991; 40(10):1305-13 and Morain W D, Colen L B. Wound healing in diabetes mellitus. Clin Plast Surg 1990; 17(3):493-501). Over 10 million Americans carry a diagnosis of diabetes, and an estimated 5 million more are undiagnosed diabetics (Harris M I, Flegal K M, Cowie C C, Eberhardt M S, Goldstein D E, Little R R, Wiedmeyer H M, Byrd-Holt D D. Prevalence of diabetes, impaired fasting glucose, and impaired glucose tolerance in U.S. adults. The Third National Health and Nutrition Examination Survey, 1988-1994. Diabetes Care 1998; 21(4):518-24). The incidence of foot ulcer in this population approaches 2% per year (Ramsey S D, Newton K, Blough D, McCulloch D K, Sandhu N, Reiber G E, Wagner E H. Incidence, outcomes, and cost of foot ulcers in patients with diabetes. Diabetes Care 1999; 22(3):382-7). With reported average treatment costs in 1999 ranging from $2,500 USD to almost $14,000 USD per year, diabetic foot ulcers (DFU) represent a significant financial burden on society (Koivukangas V, et al. Diabet Med 1999; 16(7):563-7; Pecoraro R E, et al. Diabe 1991; 40(10):1305-13; Morain W D et al. Clin Plast Surg 1990; 17(3):493-501; Ramsey S D, et al. Diabetes Care 1999; 22(3):382-7; Holzer S E, Camerota A, Martens L, Cuerdon T, Crystal-Peters J, Zagari M. Costs and duration of care for lower extremity ulcers in patients with diabetes. Clin Ther 1998; 20(1):169-81 and Boyko E J, Ahroni J H, Smith D G, Davignon D. Increased mortality associated with diabetic foot ulcer. Diabet Med 1996; 13(11):967-72. Additionally, DFU are responsible for more than 50,000 major lower extremity amputations in the United States every year (Levin M E. Diabetic foot ulcers: pathogenesis and management. J et Nurs 1993(5): 191-8). Notably, diabetics with foot ulcers have more than twice the mortality of diabetics with healthy feet (Boyko E J, Ahroni J H, Smith DG, Davignon D. Increased mortality associated with diabetic foot ulcer. Diabet Med 1996; 13(11): 967-72). Diabetics are known to have elevated levels of TNF (Hussain M J, Peakman M, Gallati H, Lo S S, Hawa M, Viberti G C, Watkins P J, Leslie R D, Vergani D. Elevated serum levels of macrophage-derived cytokines precede and accompany the onset of IDDM. Diabetologia 1996; 39(1): 60-9 and Harsch I A, Brzozowski T, Bazela K, Konturek S J, Kukharsky V, Pawlik T, Pawlowski E, Hahn E G, Konturek P C. Impaired gastric ulcer healing in diabetic rats: role of heat shock protein, growth factors, prostaglandins and proinflammatory cytokines. Eur J Pharmacol 2003; 481(2-3):249-60), and studies have suggested a relatively reduced expression of active TGF-β1 in DFU (Jude E B, Blakytny R, Bulmer J, Boulton A J, Ferguson M W. Transforming growth factor-beta 1, 2, 3 and receptor type I and II in diabetic foot ulcers. Diabet Med 2002; 19(6):440-7).

A standard procedure for DFU is wound debridement, which is effective in approximately 25% of patients. While numerous studies in animal models of diabetic wound healing have demonstrated efficacy of single growth factors such as platelet-derived growth factor (PDGF) (Greenhalgh D G, Sprugel K H, Murray M J, Ross R. PDGF and FGF stimulate wound healing in the genetically diabetic mouse. Am Pathol 1990; 136(6):1235-46 and Albertson S, Hummel R P, III, Breeden M, Greenhalgh D G. PDGF and FGF reverse the healing impairment in protein-malnourished diabetic mice.

Surgery 1993; 114(2):368-72), fibroblast growth factor (FGF, acidic or basic) (Broadley K N, et al. Int J Tissue React 1988; 10(6):345-53; Greenhalgh D G, et al. Am J Pathol 1990; 136(6):1235-46; Albertson S, et al. Surgery 1993; 114(2): 368-72; Broadley K N, Aquino A M, Hicks B, Ditesheim J A, McGee G S, Demetriou A A, Woodward S C, Davidson J M. The diabetic rat as an impaired wound healing model: stimulatory effects of transforming growth factor-beta and basic fibroblast growth factor. Biotechnol Ther 1989; 1(1):55-68 and Klingbeil C K, Cesar L B, Fiddes J C. Basic fibroblast growth factor accelerates tissue repair in models of impaired wound healing. Prog Clin Biol Res 1991; 365:443-58, or TGF-β1 (Broadley K N, et al. Int J Tissue React 1988; 10(6): 345-53; Bitar M S, et al. J Surg Res 1996; 61(1): 113-9; Broadley K N, et al. Biotechnol Ther 1989; 1(1):55-68 and Moulin V, Lawny F, Barritault D, Caruelle J P. Platelet releasate treatment improves skin healing in diabetic rats through endogenous growth factor secretion. Cell Mol Biol (Noisy-le-grand) 1998; 44(6):961-71), these results have often not borne fruit when carried to clinical trials of DFU (Richard J L, Parer-Richard C, Daures J P, Clouet S, Vannereau D, Bringer J, Rodier M, Jacob C, Comte-Bardonnet M. Effect of topical basic fibroblast growth factor on the healing of chronic diabetic neuropathic ulcer of the foot. A pilot, randomized, double-blind, placebo-controlled study. Diabetes Care 1995; 18(1):64-9 and Steed D L. Modifying the wound healing response with exogenous growth factors. Clin Plast Surg 1998; 25(3):397-405). Though these therapeutic failures suggest that studies should be carried out on DFU patients and tissue/cells derived from these ulcers, such studies alone are likely insufficient due to the complexity of the wound healing process (Sherratt J A, Dallon J C. Theoretical models of wound healing: past successes and future challenges. C R Biol 2002; 325(5):557-64), the complexity of inflammation from which this process stems Nathan C. Nature 2002; 420 (6917):846-52 and Vodovotz Y, Clermont G, Chow C, An G. Mathematical models of the acute inflammatory response. Curr Opin Crit. Care 2004; 10:383-90), the co-morbidities (Boulton A J, Meneses P, Ennis W J. Diabetic foot ulcers: A framework for prevention and care. Wound Repair Regen 1999; 7(1):7-16 and Consensus Development Conference on Diabetic Foot Wound Care. 7-8 Apr. 1999, Boston, Mass. American Diabetes Association J Am Podiatr Med Assoc 1999; 89(9):475-83) and genetic variability in genes such as TGF-β1 (Bayat A, Bock O, Mrowietz U, Ollier W E, Ferguson M W. Genetic susceptibility to keloid disease and hypertrophic scarring: transforming growth factor beta1 common polymorphisms and plasma levels. Plast Reconstr Surg 2003; 111(2):535-43) in the inflammation/wound healing responses of individual patients. Nonetheless, both systemic and local factors can delay the healing of both acute and chronic wounds and thereby modify their trajectories (Robson M C, Hill D P, Woodske M E, Steed D L. Wound healing trajectories as predictors of effectiveness of therapeutic agents. Arch Surg 2000; 135(7):773-7 and Steed D L. Wound-healing trajectories. Surg Clin North Am 2003; 83(3):547-vii).

As suggested above, mathematical modeling of complex systems is emerging as an approach by which to tame the seemingly unpredictable behavior of such biological phenomena and account for the plethora of known and unknown interactions among biologic pathways (Kitano H. Systems biology: a brief overview. Science 2002; 295(5560): 1662-4), including both acute inflammation (Vodovotz Y, et al. Curr Opin Crit. Care 2004; 10:383-90) and wound healing (Sherratt J A, et al. C R Biol 2002; 325(5):557-64; Murray J D, Maini P K, Tranquillo R. Mechanochemical models for generating biological pattern and form in development. Physics Rep 1988; 171:59-84; Murray J D. Mathematical Biology. Heidelberg (Germany): Springer-Verlag, 1989; Sherratt J A, Murray J D. Models of epidermal wound healing. Proc Biol Sci 1990; 241(1300):29-36; Tranquillo R T, Murray J D. Continuum model of fibroblast-driven wound contraction: inflammation-mediation. J Theor Biol 1992; 158(2):135-72; Tranquillo R T, Murray J D. Mechanistic model of wound contraction. J Surg Res 1993; 55(2):233-47; Cook, J. A mathematical model for dermal wound healing: wound contraction and scar formation. 1995. University of Washington (Seattle); Olsen L, Sherratt J A, Maini P K. A mechanochemical model for adult dermal wound contraction and the permanence of the contracted tissue displacement profile. J Theor Biol 1995; 177(2):113-28; Dallon J C, Sherratt J A, Maini P K. Modeling the effects of transforming growth factor-beta on extracellular matrix alignment in dermal wound repair. Wound Repair Regen 2001; 9(4):278-86; Walker D C, Hill G, Wood S M, Smallwood R H, Southgate J. Agent-based computational modeling of epithelial cell monolayers: predicting the effect of exogenous calcium concentration on the rate of wound closure. IEEE Trans Nanobioscience 2004; 3:153-63 and Walker D C, Southgate J, Hill G, Holcombe M, Hose D R, Wood S M, Mac N S, Smallwood R H. The epitheliome: agent-based modelling of the social behaviour of cells. Biosystems 2004; 76(1-3):89-100). However, these intertwined processes have not been simulated as a cohesive whole in the setting of DFU. Herein, development of an ABM of inflammation and wound healing in the skin is described. This simulation is capable of reproducing qualitatively much of the phenotype of skin wound healing, including changes in relevant cell populations (macrophages, neutrophils, fibroblasts) and, importantly, pro-inflammatory cytokines such as TNF, and anti-inflammatory and pro-healing cytokines such as TGF-β1. The phenotype of DFU is simulated using this ABM, and furthermore, the modulation of PDGF/platelets, debridement, TNF, and TGF-β1 are simulated in the setting of DFU with the goal of suggesting novel therapeutic approaches.

Vocal Fold Injury Phonotrauma and Complexity

Phonotrauma is a common form of vocal fold injury in which inflammation is associated with the risk of tissue injury and subsequently impaired healing. The vocal folds are exposed to nearly continuous biomechanical stress during phonation. Increased intrafold contact stresses associated with certain voicing patterns can result in structural damage to the vocal fold mucosa (Gray, S. et al. (1988). Annals of Otology, Rhinology, and Laryngology, 97(4), 381-388 and Gray, S. D., et al. (2000). Annals of Otology, Rhinology, and Laryngology, 109, 77-85). Specifically, phonotrauma can (1) alter the tissue's physical properties by disrupting intracellular adhesion (Gray, S. et al. (1988). Annals of Otology, Rhinology, and Laryngology, 97(4), 381-388), and (2) modulate the tissue's cellular/molecular responses by altering gene expression (Titze, I. R., Hitchcock, R. W., Broadhead, K., Webb, K., Li, W., Gray, S. D., et al. (2004). Design and validation of a bioreactor for engineering vocal fold tissues under combined tensile and vibrational stresses. Journal of Biomechanics, 37(10), 1521-1529). Persistent stress can lead to further tissue disorganization (Gray, S. D. (1991). Basement membrane zone injury in vocal nodules. San Diego: Singular Press), stimulation of extracellular matrix synthesis (Kim, B. S., Nikolovski, J., Bonadio, J., & Mooney, D. J. (1999). Cyclic mechanical strain regulates the development of engineered smooth muscle tissue. Nature Biotechnology, 17(10), 979-983), and ultimately, to frank phonotraumatic lesions, dysphonia, and quality-of-life changes (Jacobson, B.

H., Johnson, A., Grywalski, C., Silbergleit, A., Jacobson, G., Benninger, M. S., & Newman, C. W. (1997). The voice handicap index (VHI): Development and validation. American Journal of Speech-Language Pathology, 6, 66-70; Ma, E. P., & Yiu, E. M. (2001). Voice activity and participation profile: assessing the impact of voice disorders on daily activities. Journal of Speech, Language, and Hearing Research, 44(3), 511-524; Raaijmakers, M. F., Dekker, J., & Dejonckere, P. H. (1998). Diagnostic assessment and treatment goals in logopedics: impairments, disabilities and handicaps Folia Phoniatr Logop 50(2), 71-79 and Smith, E., Verdolini, K., Gray, S. D., Nichols, S., & Lemke, J. (1996). Effect of voice disorders on quality of life. Journal of Medical Speech Language Pathology, 4, 223-244).

The first-line approach to the treatment of phonotrauma is usually behavioral (Morrison, M., & Rammage, L. (1994). The Management of Voice Disorders. San Diego: Singular Publishing Group Inc.; Stemple, J. C., Lee, L., D'Amico, B., & Pickup, B. (1994). Efficacy of vocal function exercises as a method of improving voice production. Journal of Voice, 8(3), 271-278 and Verdolini, K. (2000). Case Study: Resonant Voice Therapy (2nd ed.). San Diego: Singular Publishing Group Inc). Traditionally, treatment involves complete or partial voice rest (Sataloff, R. T. (1997). Voice rest (2nd ed.). San Diego: Singular Publishing Group, Inc.). However, recent in vitro and human data from laboratories at the University of Pittsburgh, derived from concentrations of inflammatory mediators in laryngeal secretions, suggest that contrary to prevailing clinical wisdom, some forms of vocal tissue mobilization may actually reduce inflammation in acute phonotrauma (Branski R C, Verdolini K, Sandulache V, Rosen C A, Hebda P A. Vocal fold wound healing: A review for clinicians. Journal of Voice; 20(3):432-42 (2006) and Verdolini, K., Li, N. Y. K., Branski, R. C., Rosen, C. A., Urban, E. G., & Hebda, P. A. (in preparation)). The effect of targeted vocal exercise on recovery from acute inflammation). Equally important, both in vitro and human data suggest that the benefits of tissue mobilization for acute vocal fold inflammation are dose-dependent (Branski R C, Verdolini K, Sandulache V, Rosen C A, Hebda P A. Vocal fold wound healing: A review for clinicians. Journal of Voice; 20(3):432-42 (2006)). However, details are lacking about ideal mobilization doses that may optimize healing, and how optimized doses may interact with the specific initial inflammatory status of the tissue. Purely empirical approaches to addressing this question are unattractive because of the relatively invasive and expensive nature of the protocols (Verdolini, K., Li, N.Y. K., Branski, R. C., Rosen, C. A., Urban, E. G., & Hebda, P. A. (in preparation). The effect of targeted vocal exercise on recovery from acute inflammation). The cumbersome nature of data collection also complicates the potential for biologically oriented clinical trials on the value of therapeutic interventions for phonotrauma in humans. However, as can be seen in the schematic of inflammation and wound healing we have used as the guiding principle for our modeling work (FIG. 1), proper healing could be driven by repeated application of sub-threshold stress (the initiating stimulus that would drive both pro- and anti-inflammatory pathways), leading to resolution/wound healing.

The study outlined below in Example 2 is part of an ongoing investigational program at the University of Pittsburgh that addresses these issues. The long-range goal is to generate a technology that will allow clinicians to prescribe an "ideal" vocal exercise (or rest) program that should optimize tissue healing in cases of both acute and chronic phonotrauma (Goldring, S. R. (2003). Calcified Tissue International, 73(2), 97-100; Hart, J. (2002a). Journal of Wound Care, 11(6), 205-209; Hart, J. (2002b). Journal of Wound Care, 11(7), 245-249 and Redd, M. J., et al. (2004). Philosophical Transactions of the Royal Society of London, 359(1445), 777-784). In this way, the previously described goal of regenerative medicine, i.e. to manipulate a patient's tissues in a manner that would lead to their healing (as opposed to administering a drug that corrects the problem) might be achieved. However, phonotrauma is a highly complex process induced by a variety of stimuli, modulated by numerous cells and their products, and affecting different tissues in diverse ways. It is submitted herein that the failure of previous research to integrate information about this complex physiology into a comprehensive framework has hindered the design of optimized clinical treatment plans for phonotrauma. As described above, mathematical modeling of complex systems is a possible avenue to pursue in this light.

A systems biology approach that involves mathematical modeling may prove useful is settings such as phonotrauma, in which it is difficult to obtain statistically sufficient sample sizes for the types of questions asked (Whitcomb, D. C., Aoun, E., Vodovotz, Y., Clermont, G., & Barmada, M. M. (2005). Evaluating disorders with a complex genetics basis. the future roles of meta-analysis and systems biology. Digestive Diseases Sciences, 50(12), 2195-2202).

Preliminary Studies on Quantification of Vocal Fold Inflammation in Phonotrauma

Mathematical models of complex systems require empirical inputs, which are then subjected to various rules that dictate the system's future behavior. Prerequisite to the empirical endeavor relevant to modeling of inflammation is a methodology for obtaining quantitative data about inflammatory mediators in the tissue of interest. Four studies have been published on the development of a novel marginally-invasive method for obtaining quantitative information about the inflammatory status of the larynx from laryngeal secretions. Laryngeal secretions may be obtained as follows: Subjects will first receive 4% lidocaine hydrochloride totaling approximately 3 mL administered to the larynx, using one channel of a dual-channel chip-tip laryngoscope, until vocal fold insensitivity to light touch with the scope is achieved. Tubing in the second channel of the chip-tip scope will then be attached to a wall suction source for extraction of approximately 3 mL of secretions from medial and superior vocal fold surfaces bilaterally. Secretions will be immediately stored at −80° C. for later analysis.

The first study (Verdolini, K., Rosen, C. A., Branski, R. C., & Hebda, P. A. (2003). Shifts in biochemical markers associated with wound healing in laryngeal secretions following phonotrauma: A preliminary study. Annals of Otology, Rhinology, & Laryngology, 112(12), 1021-1025) sampled secretions from the vocal fold surfaces of an adult female before and after one hour of vocal loading. Samples were subjected to Enzyme-Linked Immunosorbent Assays (ELISAs) for IL-1$\beta$, TGF-$\beta$1, TNF-$\alpha$, PGE$_2$ and matrix metalloproteinase-8 (MMP-8). The results showed that pre- to post-loading shifts in mediator concentrations were clearly evident at 10 and 20 min post-loading for IL-$\beta$, TNF-$\alpha$, and MMP-8, reflecting the presence of acute phonotrauma. In contrast, concentration shifts were not shown for TGF-$\beta$1 or PGE$_2$.

Another intraoperative human study used the same methodology to look at the inflammatory profile for chronic phonotrauma versus acute inflammatory disease (papilloma and epithelial cancer), and confirmed that IL1-$\beta$ was an indicator of acute inflammation, whereas PGE$_2$ characterized chronic wounds (Branski, R. C., Verdolini, K., Rosen, C. A., & Hebda, P. A. (2004). Markers of wound healing in vocal fold secretions from patients with laryngeal pathology. Annals of Otology, Rhinology, and Laryngology, 113(1), 23-29).

A third study used a rabbit surgical trauma model to assess fluctuations in inflammatory profiles from laryngeal secretions over a 3-week pre-post surgical time period. Again, IL1-β was shown to be an early indicator of inflammation, and $PGE_2$ was a later indicator of wound healing (Branski, R. C., Rosen, C. A., Verdolini, K., & Hebda, P. A. (2005b). Biochemical markers associated with acute vocal fold wound healing: a rabbit model. Journal of Voice, 19(2), 283-289). That is, both mediators were increased 24 hour after injury. However, the initial IL1-β spike was greater, and values resolved to baseline by Day 7 post-injury. In contrast, $PGE_2$ concentrations increased gradually from Day 1 to Day 7, and stayed high until the final data collection point at 3-week post-injury follow-up.

Finally, a fourth study assessed the degree to which assays of laryngeal secretions may reflect wound healing processes deep to the epithelium (Branski, R. C., Rosen, C. A., Verdolini, K., & Hebda, P. A. (2005a). Acute vocal fold wound healing in a rabbit model. Annals of Otology, Rhinology, and Laryngology, 114(1 Pt 1), 19-24). That study, which used the same surgical rabbit model, showed that the time point associated with spikes in IL1-β (24 hour) corresponded to the presence of fibrinous clot. The time point associated with maximum $PGE_2$ levels (7 days) was associated with the presence of mature collagen. Massive cellular infiltration and complete epithelial coverage were found at intermediate time points.

Taken together, the four studies provide robust evidence that secretions from the laryngeal surfaces can provide a quantitative window into the current inflammatory and wound healing state of vocal fold tissue. The attractiveness of the marginally invasive technology is that it can be readily used in human subjects—although not without some difficulties on the part of both subjects and examiners—and thus the data gain external validity over data obtained from more invasive technologies involving animal subjects. In the context of the present disclosure, the modeling approach of interest for the vocal-fold study involves Agent-Based Models (ABMs), as discussed above.

Necrotizing Enterocolitis

Necrotizing enterocolitis (NEC) is a medical condition primarily seen in premature infants in which portions of the bowel necrotize, a process which is characterized by deranged inflammation and impaired intestinal healing. The condition is typically seen within days after birth and initial symptoms include feeding intolerance, abdominal distension and bloody stools. Symptoms may progress rapidly to abdominal discoloration with intestinal perforation and peritonitis and systemic hypotension requiring intensive medical support. NEC has no definitive known cause. A contagious agent is suspected, because cluster outbreaks in neonatal intensive care units (NICUs) are seen, but it is suspected that a combination of contagion, inherent weakness in the bowel, and timing of the initiation of oral feedings are factors. NEC is almost never seen in infants before oral feedings are initiated. Treatment of NEC is medical or surgical. Initial medical treatment includes bowel rest and decompression with intermittent gastric suction. Immediate treatment with intravenous antibiotics is indicated. The deteriorating bowel can be visualized on X-ray as pneumatosis intestinalis. If the disease is not halted through medical treatment alone, or if the bowel perforates, immediate emergency surgery is required to resect the dead bowel. This may require a colostomy, which may be able to be reversed at a later time. Some children may suffer later as a result of short bowel syndrome if extensive portions of the bowel had to be removed (Upperman, J. S.; Lugo, B.; Camerini, V.; Yotov; I.; Rubin, J.; Clermont, G.; Zamora, R.; Ermentrout, G. B.; Ford, H. R.; Vodovotz, Y.; Mathematical Modeling in NEC—A New Look at an Ongoing Problem. J. Pediatr. Res., 2007. 42:445-453). Because the inflammatory process plays a significant role in necrotizing enterocolitis, the modeling systems described herein are applicable to this biological system. Using partial differential equations, the basic processes of NEC were modeled, reproducing many of the features of this disease outlined above (Upperman, J. S.; Lugo, B.; Camerini, V.; Yotov; I.; Rubin, J.; Clermont, G.; Zamora, R.; Ermentrout, G. B.; Ford, H. R.; Vodovotz, Y.; Mathematical Modeling in NEC—A New Look at an Ongoing Problem. J. Pediatr. Res., 2007. 42:445-453).

The indigenous intestinal microbial flora is postulated to play a central role in the pathogenesis of NEC. In fact, bacterial colonization may be a pre-requisite for the development of NEC (Peter C S, Feuerhahn M, Bohnhorst B, Schlaud M, Ziesing S, von der Hardt H, Poets C F. Necrotising enterocolitis: is there a relationship to specific pathogens? Eur J Pediatr 1999; 158:67-70) because oral prophylaxis with vancomycin or gentamycin was shown to reduce the incidence of NEC (Fast C, Rosegger H. Necrotizing enterocolitis prophylaxis: oral antibiotics and lyophilized enterobacteria vs oral immunoglobulins [see comments]. Acta Paediatr Suppl 1994; 396:86-90). Common bacterial isolates from blood, peritoneal, and stool cultures from infants with advanced NEC include *Escherichia coli, Enterobacter*, and *Klebsiella* species, and occasionally, coagulase-negative *Staphylococcus* species (Fast C, Rosegger H. Necrotizing enterocolitis prophylaxis: oral antibiotics and lyophilized enterobacteria vs oral immunoglobulins. Acta Paediatr Suppl 1994; 396:86-90). Recent preliminary reports tout the success of probiotic therapy in preventing NEC (Lin H C, Su B H, Chen A C, Lin T W, Tsai C H, Yeh T F, Oh W. Oral probiotics reduce the incidence and severity of necrotizing enterocolitis in very low birth weight infants. Pediatrics 2005; 115:1-4), thus affirming our belief that microbes play a role in exacerbating inflammation. As we shall describe below, NEC typically develops after two weeks in premature infants coinciding with the colonization of the gastrointestinal tract with gram negative and other bacteria (Krediet T G, van Lelyveld N, Vijlbrief D C, Brouwers H A, Kramer W L, Fleer A, Gerards U. Microbiological factors associated with neonatal necrotizing enterocolitis: protective effect of early antibiotic treatment. Acta Paediatr 2003; 92:1180-2).

Inflammatory Mediators in Necrotizing Enterocolitis.

Various pro-inflammatory cytokines and products of vasoactive substances are present in the serum and intestine of infants with NEC, including tumor necrosis factor (TNF)-α, interleukin (IL)-1, IL-6, IL-8, IL-10, IL-11, platelet-activating factor (PAF), and nitric oxide (NO) (Upperman, J S, Potoka, D, Grishin, A, et al: Mechanisms of nitric oxide-mediated intestinal barrier failure in necrotizing enterocolitis. Semin Pediatr Surg, 2005; 14(3): p. 159-66; Ren, Y, Lin, C L, Li, Z, et al: Up-regulation of macrophage migration inhibitory factor in infants with acute neonatal necrotizing enterocolitis. Histopathology, 2005; 46(6): p. 659-67; Harris, M C, D'Angio, C T, Gallagher, P R, et al: Cytokine elaboration in critically ill infants with bacterial sepsis, necrotizing enterocolitis, or sepsis syndrome: correlation with clinical parameters of inflammation and mortality. J Pediatr, 2005; 147(4): p. 462-8; McCloy, M P, Roberts, I A, Howarth, U, et al: Interleukin-11 levels in healthy and thrombocytopenic neonates. Pediatr Res, 2002; 51(6): p. 756-60; Nadler, E P, Dickinson, E, Knisely, A, et al: Expression of inducible nitric oxide synthase and interleukin-12 in experimental necrotizing enterocolitis. J Surg Res, 2000; 92(1): p. 71-7; Ford, H R, Sorrells, D L Knisely, A S: Inflammatory cytokines, nitric oxide, and necrotizing enterocolitis. Semin Pediatr Surg, 1996; 5(3): p. 155-9; Muguruma, K, Gray, P W, Tjoelker, L W, et al: The central role of PAF in necrotizing enterocolitis development. Advances in Experimental Medicine & Biology, 1997; 407: p. 379-82; Lauterbach, R, Pawlik, D, Kowalczyk, D, et al: Effect of the immunomodulating agent, pentoxifylline, in the treatment of sepsis in prematurely delivered infants: a placebo-controlled, double-blind trial [see comments]. Crit. Care Med, 1999; 27(4): p. 807-14 and Edelson, M B, Bagwell, CE Rozycki, H J: Circulating pro- and counter-inflammatory cytokine levels and severity in necrotizing enterocolitis. Pediatrics, 1999; 103(4 Pt 1): p. 766-71). The significance and prognostic value of individual abnormalities in one or more of these substances is however, unclear. Elevated plasma levels of TNF-α have been reported in infants with NEC (Lauterbach, R, Pawlik, D, Kowalczyk, D, et al: Effect of the immunomodulating agent, pentoxifylline, in the treatment of sepsis in prematurely delivered infants: a placebo-controlled, double-blind trial [see comments]. Crit. Care Med, 1999; 27(4): p. 807-14; Caplan, M S, Sun, X M, Hseuh, W, et al: Role of platelet activating factor and tumor necrosis factor-alpha in neonatal necrotizing enterocolitis. J Pediatr, 1990; 116(6): p. 960-4 and Lauterbach, R Zembala, M: Pentoxifylline reduces plasma tumour necrosis factor-alpha concentration in premature infants with sepsis. Eur J Pediatr, 1996; 155(5): p. 404-9). Clinical trials demonstrate that pentoxifylline, which blocks TNF-α and IL-6 production, may provide a survival benefit in acute NEC (Lauterbach, R, Pawlik, D, Kowalczyk, D, et al: Effect of the immunomodulating agent, pentoxifylline, in the treatment of sepsis in prematurely delivered infants: a placebo-controlled, double-blind trial [see comments]. Crit. Care Med, 1999; 27(4): p. 807-14 and Lauterbach, R Zembala, M: Pentoxifylline reduces plasma tumour necrosis factor-alpha concentration in premature infants with sepsis. Eur J Pediatr, 1996; 155(5): p. 404-9). Other investigators, however, have been unable to detect any significant increase in plasma TNF-α levels in infants with NEC (Harris, M C, Costarino, A T, Jr., Sullivan, J S, et al: Cytokine elevations in critically ill infants with sepsis and necrotizing enterocolitis [see comments]. J Pediatr, 1994; 124(1): p. 105-11). In fact, plasma TNF-α levels do not seem to correlate with either the severity or the duration of disease (Morecroft, J A, Spitz, L, Hamilton, P A, et al: Plasma interleukin-6 and tumour necrosis factor levels as predictors of disease severity and outcome in necrotizing enterocolitis. J Pediatr Surg, 1994; 29(6): p. 798-800). Similar controversies regarding the presence and role of other proinflammatory cytokines in NEC including. IL-1, a cytokine released early during an inflammatory response. In infants with NEC, plasma levels of IL-1 are initially elevated, although the IL-1 receptor antagonist (IL-1RA), the endogenous inhibitor of IL-1 may be a better correlate of disease severity (Caplan, M S, Sun, X M, Hseuh, W, et al: Role of platelet activating factor and tumor necrosis factor-alpha in neonatal necrotizing enterocolitis. J Pediatr, 1990; 116(6): p. 960-4). Similarly, while serum levels of IL-6 correlate with disease severity (Lauterbach, R, Pawlik, D, Kowalczyk, D, et al: Effect of the immunomodulating agent, pentoxifylline, in the treatment of sepsis in prematurely delivered infants: a placebo-controlled, double-blind trial [see comments]. Crit. Care Med, 1999; 27(4): p. 807-14; Morecroft, J A, Spitz, L, Hamilton, P A, et al: Plasma interleukin-6 and tumour necrosis factor levels as predictors of disease severity and outcome in necrotizing enterocolitis. J Pediatr Surg, 1994; 29(6): p. 798-800 and Morecroft, J A, Spitz, L, Hamilton, P A, et al: Plasma cytokine levels in necrotizing enterocolitis. Acta Paediatr Suppl, 1994; 396: p. 18-20) no difference in intestinal IL-6 mRNA or protein was found in infants with advanced NEC and age-matched controls (Viscardi, R M, Lyon, N H, Sun, C C, et al: Inflammatory cytokine mRNAs in surgical specimens of necrotizing enterocolitis and normal newborn intestine. Pediatr Pathol Lab Med, 1997; 17(4): p. 547-59 and Ford, H, Watkins, S, Reblock, K, et al: The role of inflammatory cytokines and nitric oxide in the pathogenesis of necrotizing enterocolitis. Journal of Pediatric Surgery., 1997; 32(2): p. 275-82). A similar controversy was found with IL-8, a potent chemotactic factor for neutrophils while serum levels of IL-8 were increased in infants with severe NEC (Edelson, M B, Bagwell, CE Rozycki, H J: Circulating pro- and counterinflammatory cytokine levels and severity in necrotizing enterocolitis. Pediatrics, 1999; 103(4 Pt 1): p. 766-71) no difference in IL-8 mRNA or protein in diseased intestine was detected in infants with acute NEC (Viscardi, R M, Lyon, N H, Sun, C C, et al: Inflammatory cytokine mRNAs in surgical specimens of necrotizing enterocolitis and normal newborn intestine. Pediatr Pathol Lab Med, 1997; 17(4): p. 547-59). Whereas others have detected increased levels of IL-8, along with IL-11, and IFN-γ mRNA in intestinal specimens from infants with acute NEC as compared to controls. (Ford, H, Watkins, S, Reblock, K, et al: The role of inflammatory cytokines and nitric oxide in the pathogenesis of necrotizing enterocolitis. Journal of Pediatric Surgery., 1997; 32(2): p. 275-82 and Nadler, E, Stanford, A, Zhang, X, et al: Intestinal cytokine gene expression in infants with acute NEC: IL-11 mRNA expression inversely correlates with extent of disease. J Ped Surg, 2001; 36(8): p. 1122-29). Serial plasma levels of IL-6 and IL-10 were elevated among premature infants with NEC among those with suspected sepsis hours after clinical signs of sepsis were detected (Romagnoli, C, Frezza, S, Cingolani, A, et al: Plasma levels of interleukin-6 and interleukin-10 in preterm neonates evaluated for sepsis. Eur J Pediatr, 2001; 160(6): p. 345-50). A similar study found serial elevations in IL-8, IL-1RA and IL-10 with levels whose increase correlated with the severity of disease and the need for surgical intervention (Edelson, M B, Bagwell, C E, Rozycki, H J: Circulating pro- and counter-inflammatory cytokine levels and severity in necrotizing enterocolitis. Pediatrics, 1999; 103(4 Pt 1): p. 766-71). Plasma levels of other products of proinflammatory mediators also exhibit variability in NEC. Platelet activating factor (PAF), a pro-inflammatory lipid mediator shown to directly cause intestinal mucosal injury and bowel necrosis in animal models of NEC (Caplan, M S, Kelly, A H such, W: Endotoxin and hypoxia-induced intestinal necrosis in rats: the role of platelet activating factor. Pediatr Res, 1992; 31(5): p. 428-34 and Caplan, M S, Sun, X M Hsuch, W: Hypoxia causes ischemic bowel necrosis in rats: the role of platelet-activating factor (PAF-acether). Gastroenterology, 1990; 99(4): p. 979-86) was elevated in neonates with NEC compared to age-matched controls (Caplan, M S, Sun, X M, Hseuh, W, et al: Role of platelet activating factor and tumor necrosis factor-alpha in neonatal necrotizing enterocolitis. J Pediatr, 1990; 116(6): p. 960-4). Likewise, PAF-acetylhydrolase activity, responsible for the generation of PAF, was reciprocally decreased in infants with NEC. Increased levels of TNF-α may in addition result in increases in PAF production although a PAF-antagonist failed to limit the extent of mucosal injury in an ischemia/reperfusion model, suggesting that PAF alone is not sufficient to cause ischemic injury to the gut (de Boissieu, D, Canarelli, J P, Cordonnier, C, et al: Effect of BN 50727 on pathological findings and tissue platelet activating factor levels during ileal ischemia in newborn piglets. J Pediatr Surg, 1996; 31(12): p. 1675-9).

A challenge in NEC, as well as other tissue-specific inflammatory conditions, is in understanding the significance of pro-inflammatory mediators in the tissue as compared to those in serum or plasma. One possible explanation for the lack of unity in published studies is the high degree of variability among individual cases of NEC. However, we believe that the kinetics of cytokine production are highly dependent on patient-specific conditions (Chow, C C, Clermont, G, Kumar, R, et al: The acute inflammatory response in diverse shock states. Shock, 2005; 24(1): p. 74-84), and fluctuations from an individual baseline are likely to yield important insight into the onset and progression of disease.

The foregoing discussion suggests that much data, but relatively few therapeutically useful insights, have been obtained over the past years of research on human and experimental NEC. This situation mirrors that of the sepsis and trauma fields. We reasoned that to break this logjam, we should begin to employ approaches that treat NEC as a system, rather than an isolated set of parts (Csete, M E Doyle, J C: Reverse engineering of biological complexity. Science, 2002; 295(5560): p. 1664-9). Recently, it has been suggested that statistically-based methods may not achieve full usefulness in complex inflammatory diseases such as NEC because these methods require large amounts of data; in contrast, techniques such as mathematical modeling can derive insights from relatively small datasets such as those likely to be obtained from neonates (Whitcomb, D C, Aoun, E, Vodovotz, Y, et al: Evaluating disorders with a complex genetics basis. the future roles of meta-analysis and systems biology. Dig Dis Sci, 2005; 50(12): p. 2195-202). Below, we describe our mathematical modeling approach and the strides we have made in bringing this technology closer to practical application in the setting of NEC.

Like ulcerative colitis, inflammatory bowel diseases such as Crohn's Disease and Ulcerative colitis have tissue injury, inflammatory and healing components and are amenable to simulation according to the methods described herein.

Restenosis

Restenosis literally means the reoccurrence of stenosis (an abnormal narrowing in a blood vessel or other tubular organ or structure). In the context of the present disclosure, restenosis refers to narrowing of an artery, typically a coronary artery. Restenosis is common in vascular surgery, cardiac surgery, interventional radiology, or interventional cardiology following angioplasty after treatment of stenotic lesions. There are probably several mechanisms that lead to restenosis. An important one is the inflammatory response, which induces tissue proliferation around an angioplasty site. Many approaches have been tried to decrease the risk of restenosis. Stenting is commonplace after balloon angioplasty. Other approaches include local radiotherapy and the use of immunosuppressive drugs, typically coated onto the stenting mesh or delivered via specialized balloon catheters. Analogues of rapamycin, such as tacrolimus (FK-506), sirolimus and everolimus, normally used as immunosuppressants but recently discovered to also inhibit the proliferation of vascular smooth muscle cells, have appeared to be quite effective in preventing restenosis in clinical trials. Antisense knockdown of c-myc, a protein critical for progression of cell replication, is another approach to inhibit cell proliferation and is undergoing clinical trials in Europe using Morpholino oligonucleotides. Because the process of inflammation and wound healing plays a significant role in restenosis, the modeling systems described herein are applicable to this biological system. Importantly, some of the anti-restenotic modalities described (e.g. local radiotherapy) above at times disrupt healing and cause inflammation while reducing restenosis. This aberrant healing is generally associated with elevated thrombosis and the need for long-term treatment with anti-coagulants (R. Waksman. Late thrombosis after radiation: Sitting on a time bomb. Circulation. 100:780-782, 1999; Vodovotz, Y.; Waksman, R.; Kim, W. H.; Bhargava, B.; Chan, R. C.; Leon, M. Effects of intracoronary radiation on thrombosis following balloon injury in the porcine model. Circulation. 1999; 100:2527-2533).

EXAMPLE 1

Diabetic Skin Ulcers

ABM models can simulate the behavior of complex systems in which agents interact with each other and with their environment following local rules based on known physiology. Moreover, the ABM framework accounts for the stochastic nature of biological processes, in that each rule is a probability of a given event happening; thus, each simulation leads to a unique outcome and can be considered as a separate experiment (or "virtual patient") (Vodovotz Y, et al. Curr Opin Crit. Care 2004; 10:383-90). A typical ABM model includes three types of elements: region, patch and agent. The region consists of small patches that are uniquely characterized by spatial position, and contain local information. Agents are the objects that can move in the region. The motion of all agents is due to both chemoattraction and stochastic walk, as described in greater detail below.

Herein, an ABM is designed to simulate inflammation and wound healing in a physical domain including skin and underlying soft tissue (the tissue), using Netlogo® software (Center for Connected Learning and Computer-Based Modeling, Northwestern University, Evanston, I L, see also, for example, NetLogo® 3.1.2 Users Manual). First, two regions were created to simulate blood (the source of some of the inflammatory cells that infiltrate injured tissue) and the tissue itself (which contains some inflammatory cells as well as the fibroblasts that will eventually act to heal the injured tissue). The two regions (blood and tissue) do not intersect: the tissue region is circular and surrounded by the blood region. Different agents were used to represent the damage (induced by the initial injury as well as by subsequent inflammation, and also a stimulus for further inflammation), as well as resting and activated inflammatory cells (neutrophils, macrophages and fibroblasts). Patch variables (Annes J P, Munger J S, Rifkin D B. Making sense of latent TGFbeta activation. J Cell Sci 2003; 116(Pt 2):217-24 and Zamora R, Vodovotz Y. Transforming Growth Factor-b in Critical Illness. Crit. Care Med 2005; 33:S478-S481 also were used to represent latent TGF-$\beta$1 and the mediators produced by these cells during the inflammation and wound healing stages. The mediators include the pro-inflammatory cytokines IL-$\beta$1 and TNF (both produced by neutrophils and macrophages); the anti-inflammatory cytokines TGF-$\beta$1 and IL-10 (both produced by macrophages); and collagen (produced by fibroblasts) (Martin P. Wound healing—aiming for perfect skin regeneration. Science 1997; 276(5309):75-81; Witte M B, Barbul A. General principles of wound healing. Surg Clin North Am 1997; 77(3):509-28 and Cockbill S. Wounds: The healing process. Hosp Pharmacist 2002; 9:255-60.

Initially, some resting macrophages, neutrophils, fibroblasts and latent TGF-$\beta$1 are present with a random distribution both in tissue and blood. By stimulating the tissue with damage in the middle of region, the model creates a chemoattractant gradient (induced by platelet degranulation) Witte M B, et al. Surg Clin North Am 1997; 77(3):509-28 and Robson M C, Steed D L, Franz M G. Wound healing: biologic features and approaches to maximize healing trajectories. Curr Probl Surg 2001; 38(2):72-140), which acts to induce the infiltration and activation of both neutrophils and macrophages. Fibroblasts are activated at a later stage both by damage and TGF-β1, to produce collagen that acts to repair both the initial and inflammation-induced damage (Martin P. Science 1997; 276(5309):75-81; Witte M B, Barbul A. General principles of wound healing. Surg Clin North Am 1997; 77(3):509-28 and Robson M C, Steed D L, Franz M G. Wound healing: biologic features and approaches to maximize healing trajectories. Curr Probl Surg 2001; 38(2):72-140).

ABM Rules

The following are rules created for the present example created in NetLogo®.

Time scale. It was assumed in the model that 1 unit of simulated time represents 0.069 day. This assumption results in complete healing (defined as return of the damage variable to baseline) in the normal scenario by ~30 days. All of the dynamics of cells and cytokines are therefore appropriately scaled to give realistic time courses.

Lifespans and Half-lives. The lifespan was assumed to be 1-3 days for neutrophils, 4-6 days for macrophages and 5-7 days for fibroblasts. Cytokine half-lives were assumed to be 2-3 days. We note the half life of latent TGF-β1 is much larger than the half life of activated TGF-β1 (O'Connor-McCourt M D, Wakefield L M. Latent transforming growth factor-β in serum: A specific complex with α2-macroglobulin. J Biol Chem 1987; 262:14090-9).

Initialization. The total number of resting neutrophils and macrophages were arbitrarily set to 80 each, and the number of resting fibroblasts was set to 30. The location and age of these cells was randomly distributed in both blood and tissue. The initial total amount of damage was set to M*M, where M is a number set by the user. In the simulations, M was set to 16. This damage was randomly distributed inside the disk centered at the origin of the domain and with diameter equal to M. The initial number of platelets p(x,y) was spatially distributed according to the formula $(100/(1+x^2+y^2))$, where (x,y) are coordinates of the platelet position. This type of distribution for the platelets is crucial for the initialization of the inflammatory process. The initial values of IL-1β, TNF, activated TGF-β1, IL-10, and collagen were set to zero. The initial amount of latent TGF-β1 was set to 10.

Activation. (In this simulation, neutrophils and macrophage are chemoattracted by platelets as well as TNF while fibroblasts are chemoattracted by TGF-β1 (Cockbill S. Wounds: The healing process. Hosp Pharmacist 2002; 9:255-60). In actuality, platelets release several growth factors in addition to TGF-β1, such as PDGF, transforming growth factors α (TGF-α), epidermal growth factor (EGF), and insulin-like growth factor-I (IGF-I) to activate macrophages and neutrophils (Cockbill S. Wounds: The healing process. Hosp Pharmacist 2002; 9:255-60). However, in our model we do not include all of these growth factors, but rather assume, for simplicity, that platelets can activate those inflammatory cells in the following way: Macrophages are activated by platelets if the number of platelets is greater than 100/(1+M*M), where M represents the magnitude of the damage, and are activated by TNF if TNF>0.1. Neutrophils are activated by platelets if the number of platelets is greater than 100/(1+M*1.7)*(M*1.7), where M represents the magnitude of the damage, and are activated by TNF if TNF>0.2. Fibroblasts are activated by TGF-β1 if TGF-β1>0.2 and damage is present.

Cell Motion: Chemoattraction and Stochastic Motion

The motion of all agents is due to both chemoattraction and stochastic walk. first, neutrophils and macrophage are chemoattracted by platelets as well as TNF while fibroblasts are chemoattracted by TGF-β1 (Walker D C, Hill G, Wood S M, Smallwood R H, Southgate J. Agent-based computational modeling of epithelial cell monolayers: predicting the effect of exogenous calcium concentration on the rate of wound closure. IEEE Trans Nanobioscience 2004; 3:153-63). Second, every unit time, the direction of cells is randomly changed.

Mediators

1.TNF:

Produced by activated macrophages and activated neutrophils. Inhibited by TGF-β1 and IL-10 and elevated by TNF and IL1-β (Cockbill S. Wounds: The healing process. Hosp Pharmacist 2002; 9:255-60; Krishnamoorthy L, Morris H L, Harding K G. Specific growth factors and the healing of chronic wounds. J Wound Care 2001; 10(5):173-8; Bennett S P, Griffiths G D, Schor A M, Leese G P, Schor S L. Growth factors in the treatment of diabetic foot ulcers. Br J Surg 2003; 90(2): 133-46 and O'Connor-McCourt M D, Wakefield L M. Latent transforming growth factor-β in serum: A specific complex with α2-macroglobulin. J Biol Chem 1987; 262: 14090-9). In the TNF-overproducing simulation, for activated macrophages, the dynamics of TNF are calculated by the equation: TNF=TNF+0.044*(1/(0.1+TGF*100+IL-10/100))*(1+TNF+IL1-beta/10))). For activated neutrophils, the dynamics of TNF are calculated by the equation: TNF=TNF+2.2*(1/(0.1+TGF*100+IL-10/100))*(1+TNF+IL1-beta/10))). In the simulation of TNF-overproducing with anti-TNF antibody treatment, for activated macrophages, these dynamics are calculated by the equation: TNF=TNF+0.0293*(1/(0.1+TGF*100+IL-10/100))*(1+TNF+IL1-beta/10))). For activated neutrophils, these dynamics are calculated by the equation: TNF=TNF+1.467*(1/(0.1+TGF*100+IL-10/100))* (1+TNF+IL1-beta/10))). In the simulation of TGF-β1-under-production with anti-TNF antibody treatment, for activated macrophages, these dynamics are calculated by the equation: TNF=TNF+0.0067*(1/(0.1+TGF*100+IL-10/100))*(1+TNF+IL1-beta/10))). For activated neutrophils, these dynamics are calculated by the equation: TNF=TNF+0.33*(1/(0.1+TGF*100+IL-10/100))*(1+TNF+IL1-beta/10))). In the other simulations, for activated macrophages, these dynamics are calculated by the equation: TNF=TNF+0.02*(1/(0.1+TGF*100+IL-10/100))*(1+TNF+IL1-beta/10))). For activated neutrophils, these dynamics are calculated by the equation: TNF=TNF+(1/(0.1+TGF*100+IL-10/100))*(1+TNF+IL1-beta/10))).

Biological function: Inhibit the expression of TGF-β1 and IL-10 in activated macrophages. Stimulate the expression of TNF and IL-1β in activated macrophages and neutrophils. Activate latent TGF-β1, macrophages, and neutrophils.

TNF diffuses in the following sense: periodically (every 0.1 unit time) each patch shares 100 percent of the value of the patch with its 8 neighboring patches.

2.TGF-β1:

Activated from latent-TGF-β1 by TNF and IL1-β: if TNF>0.2 or IL1-β>0.2, then TGF=TGF+latent-TGF*0.001; latent-TGF=latent-TGF*0.999. In the simulations of latent-TGF treatment, the initial value of latent-TGF equals four. In the other simulations, the initial value of latent-TGF equals one.

Produced by activated macrophages and activated fibroblasts. Inhibited by TNF. In the simulations of TGF-β1-under-production, for activated macrophages, TGF-β1 dynamics are calculated by the equation: TGF=TGF+latent- TGF*0.03/(1+TNF*10). For activated fibroblasts, these dynamics are calculated by the equation: TGF=TGF+0.015/(1+TNF/5). In the simulations of TGF-β1-under-production with TGF-β1 activation treatment, for activated macrophages, TGF-β1 dynamics are calculated by the equation: TGF=TGF+latent-TGF*0.15/(1+TNF*10). For activated fibroblasts, these dynamics are calculated by the equation: TGF=TGF+0.075/(1+TNF/5). In the simulations of TNF-overproducing with TGF-β1 activation treatment, for activated macrophages, TGF-β1 dynamics are calculated by the equation: TGF=TGF+latent-TGF/(1+TNF*10). For activated fibroblasts, these dynamics are calculated by the equation: TGF=TGF+0.5/(1+TNF/5). In the other simulations, for activated macrophages, these dynamics are calculated by the equation: TGF=TGF+latent-TGF*0.2/(1+TNF*10). For activated neutrophils, these dynamics are calculated by the equation: TGF=TGF+0.1/(1+TNF/5).

Biological function: Inhibit expression of TNF and IL-1β in activated macrophages and neutrophils; chemoattract and activate fibroblasts (Annes J P, Munger J S, Rifkin D B. Making sense of latent TGFbeta activation. J Cell Sci 2003; 116(Pt 2):217-24; Zamora R, Vodovotz Y. Transforming Growth Factor-β1 in Critical Illness. Crit. Care Med 2005; 33:S478-S481 and Witte M B, Barbul A. General principles of wound healing. Surg Clin North Am 1997; 77(3):509-28).

TGF-β1 diffuses in the following sense: periodically (every 0.1 s) each patch shares 100 percent of the value of the patch with its 8 neighboring patches.

3.IL-1β:

Produced by activated macrophage and neutrophils. Inhibited by TGF-β1 and IL-10. Elevated by TNF and IL1-β. The dynamics of IL-1β are calculated by the equation: IL1-beta=IL1-beta+0.2/(1+TGF*2+IL-10/100)*(1+TNF+IL1-beta).

Biological function: Simulate TNF and IL-1β expression in activated macrophages and neutrophils. Increase TGF-β1 activation (Flaumenhaft R, Kojima S, Abe M, Rifkin D B. Activation of latent transforming growth factor β. Advances in Pharmacology 1993; 24:51-76; An G. Agent-based computer simulation and SIRS: building a bridge between basic science and clinical trials. Shock 2001; 16(4):266-73; Annes J P, Munger J S, Rifkin D B. Making sense of latent TGFbeta activation. J Cell Sci 2003; 116(Pt 2):217-24; Zamora R, Vodovotz Y. Transforming Growth Factor-β in Critical Illness. Crit Care Med 2005; 33:S478-S481; Martin P. Wound healing—aiming for perfect skin regeneration. Science 1997; 276(5309):75-81 and Witte M B, Barbul A. General principles of wound healing. Surg Clin North Am 1997; 77(3):509-28).

IL-1β diffuses in the following sense: periodically (every 0.1 s) each patch shares 100 percent of the value of the patch with its 8 neighboring patches

4.IL-10:

Produced by activated macrophages. The dynamics of IL-10 are calculated by the equation: IL1-10=IL1-10+1.

Biological function: Inhibit TNF (Wahl S M, McCartney-Francis N, Mergenhagen S E. Inflammatory and immunomodulatory roles of TGF-Beta. Immunol Today 1989; 10:258-61; O'Connor-McCourt M D, Wakefield L M. Latent transforming growth factor-β in serum: A specific complex with α2-macroglobulin. J Biol Chem 1987; 262:14090-9 and Bogdan C, Vodovotz Y, Nathan C F. Macrophage deactivation by interleukin 10. J Exp Med 1991; 174:1549-55) and IL-1β (Wahl S M, McCartney-Francis N, Mergenhagen S E. Inflammatory and immunomodulatory roles of TGF-Beta. Immunol Today 1989; 10:258-61 and Bogdan C, Vodovotz Y, Nathan C F. Macrophage deactivation by interleukin 10. J Exp Med 1991; 174:1549-55) expression in activated macrophages and neutrophils.

IL-10 diffuses in the following sense: periodically (every 0.1 unit time) each patch shares 100 percent of the value of the patch with its 8 neighboring patches.

5.Collagen:

Produced by activated fibroblasts. Inhibited by TNF and elevated by TGF-β1. In our model, we also required that the amount of collagen produced not exceed the existing amount of damage in the same patch. Collagen dynamics are calculated by the equation: (if damage >2*total-TGF/(1+total-TNF), collagen=collagen+2*total-TGF/(1+total-TNF)) else collagen=collagen+damage).

Biological function: tissue repair (Annes J P, Munger J S, Rifkin D B. Making sense of latent TGFbeta activation. J Cell Sci 2003; 116(Pt 2):217-24; Zamora R, Vodovotz Y. Transforming Growth Factor-β in Critical Illness. Crit. Care Med 2005; 33:S478-S481; Martin P. Wound healing—aiming for perfect skin regeneration. Science 1997; 276(5309):75-81 and Witte M B, Barbul A. General principles of wound healing. Surg Clin North Am 1997; 77(3):509-28).

Source Terms

In the simulation, there are damage-dependent sources for resting macrophages and resting neutrophils randomly distributed in the tissue and blood. The number of newly created neutrophils is a function of the total amount A of damage: 2*(A/1500+1) every 0.5 time units until 2.7 days of simulated time are reached. The number of newly created macrophages is a function of the total amount A of damage: A/15000+1 every 2 time units until 20 days of simulated time are reached. There is also a constant source (two cells per every four time units) of resting fibroblasts randomly distributed in the tissue and blood if damage exists.

Damage: In addition to initial damage, damage can also be created by TNF if TNF>0.25. Damage is healed by collagen (if collagen>0. damage=damage−1.collagen=collagen−1), and it also has 0.2% chance for self-healing every time unit.

Other Functions

The movements of neutrophils, macrophages, and fibroblasts are random walks based on chemoattraction. Activated fibroblasts proliferate every three days.

Results

Simulating normal tissue healing. This ABM was capable of reproducing the qualitative features and general time course of skin wound healing, with regards to the dynamics of neutrophils, macrophages, and fibroblasts (FIG. 2A); and the inflammatory cytokines IL-1, IL-10, and TNF (FIG. 2B). The values in the figures are averaged over the entire space (also in all subsequent figures). Collagen deposition and tissue damage variables served as surrogates for wound healing, and these, too, exhibited the expected qualitative behavior with wound resolution occurring in approximately 1 month (FIG. 2C). The simulation presented is one run, representative of the behavior of the ABM under these baseline conditions. In later simulations (see below) variability is shown across simulations at defined time points in the inflammation/healing process. Notably, this simulation did not address aspects of longer-term collagen remodeling since this aspect of healing was not incorporated in the ABM.

Figure 2:
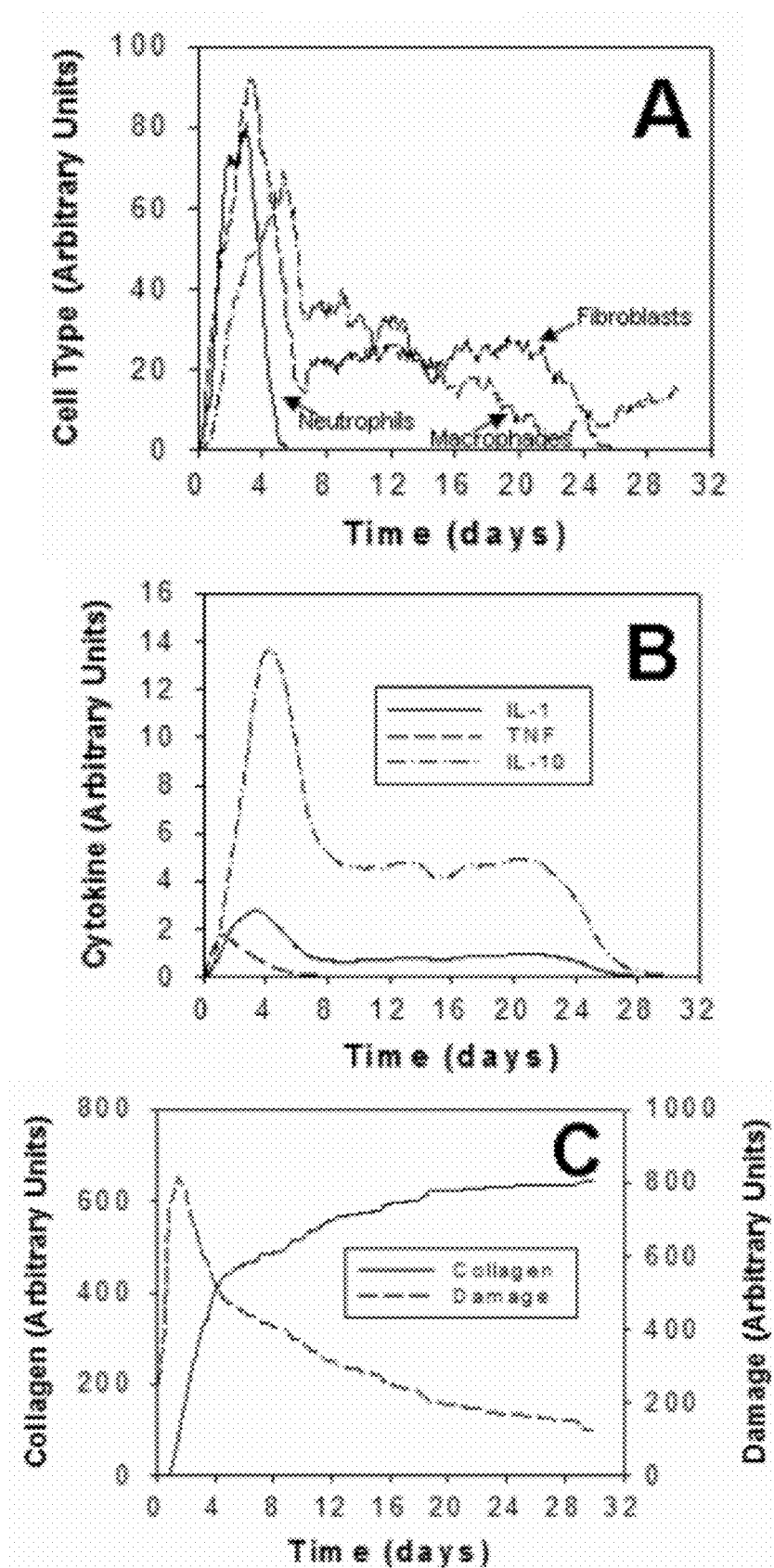
FIG. 2 shows simulations of baseline skin wound healing. Simulations using the ABM were carried out to 30 days, and show the dynamics of inflammatory cells (Panel A), cytokines (Panel B), collagen (Panel C, left y-axis), and tissue damage (Panel C, right y-axis).
Figure 3:
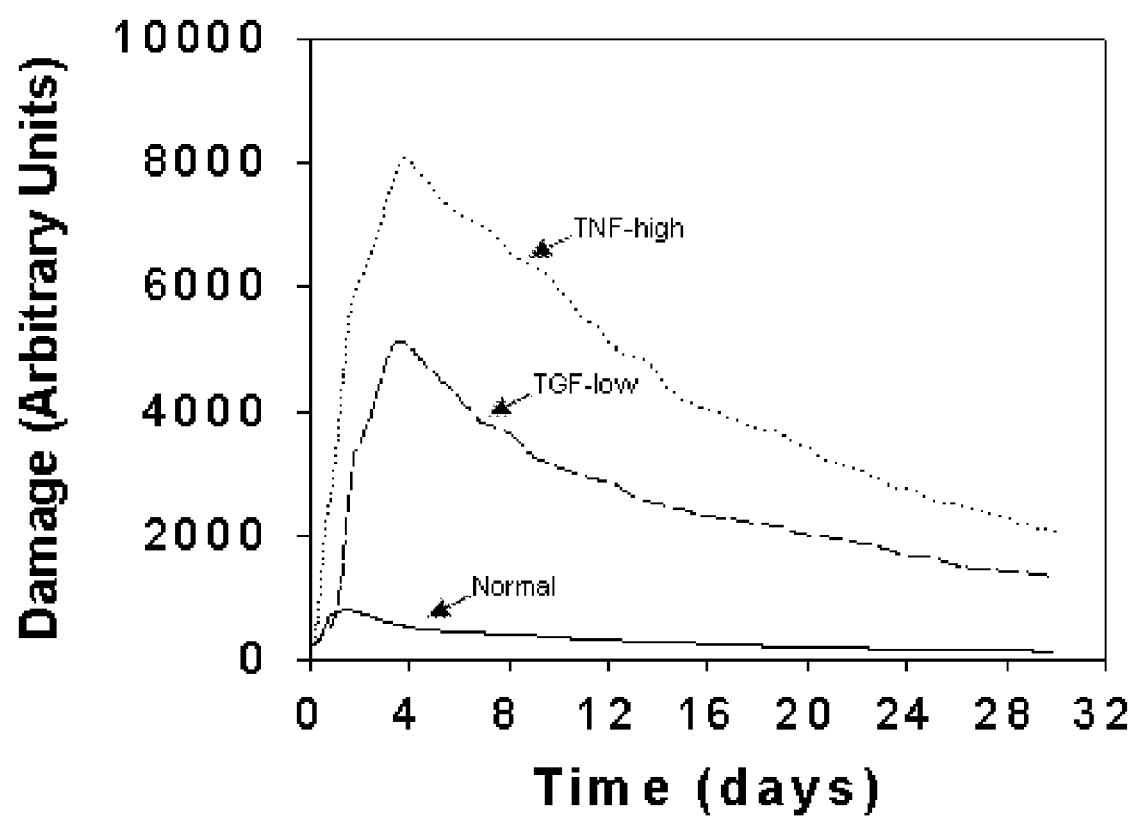
FIG. 3 shows simulations of skin healing trajectories in Normal, TNF-high, and TGF-β1-low cases. The simulated recovery of normal skin tissue damage (i.e., wound healing; solid line) is compared to one of two hypothetical derangements underlying DFU: elevated TNF production (dotted line) or reduced capacity to produce TGF-β1 (dashed line).

Comparison of normal vs. DFU healing. Because inflammation is the initial driver of wound healing, it was hypothesized that inflammatory derangements seen in DFU might underlie the delayed healing characteristic of these lesions. Previous studies have suggested that macrophages from diabetics exhibit elevated TNF production Hussain M J, et al. Diabetologia 1996; 39(1):60-9 and Harsch I A, et al. Eur J Pharmacol 2003; 481(2-3):249-60, and other studies have demonstrated reduced expression of active TGF-β1 (Jude E B, et al. Diabet Med 2002; 19(6):440-7). TNF and TGF-β1 cross-regulate their own expression and activity in diverse and complex ways, with TNF generally inducing the expression of TGF-β1 and TGF-β1 suppressing the expression of TNF (Wahl S M, McCartney-Francis N, Mergenhagen SE. Inflammatory and immunomodulatory roles of TGF-Beta. Immunol Today 1989; 10:258-61; Wahl S M. Transforming growth factor b: The good, the bad, and the ugly. J Exp Med 1994; 180:1587-90 and Letterio J J, Vodovotz Y, Bogdan C. TGF-β and IL-10: Inhibitory Cytokines Regulating Immunity and the Response to Infection. In: Henderson B, Higgs G, editors. Novel Cytokine Inhibitors. Base1: Birkhauser Verlag, 2000:217-42. Accordingly, it was hypothesized that either derangement alone might be sufficient to result in altered healing. To test this hypothesis, the effects of elevated TNF or reduced TGF-β1 were simulated. FIG. 3 shows healing trajectories (shown as dynamics of tissue damage) of normal (solid line, reprised from FIG. 2C), TNF-high DFU (dotted line), and TGF-β1-low DFU (dashed line). As can be seen, simulated damage in the DFU settings remains elevated as compared to normal wound healing, which we interpret as delayed healing. As suggested previously (Robson M C, et al. Arch Surg 2000; 135(7):773-7 and Steed D L, Surg Clin North Am 2003; 83(3):547-vii), the healing trajectories of DFU in these simulations are clearly delayed as compared to normal skin healing. Importantly, this is an emergent property of the system, since the various parameters indicative of DFU-like healing have not been programmed into the simulation but rather emerge as a result of changing a single variable (either TNF or TGF-β1).

Simulating Clinical Variability and Known Therapies for DFU.

Figure 4:
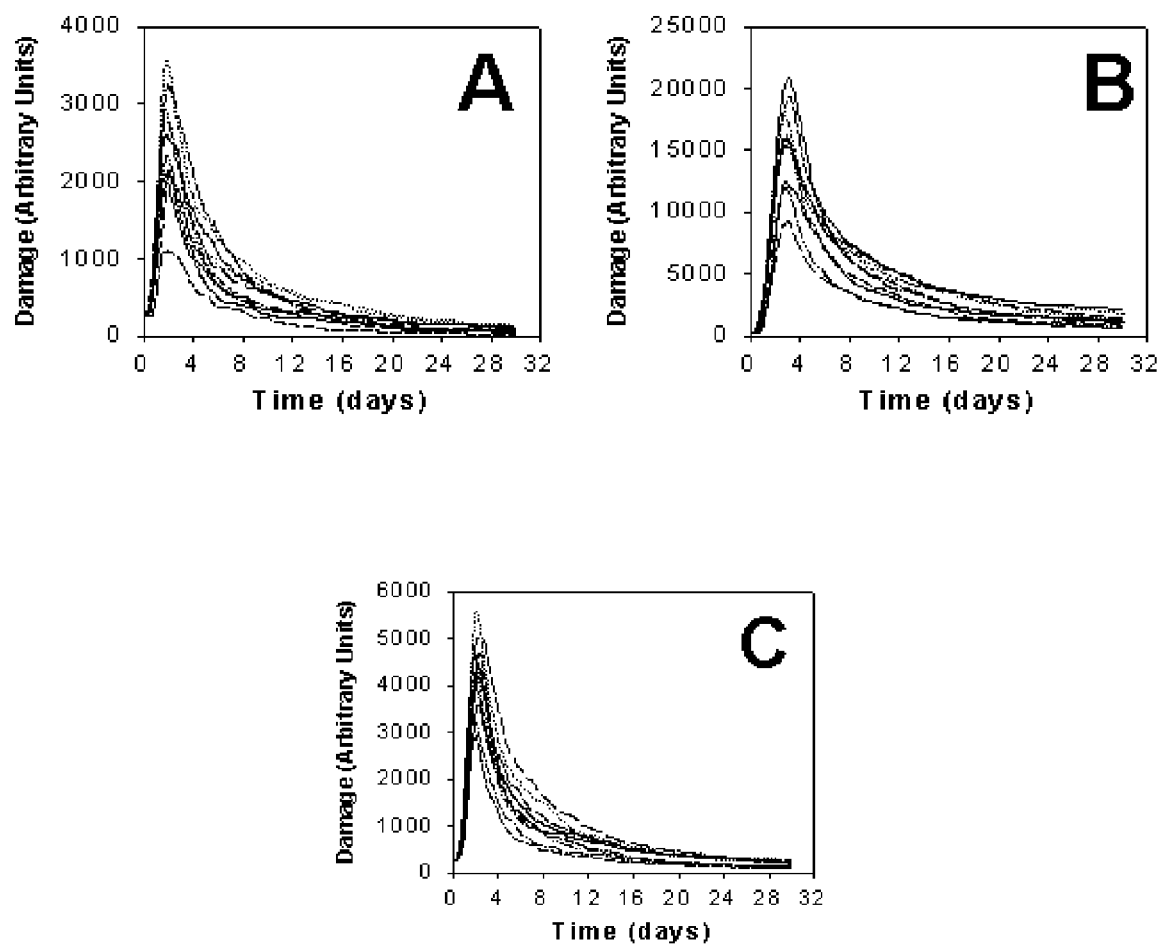
FIG. 4 shows simulation of the variability in skin healing trajectories in Normal, TNF-high, and TGF-β1-low cases.

We wished to determine if our ABM would result in the sort of patient-to-patient variability that is typically observed clinically with regards to DFU healing. Accordingly, we varied—and examined our scenarios of normal (FIG. 4A), TNF-high (FIG. 4B), and TGF-β1-low (FIG. 4C) wound healing. These figures show that TNF-high and TGF-β1-low conditions result in higher levels of tissue damage, though our ABM exhibits the type of inter-individual variability previously shown in ABM of acute inflammation (An G. Agent-based computer simulation and SIRS: building a bridge between basic science and clinical trials. Shock 2001; 16(4): 266-73 and An G. In-silico experiments of existing and hypothetical cytokine-directed clinical trials using agent based modeling. Crit. Care Med 2004; 32:2050-60).

Figure 5:
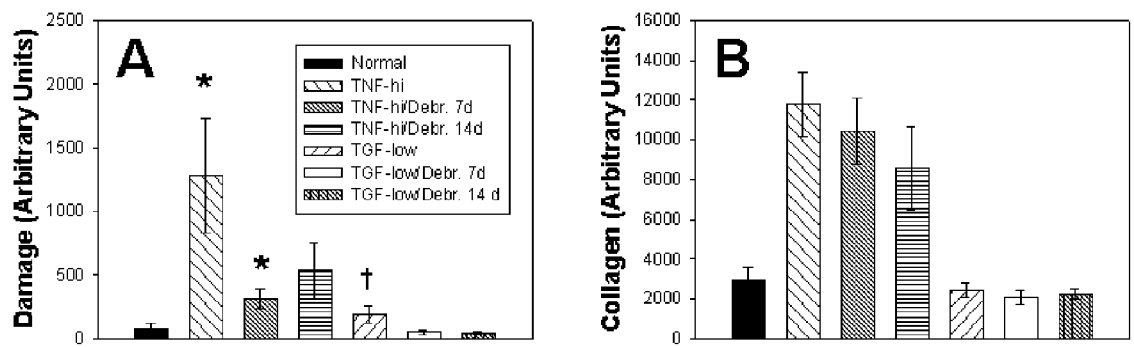
FIG. 5 shows a simulation of debridement of diabetic foot ulcers (DFU). Debridement ("Debr.") was simulated as removal of 75% of damaged tissue at the indicated day (either 7 or 14 days post-wounding). Simulated tissue damage (Panel A) or collagen content (Panel B) was assessed at day 30 post-wounding. Asterisk: $P<0.05$ vs. Normal; †=$P<0.05$ vs. TNF-high.

This ABM was further validated by examining its ability to simulate the actions of known therapies for DFU. Debridement is a standard procedure used for DFU, which has been reported to improve healing in ~25% of patients. Accordingly, we simulated this procedure by making the assumption that approximately 75% of damaged tissue would be removed at either day 7 or 14 into the time course of healing. Simulated tissue damage was then assessed at day 30. These simulations were carried out in the presence of the inter-individual variability depicted in FIGS. 4A-C, in an attempt to determine if the type of variability observed in clinical trials would be seen. FIG. 5A demonstrates the elevated damage at simulated day 30 in both TNF-high and TGF-β1-low DFU as compared to normal skin healing. Interestingly, our simulation suggests that collagen content would be elevated relative to normal healing if DFU were caused by elevated TNF, but the predicted collagen content of DFU derived from low TGF-β1 is predicted to be no different from that of normal controls (FIG. 5B). Debridement at 7 d was predicted to result in statistically significant reductions in tissue damage in both TNF-high and TGF-β1-low DFU (FIG. 5A). Interestingly, this effect of simulated debridement did not reach statistical significant when simulated debridement was performed at day 14 d. In contrast, debridement was not predicted to result in decreased collagen an either 7 or 14 d, in either TNF-high or TGF-β1-low DFU. These results are in general agreement with clinical studies of debridement. We note that in subsequent simulations below, debridement was not simulated in order to be able to gain insight into the single manipulation being studied.

Figure 6:
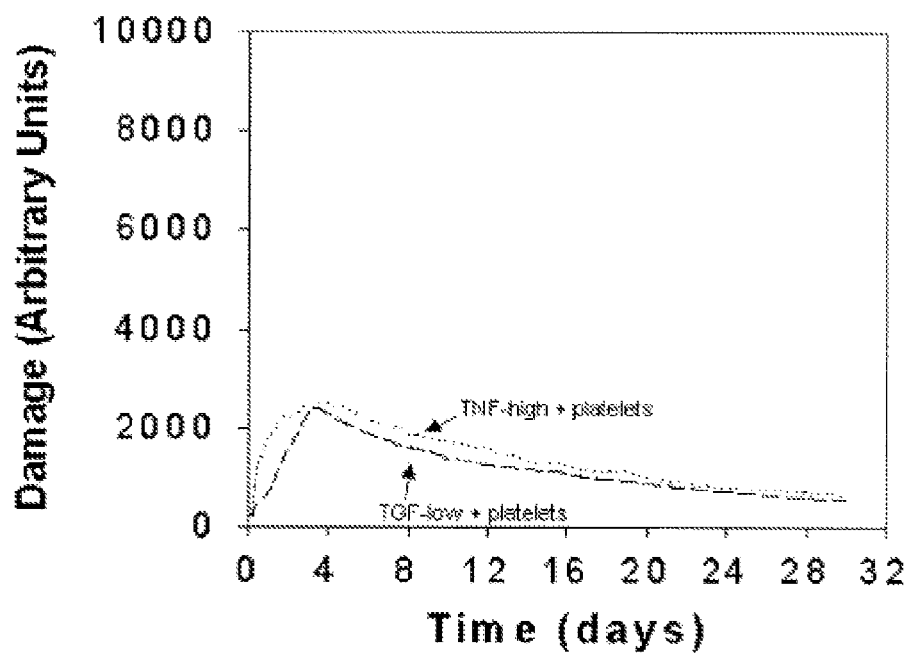
FIG. 6 shows a simulation of PDGF/platelet release therapy for DFU. The simulation of FIG. 2 was repeated, this time in the presence of elevated effects of platelets (increasing the effect of platelets on macrophages by 70% and the effect of platelets on neutrophils by 18%).

We attempted to simulate biological therapies for DFU. Although multiple randomized prospective clinical trials have been performed using growth factors in the treatment of DFU, only PDGF has been approved for use (Richard J L, et al. Diabetes Care 1995; 18(1):64-9). PDGF, which is released from platelet granules (Heldin C H, Westermark B. Mechanism of action and in vivo role of platelet-derived growth factor. Physiol Rev 1999; 79(4):1283-316), has been found to increase healing in diabetic neuropathic foot ulcers and is marketed as REGRANEX™ (Steed D L. Clinical evaluation of recombinant human platelet-derived growth factor for the treatment of lower extremity diabetic ulcers. Diabetic Ulcer Study Group. J Vasc Surg 1995; 21(1):71-8; Wieman T J, Smiell J M, Su Y. Efficacy and safety of a topical gel formulation of recombinant human platelet-derived growth factor-BB (becaplermin) in patients with chronic neuropathic diabetic ulcers. A phase III randomized placebo-controlled double-blind study. Diabetes Care 1998; 21(5):822-7; d'Hemecourt P A, Smiell J M, Karim M R. Sodium carboxymethylcellulose aqueous-based gel versus becaplermin gel in patients with non-healing lower extremity ulcers. WOUNDS 1998; 10:69-75; Smiell J M, Wieman T J, Steed D L, Perry B H, Sampson A R, Schwab B H. Efficacy and safety of becaplermin (recombinant human platelet-derived growth factor-BB) in patients with nonhealing, lower extremity diabetic ulcers: a combined analysis of four randomized studies. Wound Repair Regen 1999; 7(5):335-46 and Robson M C, Payne W G, Garner W L, Biundo J, Giacalone V, Cooper D, Ouyang P. Integrating the results of Phase IV (postmarketing) clinical trial with four previous trials reinforces the position that Regranex (becapleminin) gel 0.01% is an effective adjunct to the treatment of diabetic foot ulcers. J Appl Res 2005; 5:35-45). There is also limited evidence to suggest clinical benefit from a platelet releasate that contains many growth factors including PDGF (Moulin V, et al. Cell Mol Biol (Noisy-le-grand) 1998; 44(6):961-71; Steed D L, Clin Plast Surg 1998; 25(3):397-405; Steed D L, Goslen J B, Holloway G A, Malone J M, Bunt T J, Webster M W. Randomized prospective double-blind trial in healing chronic diabetic foot ulcers. CT-102 activated platelet supernatant, topical versus placebo. Diabetes Care 1992; 15(11):1598-604 and Holloway G, Steed D, DeMarco M, Matsumoto T, Moosa H, Webster M. A randomized, controlled multicenter, dose response trial of activated platelet supernatant, topical CT-102 in chronic, non-healing, diabetic wounds. WOUNDS 1993; 5:198-206). In order to further validate the ABM, in which platelets are one class of agent, predicted tissue damage was assessed in the setting of increased platelet-derived factors. This increase was simulated by increasing separately the chemoattractant effect of platelets on macrophages and neutrophils (both effects being parameters in our ABM). As seen in FIG. 6, increasing the chemoattractant effect of platelets on macrophages by 70% and the chemoattractant effect of platelets on neutrophils by 18% resulted in reduced damage under both the increased TNF (dotted line) and reduced TGF-β1 (solid line) cases (compare to the same simulations in FIG. 2).

This finding arose from a systematic modulation of the relative chemoattracts effects of platelets on macrophages and neutrophils, in a further attempt to explore the potential for our ABM to reproduce inter-patient variability (Tables 1 and 2). Interestingly, different ratios of the effects of platelets on macrophages and neutrophils were predicted to be either efficacious or non-efficacious at reducing tissue damage in a non-intuitive manner. In all cases, benefit was predicted if the effect of platelets on macrophages was greater than the effect of platelets on neutrophils, and this held true whether we assumed that the underlying cause of DFU was elevated TNF (Table 1) or reduced TGF-β1 (Table 2). Thus, under certain conditions, our ABM is capable not only of reproducing delayed skin healing using assumptions of the underlying pathology of DFU, but also of reproducing the effect of a known therapy for DFU. These results may explain why some patients respond to PDGF or platelet releasate and some do not (Steed D L, et al. Diabetes Care 1992; 15(11):1598-604 and Holloway G, Steed D, DeMarco M, Matsumoto T, Moosa H, Webster M. A randomized, controlled multicenter, dose response trial of activated platelet supernatant, topical CT-102 in chronic, non-healing, diabetic wounds. WOUNDS 1993; 5: 198-206.

TABLE 1

Simulation of DFU therapy. The effect on tissue damage of increasing the chemoattraction of platelets on macrophages (P1) and neutrophils (P2) was simulated. In this case, DFU were assumed to arise from elevations in TNF production. Healing (assessed at 4-6 days) was assumed to occur if the predicted damage was lower than that predicted for the untreated DFU (8000 arbitrary units; see FIG. 2, dotted line).

| P1 (% increase over P1 in the TNF-high simulation [FIG. 2a]) | P2 (% increase over P2 in the TNF-high simulation [FIG. 2a]) | Damage (Arbitrary Units) | Healing (relative to no treatment) |
|---|---|---|---|
| 129 | 19 | 892 | Yes |
| 129 | 39 | 5600 | Yes |
| 129 | ≧59 | >8000 | No |
| 95 | 19 | 2000 | Yes |
| 95 | 39 | 2070 | Yes |
| 95 | ≧59 | >8000 | No |
| 69 | 19 | 2700 | Yes |
| 69 | ≧39 | >8000 | No |
| 44 | 19 | 3100 | Yes |
| 44 | ≧39 | >8000 | No |
| 34 | 19 | 4000 | Yes |
| 34 | ≧39 | >8000 | No |
| 22 | ≧19 | >8000 | No |

TABLE 2

Simulation of DFU therapy. The effect on tissue damage of increasing the chemoattraction of platelets on macrophages (P1) and neutrophils (P2) was simulated. In this case, DFU were assumed to arise from reduced TGF-β1 production. Healing (assessed at 4-6) was assumed to occur if the predicted damage was lower than that predicted for the untreated DFU (3000 arbitrary units; see FIG. 2, dashed line).

| P1 (% increase over P1 in TGF-β1-low simulation [FIG. 2a]) | P2 (% increase over P2 in the TGF-β1-low simulation [FIG. 2a]) | Damage (Arbitrary Units) | Healing (relative to no treatment) |
|---|---|---|---|
| 170 | 19 | 1400 | Yes |
| 150 | 19 | 1600 | Yes |
| 129 | 19 | 2000 | Yes |
| 129 | >39 | >3000 | No |
| 95 | ≧19 | >3000 | No |
| 69 | 19 | 2700 | ~Equal |
| 69 | ≧39 | >3000 | No |
| 44 | 19 | 2300 | Yes |
| 44 | ≧39 | >3000 | No |
| 34 | 19 | 3500 | No |
| 34 | ≧39 | >3000 | No |
| 22 | ≧19 | >3000 | No |

Figure 7:
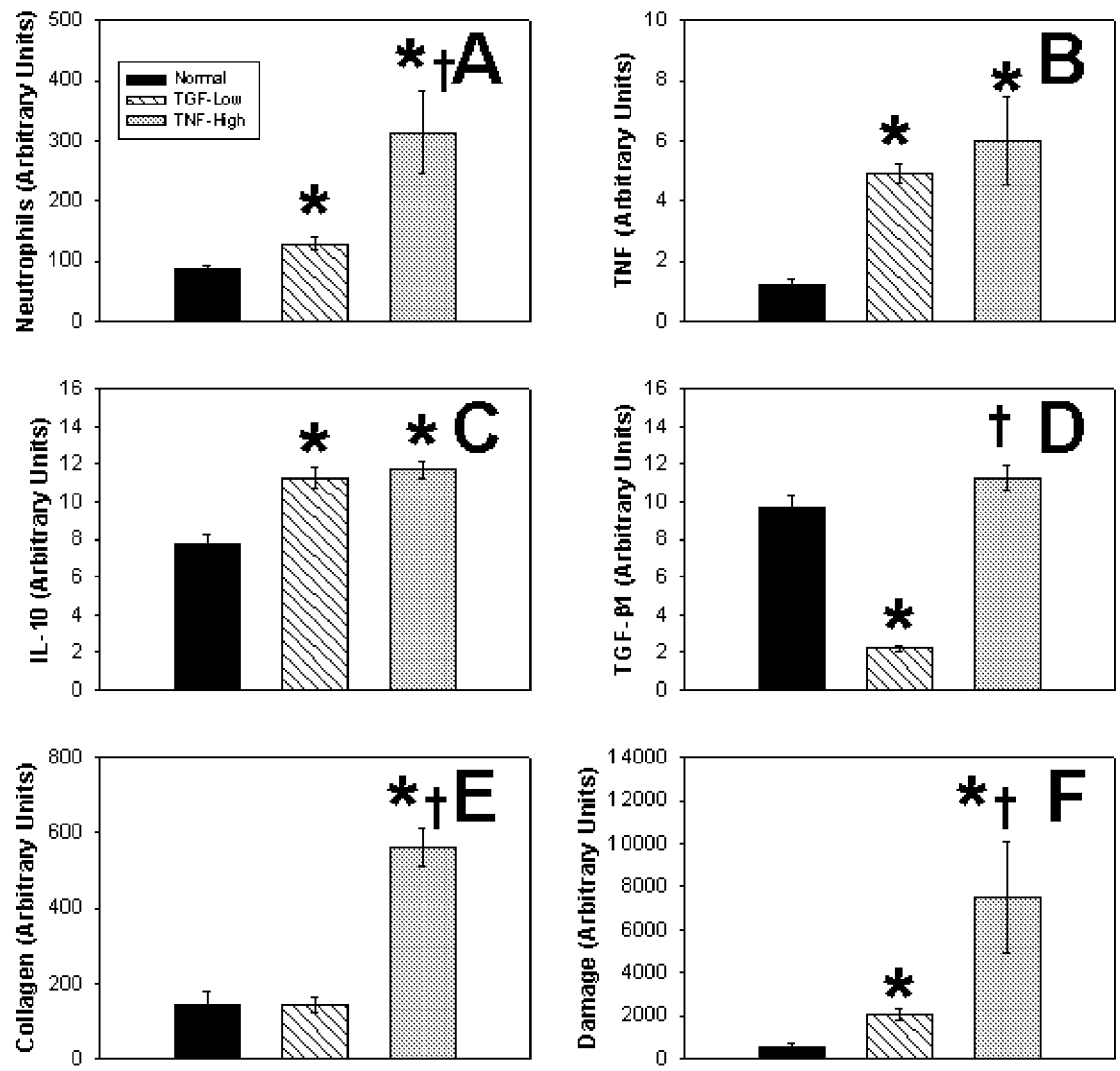
FIG. 7 shows simulations of inflammation and skin healing parameters in normal, TNF-high, and TGF-β1-low cases. The simulated levels of neutrophils (Panel A), TNF (Panel B), IL-10 (Panel C), TGF-β1 (Panel D), collagen (Panel E), and tissue damage (Panel E) are shown for normal skin healing (black bars) and two hypothetical derangements underlying DFU: elevated TNF production (gray bars) or reduced capacity to produce TGF-β1 (hatched bars). *: $P<0.05$ vs. Normal; †: $P<0.05$ vs. TGF-β1-low (all by Kruskall-Wallis ANOVA on ranks followed by Tukey post-hoc test).

Inflammatory and Healing Characteristics of simulated DFU. Having demonstrated that the overall features of the ABM are valid, the characteristics associated with healing were examined in simulations of normal tissue and the two ways of simulating DFU (TNF-high and TGF-β1-low). These simulations were all examined at 2.5 days in order to examine early drivers of the inflammatory and healing responses. In all cases, ten simulations of each condition were carried out because the ABM platform is inherently stochastic (Ermentrout G B, Edelstein-Keshet L. Cellular automata approaches to biological modeling. J Theor Biol 1993; 160(1):97-133). This approach allowed simulation of several "patients" and also to carry out a statistical analysis (Kruskall-Wallis ANOVA on ranks followed by Tukey post-hoc test) to ascertain group differences (considered significant at P<0.05). As seen in FIG. 7, the qualitative features of simulated wound healing either in the setting of elevated TNF production (gray bars) or reduced TGF-β1 production (hatched bars) as compared to normal healing (black bars) are largely similar: elevated neutrophil influx (FIG. 7A), elevated TNF expression (FIG. 7B), elevated IL-10 (FIG. 7C), reduced collagen deposition (FIG. 7E), and increased tissue damage (FIG. 7F). In general, these are all hallmarks of DFU. Interestingly, decreased TGF-β1 expression as compared to normal healing was observed in the simulations in which DFU were presumed to arise from reduced TGF-β1 (as expected, FIG. 7D, hatched bar), but this was not the case in simulations in which TNF was over-produced (FIG. 7D, gray bar).

Figure 8:
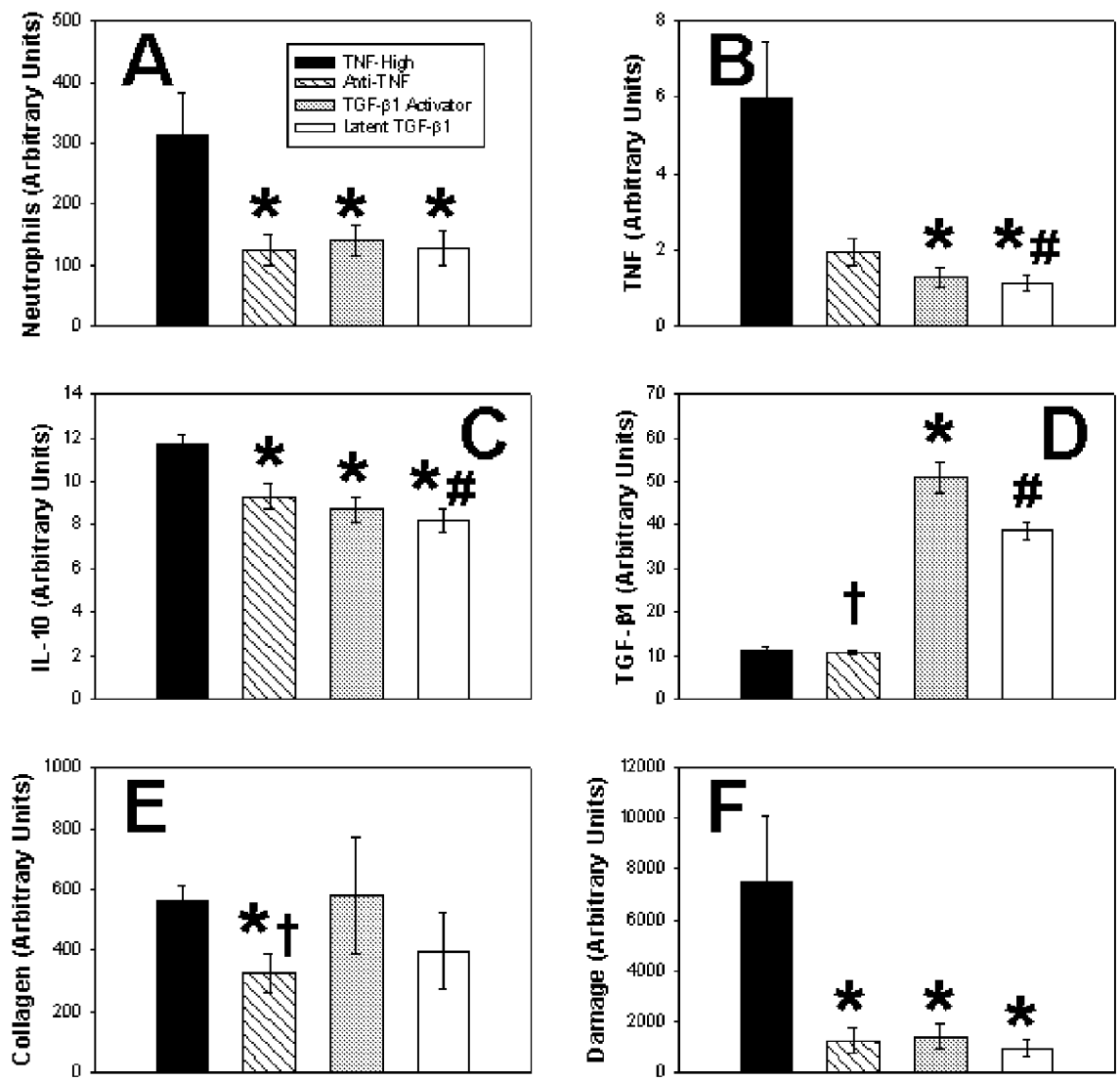
FIG. 8 shows simulations of therapies in TNF-high DFU. The simulated levels of neutrophils (Panel A), TNF (Panel B), IL-10 (Panel C), TGF-β1 (Panel D), collagen (Panel E), and tissue damage (Panel E) are shown for skin healing in DFU assumed to arise due to elevated TNF production (black bars). Also simulated are three hypothetical therapies: anti-TNF neutralizing antibodies (hatched bars), an agent that activates endogenous latent TGF-β1 (gray bars), and treatment with latent TGF-β1 (open bars). *: $P<0.05$ vs. TNF-high baseline; †: $P<0.05$ vs. TGF-β1 activator; #: $P<0.05$ vs. anti-TNF (all by Kruskall-Wallis ANOVA on ranks followed by Tukey post-hoc test).
Figure 9:
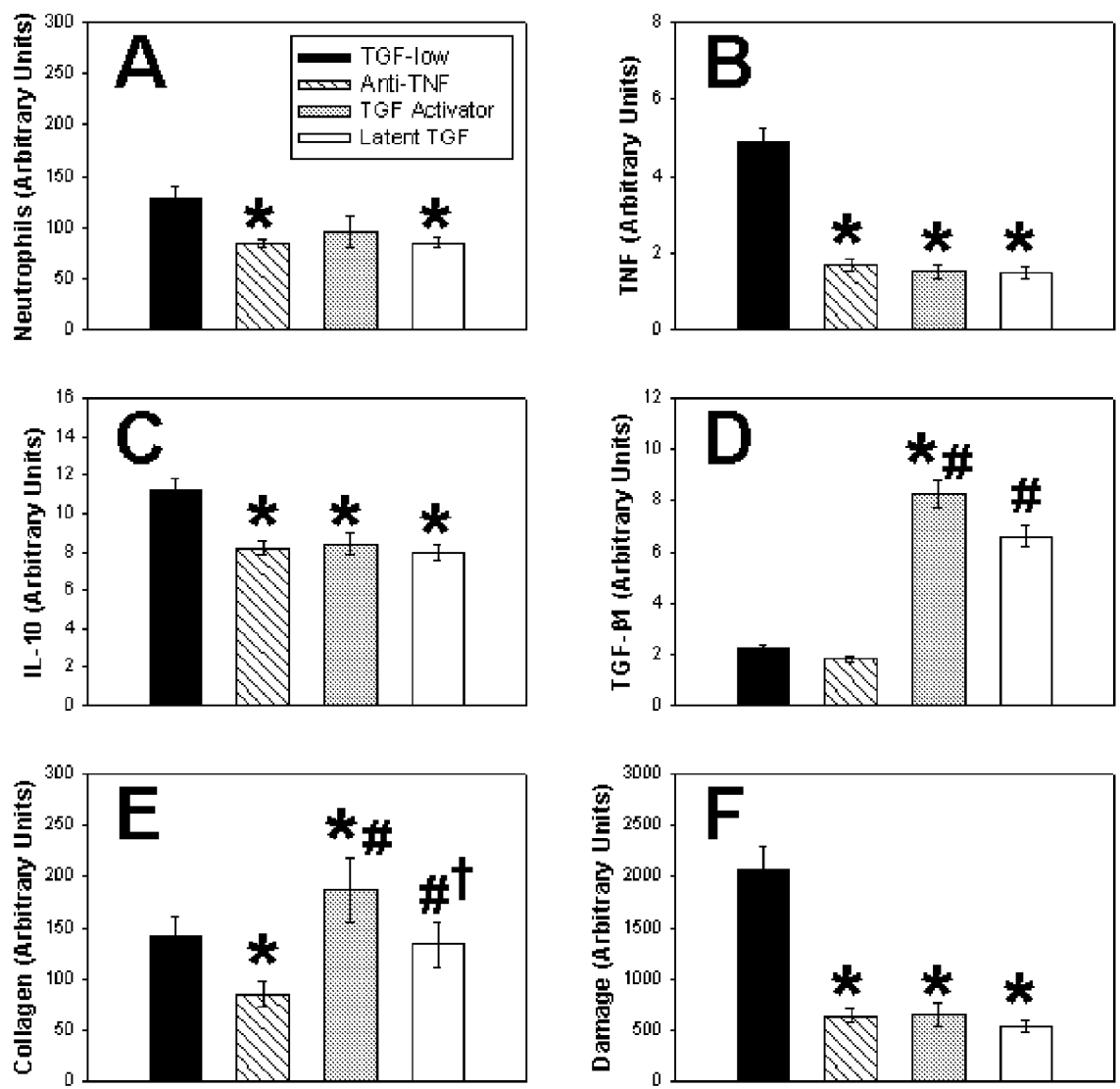
FIG. 9 shows simulations of therapies in TGF-β1-low DFU. The simulated levels of neutrophils (Panel A), TNF (Panel B), IL-10 (Panel C), TGF-β1 (Panel D), collagen (Panel E), and tissue damage (Panel E) are shown for skin healing in DFU assumed to arise due to reduced TGF-β1 production (black bars). Also simulated are three hypothetical therapies: anti-TNF neutralizing antibodies (hatched bars), an agent that activates endogenous latent TGF-β1 (gray bars), and treatment with latent TGF-β1 (open bars). *: $P<0.05$ vs. TGF-β1-low baseline; †: $P<0.05$ vs. TGF-β1 activator; #: $P<0.05$ vs. anti-TNF (all by Kruskall-Wallis ANOVA on ranks followed by Tukey post-hoc test).

Simulating hypothetical therapies for DFU. Numerous studies in animal models of diabetic wound healing have demonstrated efficacy of topical administration of single growth factors such as PDGF (Greenhalgh D G, et al. Am J Pathol 1990; 136(6):1235-46. and Albertson S, et al. Surgery 1993; 114(2):368-72), acidic or basic FGF, Broadley K N, et al. Int J Tissue React 1988; 10(6):345-53; Greenhalgh D G, et al. PDGF and FGF stimulate wound healing in the genetically diabetic mouse. Am J Pathol 1990; 136(6):1235-46; Albertson S, et al. Surgery 1993; 114(2):368-72; Broadley K N, et al. Biotechnol Ther 1989; 1(1):55-68 and Klingbeil C K, Cesar L B, Fiddes J C. Basic fibroblast growth factor accelerates tissue repair in models of impaired wound healing. Prog Clin Biol Res 1991; 365:443-58), or TGF-β1 (Broadley K N, et al. Int J Tissue React 1988; 10(6):345-53). However, these results have been confirmed in clinical trials of DFU (Richard J L, et al. Diabetes Care 1995; 18(1):64-9. In an attempt to determine if in silico methodologies could suggest some insights into therapy design for DFU, simulated therapeutic strategies were applied to simulations of delayed healing depicted in FIG. 7. Since both elevated TNF and reduced TGF-β1 gave generally similar qualitative patterns of inflammatory and healing derangements, the simulated therapies were tested under settings of either elevated TNF (FIG. 8) or reduced TGF-β1 (FIG. 9). The therapies were chosen to simulate are directly related to these derangements: neutralizing antibodies to TNF (anti-TNF), agents that increase the rate of TGF-β1 activation, and latent TGF-β1 itself. The rationale for these interventions was the following. In the case of anti-TNF, FDA-approved anti-TNF antibodies are available for the treatment of several inflammatory diseases, with further indications likely (Baugh J A, Bucala R. Mechanisms for modulating TNF alpha in immune and inflammatory disease. Curr Opin Drug Discov Devel 2001; 4(5):635-50; Braun J, Sieper J. Overview of the use of the anti-TNF agent infliximab in chronic inflammatory diseases. Expert Opin Biol Ther 2003; 3(1):141-68; Calamia K T. Current and future use of anti-TNF agents in the treatment of autoimmune, inflammatory disorders. Adv Exp Med Biol 2003; 528:545-9 and D'Haens G R. Infliximab as disease-modifying therapy. Eur J Gastroenterol Hepatol 2003; 15(3):233-7); additionally, we have carried out previous work on simulating mathematically the actions of anti-TNF in the setting of sepsis (Clermont G, Bartels J, Kumar R, Constantine G, Vodovotz Y, Chow C. In silico design of clinical trials: a method coming of age. Crit. Care Med 2004; 32:2061-70). TGF-β1 modulation (either provision of TGF-β1 or its inhibition) has been proposed as a possible therapy for various aspects of aberrant wound healing (Carter K. Growth factors: the wound healing therapy of the future. Br J Community Nurs 2003; 8(9):S15-9, S22 and Krishnamoorthy L, Morris H L, Harding K G. Specific growth factors and the healing of chronic wounds. J Wound Care 2001; 10(5):173-8). TGF-β1, like all other isoforms of TGF-β, is synthesized in a biologically inactive (latent) state and must be activated through various mechanisms in order to bind to its cognate receptor complex and exert its diverse biological functions (Annes J P, et al. J Cell Sci 2003; 116(Pt 2):217-24 and Zamora R, et al. Crit. Care Med 2005; 33:S478-S481). Treatment with active TGF-β1 as well as TGF-β2 has been attempted in the setting of DFU, with initially promising results but ultimately lack of statistically significant efficacy (Robson M C, et al. Curr Probl Surg 2001; 38(2):72-140 and Bennett S P, Griffiths G D, Schor A M, Leese G P, Schor S L. Growth factors in the treatment of diabetic foot ulcers. Br J Surg 2003; 90(2): 133-46). One reason for this lack of overall efficacy might be that active TGF-β1 has a shorter half-life than latent TGF-β1 (Wakefield L M, Winokur T S, Hollands R S, Christopherson K, Levinson A D, Sporn M B. Recombinant latent transforming growth factor Beta1 has a longer plasma half-life in rats than active transforming growth factor Beta1, and a different tissue distribution. J Clin Invest 1990; 86:1976-84). In the case of TGF-β1 activation, such effects of NO have been described (Vodovotz Y, et al. Cancer Res 1999; 59:2142-9 and Luckhart S, Crampton A L, Zamora R, Lieber M J, Dos Santos P C, Peterson T M L, Emmith N, Lim J, Wink D A, Vodovotz Y. Mammalian transforming growth factor-b1 activated after ingestion by *Anopheles stephensi* modulates mosquito immunity. Infect Immun 2003; 71:3000-9) and it was suggested that this, among other effects of NO on cytokines, may underlie the generally beneficial effects of NO in wound healing (Schwentker A, Vodovotz Y, Weller R, Billiar T R. Nitric oxide and wound repair: role of cytokines? Nitric Oxide 2002; 7:1-10). It is therefore hypothesized herein that a class of agents such as NO could selectively augment or suppress TGF-β1 activation and may have therapeutic utility in wound healing. As seen in FIGS. 7 and 8, ten simulations of each condition, were performed and statistical significance was assessed by Kruskall-Wallis ANOVA on ranks followed by Tukey post-hoc test.

Regardless of whether DFU healing was simulated as stemming from elevated TNF production (FIG. 7) or reduced TGF-β1 production (FIG. 8), all three therapies (anti-TNF [hatched bars], latent TGF-β1 [open bars], or TGF-β1 activation [gray bars]) were predicted to suppress neutrophil influx (FIGS. 7A and 8A) and tissue damage (FIGS. 7F and 8F) to the same, statistically significant degree as compared to the DFU baseline (black bars). Interestingly, the simulations suggested that all three therapies would result in a reduction of TNF production in DFU tissue (FIGS. 7B and 8B), though the effect of anti-TNF would not be statistically significant if the cause of DFU was elevated TNF production. This simulation suggested that provision of latent TGF-β1 or activation of endogenous TGF-β1 would elevate overall TGF-β1 expression regardless of the presumed cause (high TNF or low TGF-β1) of DFU pathology (FIGS. 7D and 8D). Interestingly, only the TGF-β1 activator was predicted to increase collagen deposition in a statistically significant fashion, and only upon assumption of reduced baseline TGF-β1 as a cause of DFU. Another non-intuitive finding was the suggestion that anti-TNF would decrease collagen levels above those of baseline DFU (FIGS. 7E and 8E), while at the same time reducing overall tissue damage (FIGS. 7F and 8F).

Chronic wounds are a serious health care problem, costing billions of dollars each year and carry unaccounted but considerable suffering and anguish. DFU, in particular, are a major cause of amputation (Koivukangas V, et al. Diabet Med 1999; 16(7):563-7; Pecoraro R E, et al. Diabe 1991; 40(10): 1305-13; Morain W D, et al. Clin Plast Surg 1990; 17(3):493-501; Ramsey S D, et al. Diabetes Care 1999; 22(3):382-7; Holzer S E, et al. Clin Ther 1998; 20(1): 169-81 and Boyko E J, et al. Diabet Med 1996; 13(11):967-72). There has been great interest in treating DFU with growth factors in recent years. One might suggest that use of growth factors to heal a DFU would result in improved healing and a lowered amputation rate (Richard J L, et al. Diabetes Care 1995; 18(1):64-9). Unfortunately, the number of amputations performed in the United States each year remains essentially unchanged (Koivukangas V, et al. Diabet Med 1999; 16(7):563-7; Pecoraro R E, et al. Diabe 1991; 40(10):1305-13; Morain W D, et al. Clin Plast Surg 1990; 17(3):493-501; Ramsey S D, et al. Diabetes Care 1999; 22(3):382-7; Holzer S E, et al. Clin Ther 1998; 20(1): 169-81 and Boyko E J, et al. Diabet Med 1996; 13(11):967-72).

In order to attempt to break the logjam of compounds available for clinical trials in the setting of DFU, an ABM simulation of the inflammation/wound healing process is described herein. The specific objectives of this project were: 1) to use this ABM to test hypotheses regarding the genesis of DFU and 2) to test in silico possible therapies for DFU. In the process of validating our ABM, we were able to simulate existing therapies for DFU (debridement and platelet releasate/PDGF.

Other groups have also published studies on modeling wound healing, but have not focused on the interrelation between inflammation and wound healing in the setting of DFU as described herein. Current mathematical modeling of wound healing has focused mainly on two areas: epidermal wound healing and dermal wound healing. For epidermal wound healing, Sherratt and Murray (Sherratt J A, et al. Proc Biol Sci 1990; 241(1300):29-36) proposed a two-dimensional diffusion-reaction type of Partial Differential Equation model based on a set of biological experiments. Their model consists of epithelial cell density per unit area and the concentration of mitosis-regulating substances (Murray J D. Mathematical Biology. Heidelberg (Germany): Springer-Verlag, 1989). Recently, Walker et al. (IEEE Trans Nanobioscience 2004; 3:153-63 and Walker D C, et al. Biosystems 2004; 76(1-3):89-100 used an ABM to simulate wounded epithelial cell monolayers, and they suggest that based on the simple rules, it is sufficient to qualitatively predict the calcium-dependent pattern of wound closure observed in vitro.

For dermal wound healing, the first mathematical models were derived from the Murray-Oster mechanical theory by Murray and Tranquillo Murray J D, et al. Physics Rep 1988; 171:59-84; Tranquillo R T, et al. J Theor Biol 1992; 158(2): 135-72; Tranquillo R T, Murray J D. Mechanistic model of wound contraction. J Surg Res 1993; 55(2):233-47), and these models include the mechanisms involved in dermal wound contraction. Since then, several more complex models have been developed. These models include multiple cell types and multiple types or phases of the viscoelastic extracellular matrix (ECM) (Murray J D. Mathematical Biology. Heidelberg (Germany): Springer-Verlag, 1989; Cook, J. A mathematical model for dermal wound healing: wound contraction and scar formation. 1995. University of Washington (Seattle). RefType: Thesis/Dissertation and Olsen L, Sherratt J A, Maini P K. A mechanochemical model for adult dermal wound contraction and the permanence of the contracted tissue displacement profile. J Theor Biol 1995; 177(2):113-28). Other models include additional equations/behavior (Murray J D. Mathematical Biology. Heidelberg (Germany): Springer-Verlag, 1989; Olsen L, et al. J Theor Biol 1995; 177(2):113-28 and Dallon J C, Sherratt J A, Maini P K. Modeling the effects of transforming growth factor-beta on extracellular matrix alignment in dermal wound repair. Wound Repair Regen 2001; 9(4):278-86).

The literature regarding the inflammatory genesis of DFU is sparse. However, two possible mechanisms stand out: elevated TNF (Hussain M J, et al. Diabetologia 1996; 39(1): 60-9) and reduced TGF-β1 (Jude E B, et al. Diabet Med 2002; 19(6):440-7). Since both of these cytokines are highly interrelated in their biology, several of these interactions were incorporated in the model described herein. The simulations described herein suggest that for many indices of inflammation and healing, the effects of elevated TNF and reduced TGF-β1 are very similar (FIGS. 2 and 3). Due to the interrelationships between TNF and TGF-β1, both elevated TNF and reduced TGF-β1 are predicted to be associated with increased inflammatory infiltrates, elevated TNF and IL-10, reduced collagen, and elevated tissue damage. However, only the simulation in which TGF-β1 is reduced, and not the case in which TNF is elevated, is predicted to be associated with the reported decreased expression of TGF-β1 in DFU (Jude E B, et al. Diabet Med 2002; 19(6):440-7). Thus, our simulations support the hypothesis that a central derangement in skin healing that leads to DFU is the reduced expression of TGF-β1. Nonetheless, it is possible or perhaps even likely that more than one cause of DFU exists. Given the overall qualitative similarity between the features of healing in the setting of reduced TGF-β1 and elevated TNF, both mechanisms (and others as well) may be operant in DFU. Further clinical studies are needed in order to address this issue. In any case, these different assumptions can be used in the in silico design and testing of DFU therapeutics, since this variability could be used to create simulated clinical trials; we Vodovotz Y, et al. Curr Opin Crit. Care 2004; 10:383-90 and Clermont G, et al. Crit. Care Med 2004; 32:2061-70 and others (An G. In-silico experiments of existing and hypothetical cytokine-directed clinical trials using agent based modeling. Crit. Care Med 2004; 32:2050-60) have demonstrated the utility of this approach in the setting of sepsis.

Whether elevated TNF or reduced TGF-β1 underlies the pathology of DFU, the ABM described herein is capable of reproducing the effect of known therapeutics for DFU. A major type of intervention is debridement, in which necrotic and/or infected areas of a DFU are removed surgically. Studies have shown that debridement improves healing in ~25% of patients. When we simulated the removal of 75% of damaged tissue at either 7 or 14d from the onset of a wound, our ABM suggested that this would result in a statistically significant reduction in tissue damage at 30 d without a change in collagen levels, interpreted by us to mean improved healing. It might be argued that our finding of reduced tissue damage upon simulated removal of damaged tissue would seem obvious, but the finding that collagen levels remain the same suggests that indeed our ABM is depicting healing.

Although multiple randomized prospective clinical trials have been performed using growth factors in the treatment of DFU, only one growth factor, PDGF, has been approved for use (Richard J L, et al. Diabetes Care 1995; 18(1):64-9). PDGF has been found to increase healing in diabetic neuropathic foot ulcers and is marketed as REGRANEX™ (Steed D L, et al. Diabetic Ulcer Study Group. J Vasc Surg 1995; 21(1):71-8; Wieman T J, et al. Diabetes Care 1998; 21(5): 822-7; d'Hemecourt P A, et al. WOUNDS 1998; 10:69-75; Smiell J M, et al. Wound Repair Regen 1999; 7(5):335-46 and Robson M C, et al. J Appl Res 2005; 5:35-45). There is only limited evidence to suggest clinical benefit from other growth factors, including TGF-β1, FGF, IGF-1, GM-CSF, EGF, or a platelet releasate that contains many growth factors Richard J L, et al. Diabetes Care 1995; 18(1):64-9; Steed D L, et al. Diabetes Care 1992; 15(11): 1598-604; Holloway G, et al. WOUNDS 1993; 5:198-206; Mulder G D, Patt L M, Sanders L, Altman M, Hanley M, Duncan G. Enhanced healing of ulcers in patients with diabetes by topical treatment with glycyl-1-histidy-1-lysine. Wound Rep Reg 1994; 2:256-69; Atri S C, Misra J, Bisht D, Misra K. Use of homologous platelet factors in achieving total healing of recalcitrant skin ulcers. Surgery 1990; 108(3):508-12; Knighton D R, Ciresi K F, Fiegel V D, Austin L L, Butler E L. Classification and treatment of chronic nonhealing wounds. Successful treatment with autologous platelet-derived wound healing factors (PDWHF). Ann Surg 1986; 204(3):322-30; Robson M C, Steed D L, McPherson J M, Prett B M. Effects of transforming growth factors b2 on wound healing in diabetic foot ulcers. J Appl Res 2002; 2:133-45; Agrawal R P, Agrawal S, Beniwal S, Joshi C P, Kochar D K. Granulocyte-macrophage colony-stimulating factor in foot ulcers. Diabetic Foot 2003; 6:93-7; de Lalla F, Pellizzer G, Strazzabosco M, Martini Z, Du J G, Lora L, Fabris P, Benedetti P, Erle G. Randomized prospective controlled trial of recombinant granulocyte colony-stimulating factor as adjunctive therapy for limb-threatening diabetic foot infection. Antimicrob Agents Chemother 2001; 45(4):1094-8; Gough A, Clapperton M, Rolando N, Foster A V, Philpott-Howard J, Edmonds M E. Randomised placebo-controlled trial of granulocyte-colony stimulating factor in diabetic foot infection. Lancet 1997; 350(9081):855-9 and Tsang M W, Wong W K, Hung C S, Lai K M, Tang W, Cheung E Y, Kam G, Leung L, Chan C W, Chu C M, Lam E K. Human epidermal growth factor enhances healing of diabetic foot ulcers. Diabetes Care 2003; 26(6): 1856-61). In the simulations described herein, the effects of platelet releasate and PDGF are accounted for through the inclusion of platelets which function to chemoattract macrophages and neutrophils. Though PDGF is not simulated explicitly, it is demonstrated herein that modulating the actions platelets on macrophages and neutrophils can, under certain circumstances, result in reduced tissue damage as compared to that predicted to be found in untreated DFU. Moreover, the exploration of the relative effects of platelets on macrophages and neutrophils suggested that there would be great variability in the efficacy of platelet-related therapies (either PDGF or platelet releasate). Thus, these simulations may be of benefit when attempting to personalize this type of therapy to an individual patient, if ex vivo studies could be carried out to assess the chemoattractant effect of the therapeutic agent on a patient-by-patient basis.

This interaction between inflammation and wound healing in the setting of DFU therapy may also be seen in other ways. In the clinical trials of PDGF, the importance of debridement became apparent. The first clinical trial to demonstrate benefit from PDGF found that extensive debridement, that is, wound excision down to normal tissue beyond the wound space, was associated with the highest healing rate (Steed D L, Donohoe D, Webster M W, Lindsley L. Effect of extensive debridement and treatment on the healing of diabetic foot ulcers. Diabetic Ulcer Study Group. J Am Coll Surg 1996; 183(1):61-4). "Wound excision" was favored, as this procedure removed the tissue with the highest bacterial load and the highest concentration of proteases. It may also be that the tissues removed were those trapped in the inflammatory phase of healing, with elevated TNF and reduced TGF-$\beta$1, a clinical observation that supports the findings of the simulations described herein.

An in silico approach was used to study several hypothetical therapeutic approaches. The first agent we examined was a neutralizing anti-TNF antibody, given that elevated TNF production is a feature of diabetes (Hussain M J, et al. Diabetologia 1996; 39(1):60-9 and Harsch I A, Brzozowski T, Bazela K, Konturek S J, Kukharsky V, Pawlik T, Pawlowski E, Hahn E G, Konturek P C. Impaired gastric ulcer healing in diabetic rats: role of heat shock protein, growth factors, prostaglandins and proinflammatory cytokines. Eur J Pharmacol 2003; 481(2-3):249-60) and given our ability to simulate many of the characteristics of DFU by assuming elevated TNF production. Several FDA-approved anti-TNF antibodies are available for the treatment of various inflammatory diseases (Baugh J A, et al. Curr Opin Drug Discov Devel 2001; 4(5):635-50; Braun J, et al. Expert Opin Biol Ther 2003; 3(1):141-68; Calamia KT Adv Exp Med Biol 2003; 528: 545-9 and D'Haens G R, Eur J Gastroenterol Hepatol 2003; 15(3):233-7. Since we have carried out previous work on simulating mathematically the actions of anti-TNF in the setting of sepsis Clermont G, et al. Crit. Care Med 2004; 32:2061-70, we examined if such a therapy might be of benefit in DFU. Findings suggest that anti-TNF therapy for DFU should be explored.

Another therapy simulated was one in which exogenous, latent TGF-$\beta$1 would be provided or one that would lead to the activation of endogenous TGF-$\beta$1. TGF-$\beta$1 modulation (either provision of TGF-$\beta$1 or its inhibition) has been proposed as a possible therapy for various aspects of aberrant wound healing (Carter K Br J Community Nurs 2003; 8(9): S15-9, S22 and Krishnamoorthy L, et al. J Wound Care 2001; 10(5):173-8. However, treatment with TGF-$\beta$1 was not efficacious as a DFU therapeutic Robson M C, et al. Curr Probl Surg 2001; 38(2):72-140. We reasoned that since latent TGF-$\beta$1 has a longer half-life than active TGF-$\beta$1 Wakefield L M, et al. J Clin Invest 1990; 86:1976-84, it might serve as a better therapeutic agent. The findings described herein support this hypothesis.

We suggest at least one agent that can activate endogenous latent TGF-$\beta$1 and that may be useful as a topical drug: NO, which has been shown in several contexts leads to the activation of latent TGF-$\beta$1 (Vodovotz Y, et al. Cancer Res 1999; 59:2142-9 and Luckhart S, et al. Infect Immun 2003; 71:3000-9). Nitric oxide is central to the wound healing process (Schwentker A, et al. Nitric Oxide 2002; 7:1-10; Yamasaki K, Edington H D, McClosky C, Tzeng E, Lizonova A, Kovesdi I, Steed D L, Billiar T R. Reversal of impaired wound repair in iNOS-deficient mice by topical adenoviral-mediated iNOS gene transfer. J Clin Invest 1998; 101(5):967-71 and Schaffer M R, Tantry U, Gross S S, Wasserkrug H L, Barbul A. Nitric oxide regulates wound-healing. J Surg Res 1996; 63:237-40 and is reduced in diabetic wounds (Schaffer M R, et al. Surgery 1997; 121(5):513-9). The diverse actions of NO in wound healing may be secondary to the modulation of various cytokines including TGF-$\beta$1 (Schwentker A, et al. Nitric Oxide 2002; 7:1-10). In the setting of DFU, chemical NO donors may be applied topically (see, e.g., Krischel V, Bruch-Gerharz D, Suschek C, Kroncke K D, Ruzicka T, Kolb-Bachofen V. Biphasic effect of exogenous nitric oxide on proliferation and differentiation in skin derived keratinocytes but not fibroblasts. J Invest Dermatol 1998; 111(2): 286-91 and Masters K S, Leibovich S J, Belem P, West J L, Poole-Warren L A. Effects of nitric oxide releasing poly(vinyl alcohol) hydrogel dressings on dermal wound healing in diabetic mice. Wound Repair Regen 2002; 10(5):286-94 for examples of topical application of NO) or possibly delivered via gene therapy with either the inducible or constitutive NO synthase (Yamasaki K, et al. J Clin Invest 1998; 101(5):967-71). Interestingly, previous mathematical modeling approaches have examined this issue and suggested that NO production underlies keloids and hypertrophic scarring (Cobbold C A, Sherratt J A. Mathematical modelling of nitric oxide activity in wound healing can explain keloid and hypertrophic scarring. J Theor Biol 2000; 204(2):257-88), both phenomena that have also been ascribed to TGF-$\beta$1 (Diegelmann R F, et al. Front Biosci 2004; 9:283-9).

The model described herein is based on the key mechanisms of inflammation and wound healing, but like any simulation does not incorporate all possible biological mechanisms that might be operant in the process of inflammation and wound healing. The ABM does not account for collagen contraction as part of the wound healing process, though it is an aim to incorporate this mechanism in later iterations of the model. It should be noted that in the ABM framework, it is often difficult to define the direct or indirect role of a given variable in the final outcome, and so the more mechanistic rules an ABM contains the less likely we are to gain this type of insight. Moreover, the more complex the ABM, the greater the computing power necessary to run any single simulation. In the model described herein, we strove to balance model realism with tractability, and believe that the overall findings justify this compromise. Also, the agent-based model structure contains certain assumptions regarding the stochastic nature of some of the processes being modeled, and these assumptions may not represent the exact way in which these processes occur in vivo. Another limitation relates to the way in which the production and clearance of a given agent is modeled, as well as the exact effects than an agent has on another agent. Although we have tried to base our assumptions on literature data whenever possible, the literature is incomplete with regards to certain specific interactions. Finally, this agent-based model is calibrated with regards to literature data on skin wound healing, but has not been specifically calibrated or validated with prospective data from diabetic foot ulcer patients.

The clinical model presented in this manuscript could change the process of drug development for DFU. Taking a drug through basic science testing, toxicology, and clinical trials may cost hundreds of millions of dollars. If the drug could be tested in a mathematical model and found to be of benefit, a pharmaceutical company may be more willing to proceed with a clinical trial as the outcome would likely be successful (Food and Drug Administration. Innovation or Stagnation: Challenge and Opportunity on the Critical Path to New Medical Products. 1-38. 2004). Many trials fail because of "noise" in the system, that is, clinical efficacy may be masked because of differences in patient characteristics between the control and the study group. If the proper patient group were chosen for study, a clinical trial may show benefit. Mathematical modeling would enable development to be focused on agents which are likely to be of benefit.

EXAMPLE 2

Vocal Fold Injury

Personalized medicine is a longstanding therapeutic goal in medicine. Agent-Based Models (ABMs) have previously been used to simulate inflammation at various scales up to the whole-organism level. We extended the ABM approach to a patient-specific ABM for vocal fold inflammation, with the goal of identifying individually optimized treatments. As shown below, ABM simulations reproduced trajectories of inflammatory mediators in laryngeal secretions of individuals subjected to experimental phonotrauma up to 4 hr post-injury, and predicted the levels of inflammatory mediators 24 hr post-injury. Subject-specific simulations also predicted different outcomes of behavioral treatment regimens to which subjects had not been exposed. This translational application of computational modeling could be used to design patient-specific therapy.

Methods

Experimental Protocol for Acute Phonotrauma in Different Treatment Modalities

A total of nine subjects participated in the study; six females (21-46 years) and three males (21-29 years). All nine subjects participated in a between-subjects study design, which involved exposure to one "treatment" condition (spontaneous speech, voice rest, and resonant voice "treatment") following a vocal loading task. The vocal loading task aimed to induce an acute phonotrauma or acute laryngeal inflammation. The protocol for vocal loading entailed three consecutive cycles, each involving 15 minutes of loud phonation (~75-90 dB @15 cm) followed by 5 minutes of silence, for a total 60 minutes.

Subjects would be excluded from the study if they had current voice problems and voice problem more than once a month over the past year. Also, known speech and/or language deficits would be excluded. However, childhood disorders were not exclusionary. Subjects would be excluded if they had current medications that were determined to possibly influence voice (e.g. diuretics, decongestants); and known or suspected allergy to anesthetics, especially lidocaine. Subjects would also be excluded if they were aware of any current or past speech and/or language disorders. Subjects should not have gag when they brush their teeth or have any knowledge of a heightened gag reflex. Subjects might be excluded if they had a deviated septum, depended on the otolaryngologist's decision.

Laryngeal Secretion Procedure and Assessment of Inflammatory Analytes

A total of 4 secretion specimens were collected from each subject 4 times per treatment condition—baseline, post vocal loading, 4 hours post-initiation of treatment and 24 hour post-baseline. An otolaryngologist examined the subject's oral cavity, oropharynx, and nasal cavity and placed a cotton pledget (a flat absorbent pad) soaked with lidocaine and decongestant into the subject's most patent nasal cavity. Cetocaine was sprayed in the oropharynx. Rigid laryngeal stroboscopy was performed to obtain a baseline stroboscopic evaluation on the patient. Then, 4% lidocaine was dripped onto the endolarynx through the working channel of the previously noted chip-tip flexible laryngoscope. After approximately 5 minutes, subsequent to verification of anesthesia to light touch, a one millimeter plastic cannula was passed through the working channel of the scope and guided down to the free edge and superior surface of the vocal folds while suction was applied to the catheter. That procedure allowed for the collection of a small amount of vocal fold secretions (about 100 µl), while minimizing contact of the scope with the vocal folds. Secretions were captured in a modified sinus trap and then transferred into a 0.2 ml microfuge tube via a 1 cc syringe. The tubes were labeled using codes that could not be traced to the subject or the subject's condition—except by way of a secret list retained by one investigator who was not involved with secretion data analysis—and the tubes were placed on dry ice. Tubes were then stored at −80° C. until analysis.

All secretion analyses were carried out by an investigator who was blinded to subjects' conditions (time point and treatment condition). For the analyses, a known volume was aliquoted for analysis and served as the dilution factor. The appropriate volume of sterile saline was added to the tube to bring the total volume up to 2.0 ml. Standard enzyme-linked immunosorbent assays (ELISAs) were performed for IL-1β, IL-6, IL-8, TNF-α, matrix metalloproteinase (MMP)-8, and IL-10 utilizing the manufacturer's recommended protocol (R&D Systems, Minneapolis, Minn.). In addition, IL-6 and IL-8 were also analyzed, as these cytokines are central mediators of inflammation. IL-10, an anti-inflammatory cytokine, was assayed to determine if anti-inflammatory cytokines are measurable in secretions and to determine if this cytokine may be a relevant indicator of tissue health. All samples were run on the same kit to avoid inter-kit variability.

ABM Development

Figure 11:
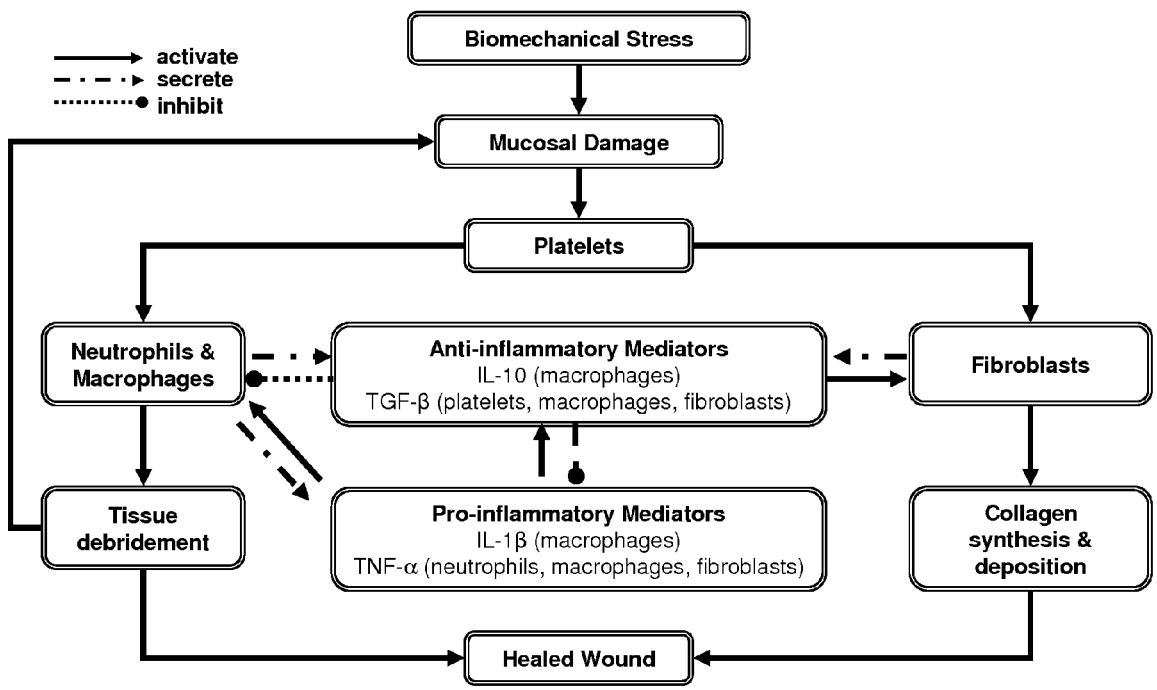
FIG. 11 provides an overall flowchart of one non-limiting embodiment of the phonotrauma ABM. The model assumes that biomechanical stress during phonation causes mucosal damage and activates platelets, neutrophils and macrophages. Platelets produce TGF-β1, which chemoattracts both neutrophils and macrophages. Activated neutrophils and macrophages secrete pro-inflammatory mediators, which in turn induce anti-inflammatory mediator release. Pro-inflammatory mediators also induce neutrophils and macrophages to produce free radicals that damage tissue. In the model, the activity of free radicals was subsumed in the actions of TNF-α. Anti-inflammatory mediators contribute to fibroblast activation. Activated fibroblasts secrete collagen that mediates tissue repair. In the model, collagen accumulation is considered as the surrogate for healing outcome following phonotrauma. Collagen is an important ECM protein involving both structural and biomechanical functions in the vocal folds.

The ABM of inflammation and tissue damage/healing was a modification of one we have developed previously to address the prototypical wound healing scenario, namely skin healing (Mi, Q.; Riviere, B.; Clermont, G.; Steed, D. L.; Vodovotz, Y. Agent-based model of inflammation and wound healing: insights into diabetic foot ulcer pathology and the role of transforming growth factor-β1. Wound Rep. Reg. 2007. 15:671-682). Netlogo® was used as the platform for model building and simulation. This first-generation ABM aimed to reproduce the basic and generally-accepted mechanisms of wound healing. Thus, detailed literature on inflammation and wound healing was reviewed to identify the essential components and rules for this ABM (FIG. 11) (Clark R A F (1998) Wound Repair. Overview and General Considerations. In: Clark R A F, editor. The Molecular and Cellular Biology of Wound Repair. New York: Plenum Press; Cockbill S (2002) Wound: the healing process. Hospital Pharmacist 9:

255-260; Martin P (1997) Wound Healing-aiming for perfect skin regeneration. Science 276: 75-81; Robson M C, Steed D L, Franz MG (2001) Wound healing: biologic features and approaches to maximize healing trajectories. Curr Probl Surg 38: 72-140 and Witte M B, Barbul A (1997) General principles of wound healing. Surgical Clinics of North America 77: 509-528). Then, experimental measures of inflammatory cytokines in human laryngeal secretions (Verdolini et al., in preparation) were used to specify the model to the setting of vocal fold injury.

Simply put, this ABM of phonotrauma represents processes thought to occur in the vocal fold mucosal tissue and to simulate the mucosal repair response to biomechanical damage during phonation. The model consists of platelets, inflammatory cells (neutrophils, macrophages, and fibroblasts), cytokines that mediate inflammation and wound healing (IL-1β, TNF-α, IL-10, and TGF-β1), a representative component of the extracellular matrix (collagen), and, perhaps most important, a tissue damage function functionally analogous to alarm/danger signals (Matzinger P (2002) The danger model: a renewed sense of self. Science 296: 301-305) that produces positive feedback to induce further inflammation (Vodovotz Y (2006) Deciphering the complexity of acute inflammation using mathematical models. Immunol Res 36: 237-245) (Table 3).

TABLE 3

Summary of the components involved in the ABM.

| Cell | Substance | Biological function in wound healing used in ABM |
|---|---|---|
| Platelet Macrophage Fibroblast | TGF-beta | Chemotactic to neutrophils, macrophages and fibroblasts<br>Inhibit expression of TNF-alpha in neutrophils, macrophages and fibroblasts<br>Inhibit expression of IL-1 beta in macrophages (minimal effect)<br>Stimulate resting fibroblasts to activated fibroblasts<br>Mitogenic to fibroblasts (proliferation)<br>Stimulate collagen synthesis in fibroblasts |
| Neutrophil Macrophage Fibroblasts | TNF-alpha | Chemotactic to neutrophils and macrophages<br>Activate neutrophils and macrophages<br>Stimulate expression of TNF-alpha and IL-1 beta in macrophages<br>Stimulate expression of TGF-beta in macrophages and fibroblasts<br>Mitogenic to fibroblast (proliferation) |
| Macrophage | IL-1 beta | Chemotactic to neutrophils and macrophages<br>Activate macrophages<br>Stimulate expression of TNF-alpha and IL-1 beta in macrophages<br>Mitogenic to fibroblasts (proliferation)<br>Inhibit collagen synthesis in fibroblasts |
| Macrophage | IL-10 | Inhibit expression of TNF-alpha in neutrophils, macrophages and fibroblasts<br>Inhibit expression of IL-1 beta in macrophages<br>Stimulate expression of TGF-beta in macrophages and fibroblasts<br>Stimulate expression of IL-10 in macrophages<br>Inhibit activated neutrophil survival<br>Inhibit activation of neutrophils and macrophages |
| Fibroblast | Collagen | Tissue repair |

Regions, patches and agents of the vocal fold ABM

A typical ABM is composed of three elements: region, patch and agent. The region is composed of small patches. The patches are immobile components that characterize the physical-spatial environment, where the agents operate. Agents are the active objects that move and interact within the region. In our ABM, our "world" is a square grid, 120×120 patches, with origin in the center of the grid. Two regions were created to simulate (1) blood and (2) the mucosal tissue itself. These two regions do not intersect. Specifically, the tissue region is a circle of diameter 55 centered at the origin and bounded by the blood region. The blood region is the source of the inflammatory cells that infiltrate the wounded tissue. At the same time, the region of mucosal tissue is the source of some resident cells and is also the site that phonotraumatic injury occurs and subsequently repaired by the fibroblasts (Mi, Q.; Riviere, B.; Clermont, G.; Steed, D. L.; Vodovotz, Y. Agent-based model of inflammation and wound healing: insights into diabetic foot ulcer pathology and the role of transforming growth factor-1. Wound Rep. Reg. 2007. 15:671-682).

Patch variables were used to represent (1) tissue status (healthy, damaged, and healed); (2) platelets; (3) collagen; and (4) inflammatory mediators. Platelets are important to initiate the inflammatory process following tissue damage. The initial number of platelets is spatially distributed based on the rules in our model. Collagen is the major structural protein in the vocal folds and its content and organization are prone to be disturbed following repetitive phonotrauma. In our model, the amount of collagen was required not to exceed the existing amount of damage in the same patch. Two pro-inflammatory mediators (IL-1β and TNF-α) and two anti-inflammatory mediators (IL-10 and TGF-β1) were also selected as patches because they are generally believed to play an important role in wound healing environment and because we had prior data on their expressions in vocal folds (Branski R C, Verdolini K, Rosen C A, Hebda P A (2004) Markers of wound healing in vocal fold secretions from patients with laryngeal pathology. Annals of Otology, Rhinology, and Laryngology 113: 23-29; Verdolini K, Rosen C A, Branski R C, Hebda P A (2003) Shifts in biochemical markers associated with wound healing in laryngeal secretions following phonotrauma: A preliminary study. Annals of Otology, Rhinology, & Laryngology 112: 1021-1025 and Branski R C, Rosen C A, Verdolini K, Hebda P A (2005) Biochemical markers associated with acute vocal fold wound healing: a rabbit model. J Voice 19: 283-289). The concentrations of the inflammatory mediators on each patch are controlled by the formulae of mediator synthesis, mediator degradation and mediator diffusion.

Agent variables were used to represent (1) tissue damage and (2) cells. Tissue damage is induced by the initial injury and the subsequent inflammatory response of the pro-inflammatory mediators (IL-1β and TNF-α). Tissue damage also acts as a stimulus for further inflammation. Another class of agent is cells, namely, neutrophils, macrophages and fibroblasts. In our model, cells have three states: resting, activated or dead. Cells are represented as agents because they can be organized based on common behavioral rules, and because the response of a particular cell type to various mediators is readily characterized in the literature (An G (2004) In silico experiments of existing and hypothetical cytokine-directed clinical trials using agent-based modeling. Critical Care Medicine 32: 2050-2060). Cell behavior was governed by rules based on existing wound healing literature. Depending on the cell type, the cellular responses included activation, migration, proliferation, cell death, secretion of inflammatory mediators, tissue debridement, and collagen generation. The complete rules of the ABM with explanations are presented in Table 4.

TABLE 4

| Parameter Description | Rule |
|---|---|
| Extent of mucosal damage created by custom-defined magnitude | Initial damage = Magnitude * Magnitude |
| Extent of mucosal damage induced by TNF-α | If TNF-α > 0.1, damage + 1 |
| Effect of the 4-hr tissue mobilization exercise on mucosa | If the time step is between 1 and 3, create a damage = 10 |
| Effect of the 4-hr tissue mobilization exercise on mucosa | If the time step is between 1 and 3, create a damage = 30 |
| TGF-β secreted by platelets | TGF-β = TGF-β + number of platelet/10 |
| Platelet diffusion coefficient | Platelet = 1 unit/step |
| Inflammatory mediator diffusion speed | IL-1β = 1 unit/step<br>TNF-α = 1 unit/step<br>TGF-β = 1 unit/step<br>IL-10 = 1 unit/step |
| Collagen diffusion coefficient | 0.5 unit/step |
| Inflammatory mediator degradation speed | IL-1β = 0.2 unit/step<br>TNF-α = 0.2 unit/step<br>TGF-β = 0.2 unit/step<br>IL-10 = 0.25 unit/step |
| Collagen degradation coefficient | 0.99 unit/step |
| Collagen healed damage | If collagen > 1, the damaged tissue that is healed underneath the collagen. |
| Initial number of neutrophils | 60 |
| Number of neutrophils recruited relating to damage | 2 * (damage/magnitude$^2$) + 1 |
| Platelets chemoattract neutrophils | If platelet$_{right}$ > platelet$_{ahead}$ and platelet$_{right}$ > platelet$_{left}$, neutrophil turns 90° right.<br>If platelet$_{left}$ > platelet$_{right}$, neutrophil turns 90° left. |
| TNF-α chemoattracts neutrophils | If TNF-α$_{right}$ > TNF-α$_{ahead}$ and TNF-α$_{right}$ > TNF-α$_{left}$, neutrophil turns 90° right.<br>If TNF-α$_{left}$ > TNF-α$_{right}$, neutrophil turns 90° left. |
| TGF-β chemoattracts neutrophils | If TGF-β$_{right}$ > TGF-β$_{ahead}$ and TGF-β$_{right}$ > TGF-β$_{left}$, neutrophil turns 90° right.<br>If TGF-β$_{left}$ > TGF-β$_{right}$, neutrophil turns 90° left. |
| IL-1β chemoattracts neutrophils | If IL-1β$_{right}$ > IL-1β$_{ahead}$ and IL-1β$_{right}$ > IL-1β$_{left}$, neutrophil turns 90° right.<br>If IL-1β$_{left}$ > IL-1β$_{right}$, neutrophil turns 90° left. |
| Area of mucosal damage that activates neutrophils | If neutrophil migrates to the area that has the damage greater than (magnitude + total-damage * 2), neutrophil is activated |
| TNF-α (and IL-10) stimulates (and inhibits) activation of neutrophils | If TNF-α − (IL-10 * 5000) > 0.1, neutrophil is activated |
| TNF-α secreted by activated neutrophil | TNF-α = TNF-α + (0.1 * (1/(TGF-β * 0.5 + IL-10 * 5)) |
| Activated neutrophil lifespan | 2 to 4 days |
| IL-10 inhibits activated neutrophil survival | If total-IL-10 > 1, activated neutrophil age − 0.5 |
| Initial number of residential macrophages | 120 |
| Magnitude of damage to recruit resting macrophage | If damage > magnitude * 1.2, resting macrophage will be recruited |
| Number of macrophages recruited relating to damage | 4 * damage/magnitude$^2$ + 1 |
| Platelets chemoattract macrophages | If platelet$_{right}$ > platelet$_{ahead}$ and platelet$_{right}$ > platelet$_{left}$, macrophage turns 90° right.<br>If platelet$_{left}$ > platelet$_{right}$, macrophage turns 90° left. |
| TNF-α chemoattracts macrophages | If TNF-α$_{right}$ > TNF-α$_{ahead}$ and TNF-α$_{right}$ > TNF-α$_{left}$, macrophage turns 90° right.<br>If TNF-α$_{left}$ > TNF-α$_{right}$, macrophage turns 90° left. |
| TGF-β chemoattracts macrophages | If TGF-β$_{right}$ > TGF-β$_{ahead}$ and TGF-β$_{right}$ > TGF-β$_{left}$, macrophage turns 90° right.<br>If TGF-β$_{left}$ > TGF-β$_{right}$, macrophage turns 90° left. |
| IL-1β chemoattracts macrophages | If IL-1β$_{right}$ > IL-1β$_{ahead}$ and IL-β$_{right}$ > IL-1β$_{left}$, macrophage turns 90° right.<br>If IL-1β$_{left}$ > IL-1β$_{right}$, macrophage turns 90° left. |
| Area of mucosal damage that activates macrophages | If macrophage migrates to the area that has the damage greater than (magnitude + total-damage) * 0.01, macrophage is activated |
| IL-1β, TNF-α (and IL-10) stimulates (and inhibits) activation of macrophages | If IL-1β + TNF-α − IL-10 > 400, macrophage is activated |
| Inflammatory mediators secreted by activated macrophages under voice rest condition | TNF-α = TNF-α + 0.1 * (1/(1 + TGF-β + total-IL-10)) * (1 + total-TNF-α + total-IL-1beta + 40)<br>IL-1β = IL-1β + 1 * (1/(1 + TGF-β + total-IL-10)) * (1 + total-TNF-α * 30 + total-IL-1beta + 40)<br>IL-10 = IL-10 + 2 + (total-IL-10 * 0.001)<br>TGF-β = TGF-β + (1 + total-IL-10 + total-TNF-α) |
| Inflammatory mediators secreted by activated macrophages under tissue mobilization condition | TNF-α = TNF-α + 0.1 * (1/(1 + TGF-β + total-IL-10)) * (1 + total-TNF-α + total-IL-1beta * 0.5 + 40)<br>IL-1β = IL-1β + 1 * (1/(1 + TGF-β + total-IL-10)) * (1 + total-TNF-α * 10 + total-IL-1beta + 40)<br>IL-10 = IL-10 + 1 + (total-IL-10 * 0.01)<br>TGF-β = TGF-β + (1 + total-IL-10 + total-TNF-α) |

TABLE 4-continued

| Parameter Description | Rule |
|---|---|
| Inflammatory mediators secreted by activated macrophages under spontaneous speech condition | TNF-α = TNF-α + 0.1 * (1/(1 + TGF-β + total-IL-10)) * (1 + total-TNF-α + total-IL-1beta * 0.5 + 40)<br>IL-1β = IL-1β + 1 * (1/(1 + TGF-β * 0.8 + total-IL-10)) * (1 + total-TNF-α * 50 + total-IL-1beta + 40)<br>IL-10 = IL-10 + 1.5 + (total-IL-10 * 0.001)<br>TGF-β = TGF-β + (1 + total-IL-10 + total-TNF-α) |
| Time period that macrophages killed neutrophils | During 3.8-4.8 day post-jury |
| Probability of macrophages killing neutrophils | 90% chance after 4-5 post-damage days |
| Macrophage lifespan | 5-9 days |
| Initial number of residential fibroblasts | 250 |
| Magnitude of damage to recruit tissue fibroblasts | If damage > magnitude * 1.2, tissue fibroblasts will be recruited. |
| Number of tissue fibroblasts being recruited related to damage | 4 * damage/magnitude$^2$ + 1 |
| TGF-β chemoattracts tissue fibroblasts | If TGF-$β_{right}$ > TGF-$β_{ahead}$ and TGF-$β_{right}$ > TGF-$β_{left}$, tissue fibroblast turns 90° right.<br>If TGF-$β_{left}$ > TGF-$β_{right}$, tissue fibroblast turns 90° left. |
| Tissue fibroblasts differentiate to activated fibroblasts | If tissue fibroblast migrates to the area that has the damage greater than TGF-β > 0.1, tissue fibroblasts differentiate to activated fibroblast. |
| Proliferation of activated fibroblasts | If activated fibroblast ages 3-13 days, fibroblast proliferates |
| Number of proliferated fibroblasts that are stimulated by IL-1β, TNF-α and TGF-β | 1 + 0.001 * (total-TGF * 0.5 + total-TNF * 0.5 + total-IL-1beta * 0.5) |
| Inflammatory mediators secreted by activated fibroblasts | TNF-α = TNF-α + 0.2 * (1/(1 + total-TGF-β + total-IL-10))<br>TGF-β = TGF-β + (1 + total-TNF-α * 0.5 + total-IL-10 * 0.5) |
| Collagen secreted by activated fibroblasts | Collagen = Collagen + 2 * (1 + total-TGF-β * 2)/(1 + total-IL-1β * 0.5) |
| Fibroblast lifespan | 3-5 days |

Simulation of Acute Phonotrauma

For each simulation, the user can define the initial levels of IL-1β, TNF-α and IL-10, add a phonotrauma event, and then a 4-hr treatment event (voice rest, "resonant voice" exercise or spontaneous speech). We assumed in the model that one step of simulated time represents 0.1 days or approximately 2.4 hours. The changes in temporal concentration of inflammatory cells, mediators, tissue damage and collagen were plotted and refolded into the model at each time step.

Initially, some resting neutrophils, macrophages, and fibroblasts are present with a random distribution in both blood and tissue regions. Simulated phonatory stresses traumatized the mucosal tissue in the middle of region and the model will initiate platelet degranulation. Shortly afterwards, a chemoattractant gradient is created that stimulates the infiltration and activation for neutrophils and macrophages. Later on, fibroblasts are activated by tissue damage and TGF-β1. Fibroblasts secrete collagen to repair both the initial and inflammation-induced damage. Lastly, additional mechanical stresses will be applied to the traumatized tissue based on the treatment selected (voice rest: no additional mechanical stress; resonant voice: low mechanical stress; spontaneous speech: high mechanical stress).

Model Calibration and Validation

Standard procedures to evaluate the fit of ABM to empirical data have not been established in the literature. In the present study, pattern-oriented analysis (Railback S F (2001) Getting "results": the pattern-oriented approach to analyze natural systems with individual-based models. Natural Resource Modeling 14: 465-474) was used to estimate the conformity of simulation-generated data curves with the inflammatory and wound healing patterns reported in the literature as well as the empirical data sets around acute phonotrauma (Table 5).

TABLE 5

Patterns used for ABM at the "comparison condition," i.e., the mid-point of the magnitude of initial mechanical stress input.

| Validation Patterns | Resource |
|---|---|
| Neutrophil arrives in wound site in the first few hours | a, b, c, d |
| Neutrophil number is at maximum by 24 hours | a, b, c, d |
| Neutrophil number decreases rapidly on Day 3 | a, b, c, d |
| Macrophage number is at maximum by 24-48 hours | a, b, c, d |
| Fibroblast number is at maximum by Day 5-7 | a, b, c, d |
| Fibroblast number decreases gradually on Day 7 | a, b, c, d |
| Collagen curve is sigmoid-shaped | c, d | a. Cockbill S (2002) Wound: the healing process. Hospital Pharmacist 9: 255-260
b. Martin P (1997) Wound Healing-aiming for perfect skin regeneration. Science 276: 75-81
c. Robson MC, Steed DL, Franz MG (2001) Wound healing: biologic features and approaches to maximize healing trajectories. Curr Probl Surg 38: 72-140
d. Witte MB, Barbul A (1997) General principles of wound healing. Surgical Clinics of North America 77: 509-528

Figure 12:
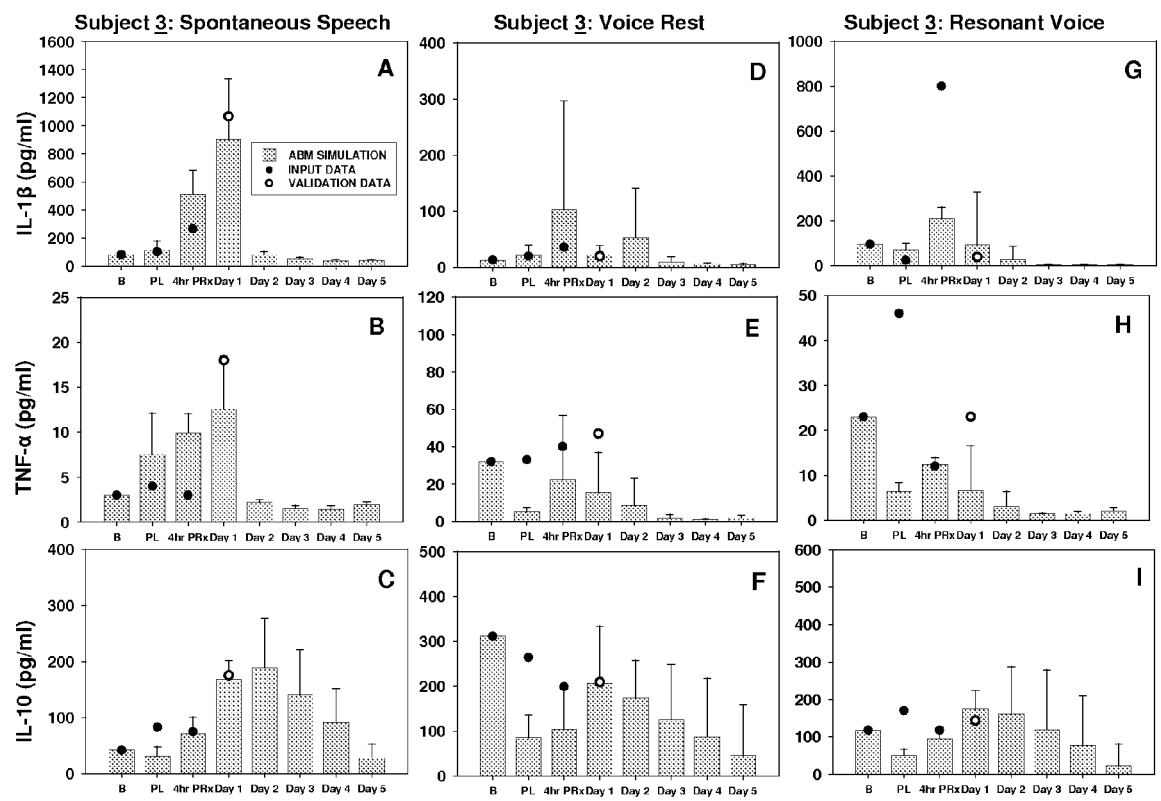
FIG. 12 shows predictions of inflammatory and wound healing responses to acute phonotrauma in a single human subject (Subject A) following spontaneous speech (Panels A-C), voice rest (Panels D-F) and resonant voice (Panels G-I). Panels A, D and G are the predicted cytokine trajectories of IL-1β. Panels B, E and H are the predicted cytokine trajectories of TNF-α. Panels C, F and I are the predicted cytokine trajectories of IL-10. Inflammatory marker concentrations are in pg/ml. The grey bars represent the simulated data. The dark circles represent the input data of the first three time-points (baseline, post-loading, 4-hr post treatment) from the human laryngeal secretion data. The empty circles represent the validation data of the 24-hr time point from the human laryngeal secretion data (i.e., predictions of the model tested against data that were withheld from the model calibration procedure).
Figures 1, 12:
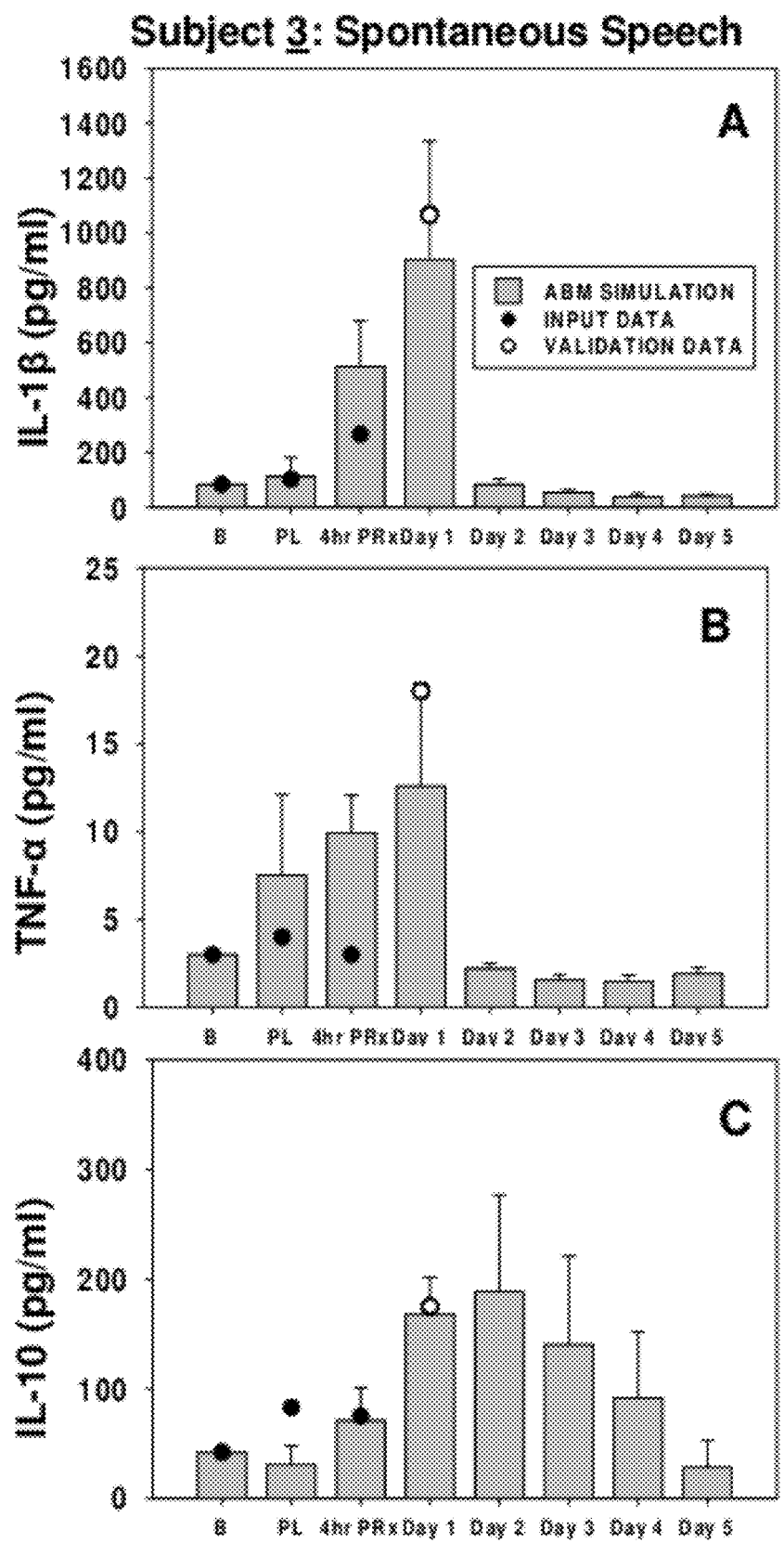
Figures 2, 12:
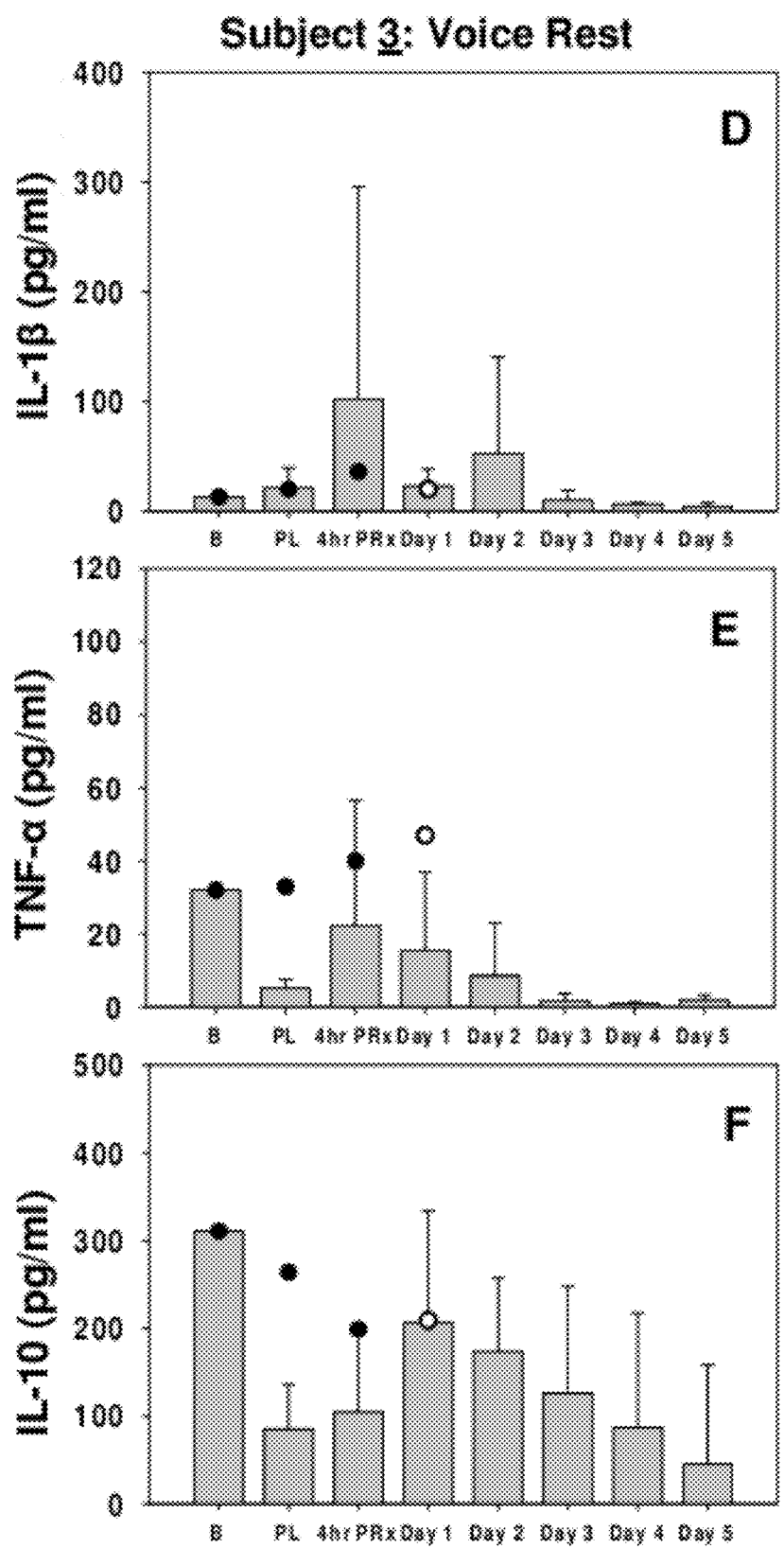
Figures 3, 12:
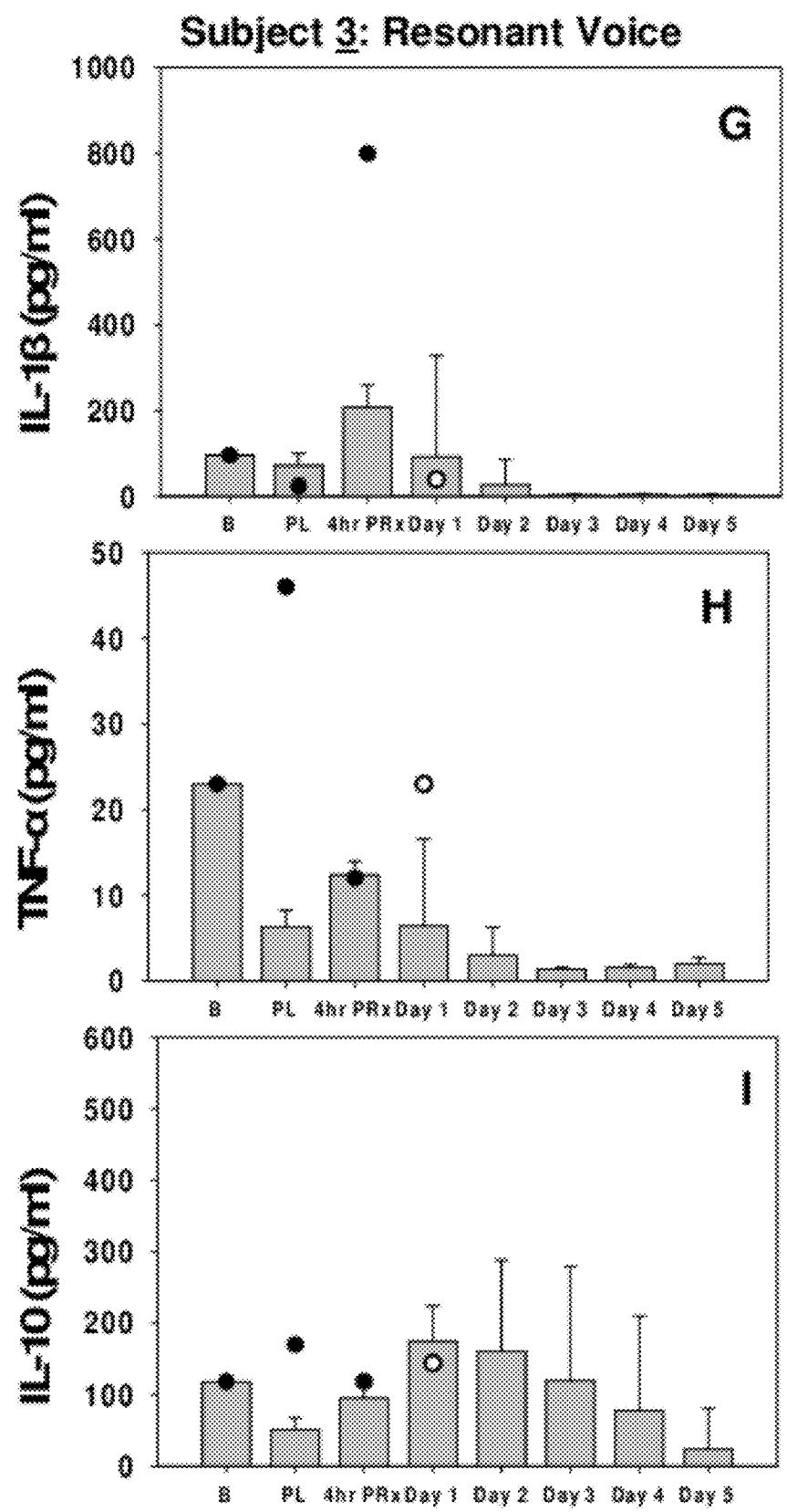
Figure 13:
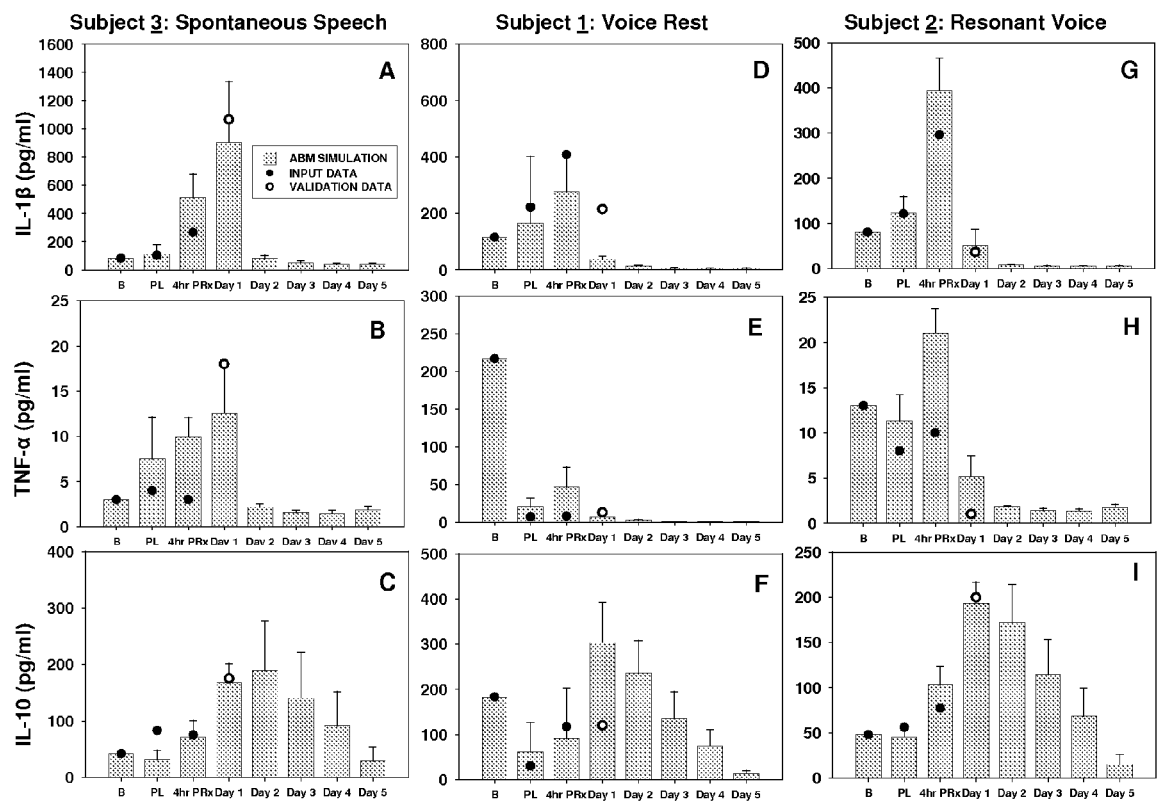
FIG. 13 provides predictions of inflammatory and wound healing responses to acute phonotrauma in three human subjects following spontaneous speech (Subject A; Panels A-C), voice rest (Subject B; Panels D-F) and resonant voice (Subject C; Panels G-I). Panels A, D and G are the predicted cytokine trajectories of IL-1β. Panels B, E and H are the predicted cytokine trajectories of TNF-α. Panels C, F and I are the predicted cytokine trajectories of IL-10. Inflammatory marker concentrations are in pg/ml. The grey bars represent the simulated data. The dark circles represent the input data of the first three time-points (baseline, post-loading, 4-hr post treatment) from the human laryngeal secretion data. The empty circles represent the validation data of the 24-hr time point from the human laryngeal secretion data (i.e., predictions of the model tested against data that were withheld from the model calibration procedure).
Figures 1, 13:
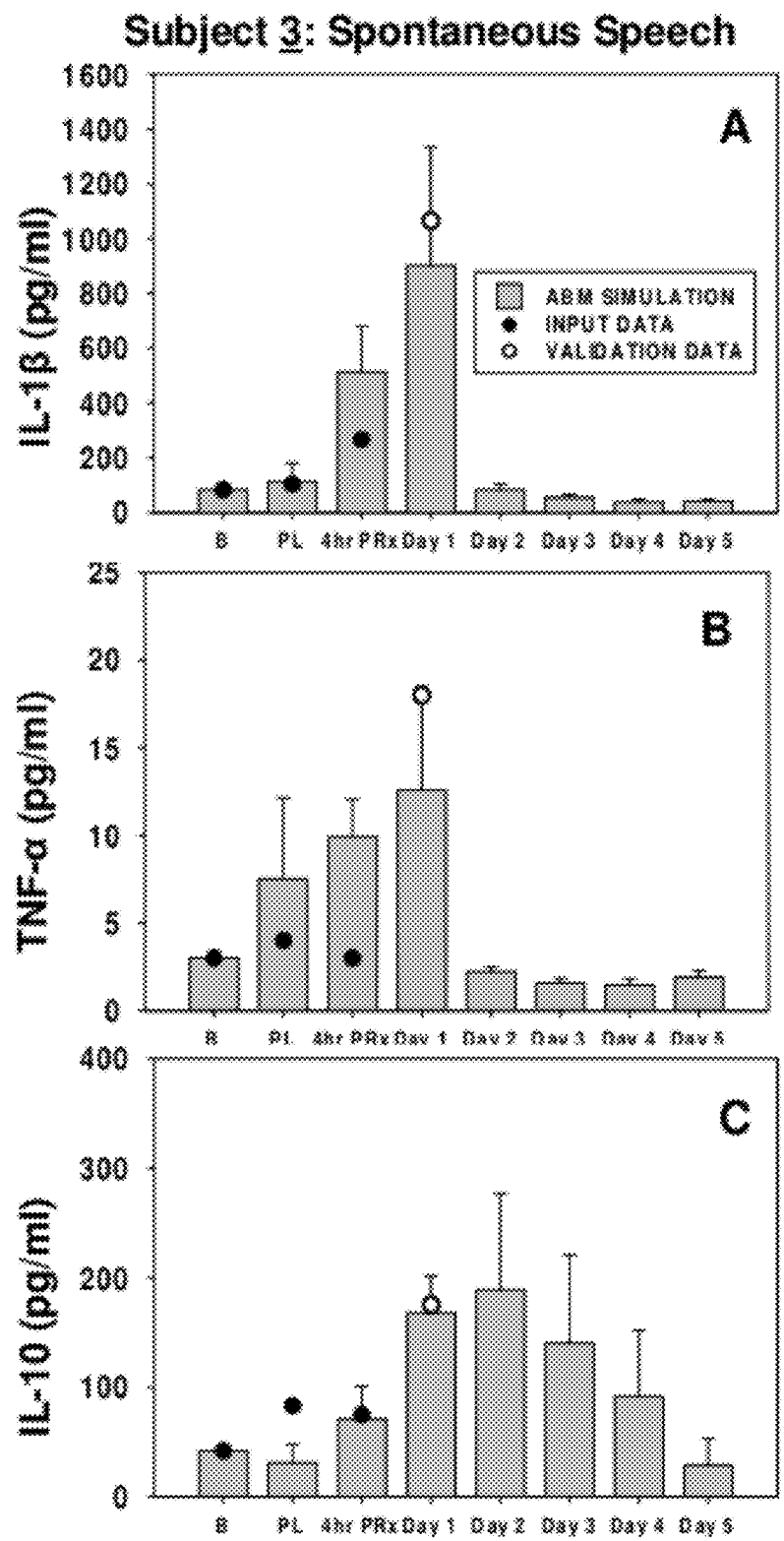
Figures 2, 13:
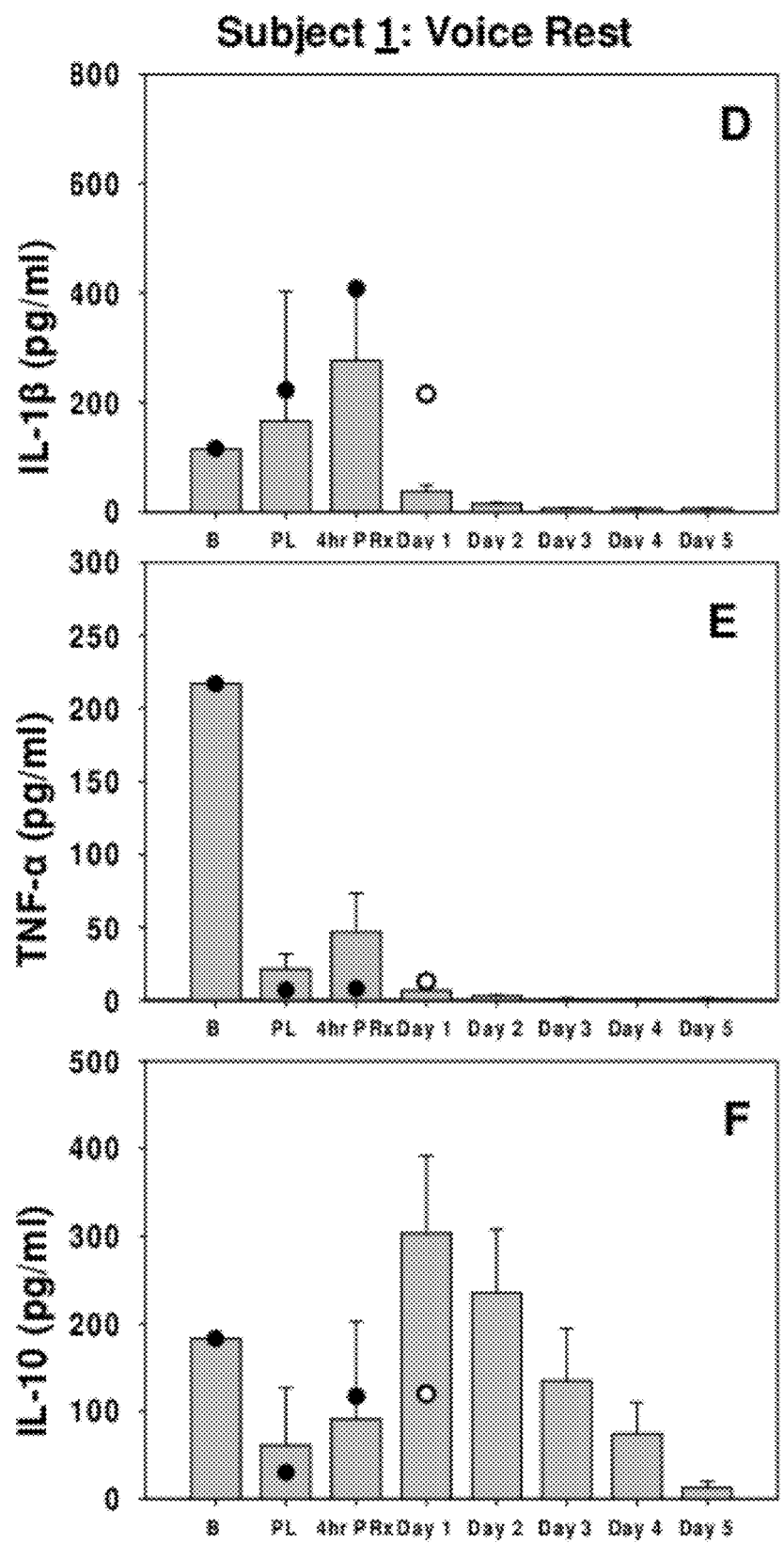
Figures 3, 13:
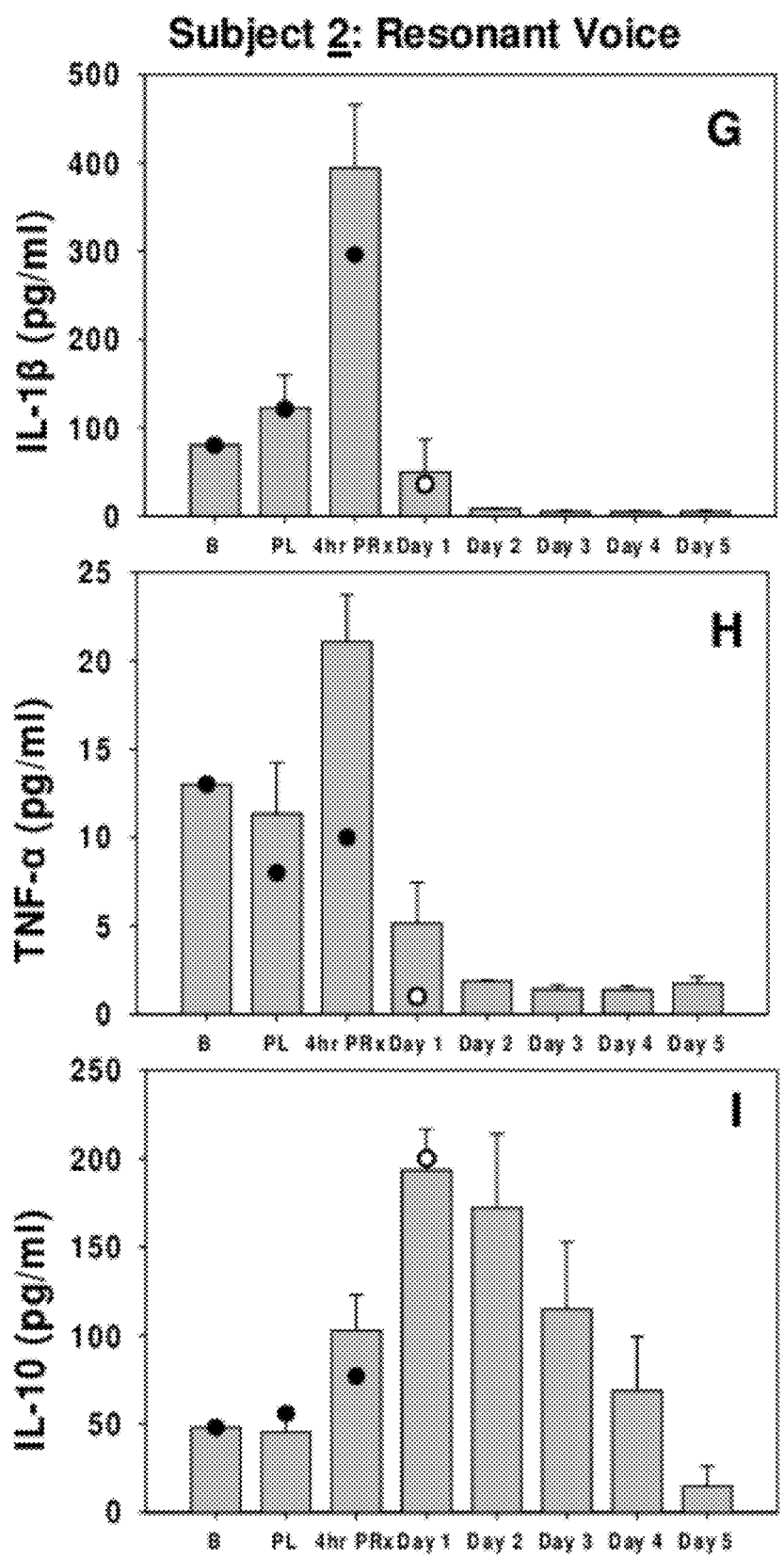

Using this approach, the user-defined initial magnitude of mucosal injury (range 0-40 in arbitrary units of damage) was set at a value of 20 as a "comparison condition," because that setting resulted in realistic predictions of mucosal damage and healing when compared with the general consensus around wound healing documented in literature (Cockbill S (2002) Wound: the healing process. Hospital Pharmacist 9: 255-260; Martin P (1997) Wound Healing-aiming for perfect skin regeneration. Science 276: 75-81; Robson M C, Steed D L, Franz M G (2001) Wound healing: biologic features and approaches to maximize healing trajectories. Curr Probl Surg 38: 72-140 and Witte M B, Barbul A (1997) General principles of wound healing. Surgical Clinics of North America 77: 509-528). Where qualitative behavior of the simulation appeared satisfactory, the model was calibrated by adjusting parameter values not found in the literature to fit the quantity and time-course of measured vocal fold mediators. The ABM was calibrated using data from three human subjects (Subjects A, B and C) of their baseline cytokine levels in laryngeal fluid, immediately after phonotrauma induction, and following a 4-hr treatment (voice rest, "tissue mobilization exercises," or spontaneous speech) (FIGS. 12 and 13, dark circles).

Specifically, Subject A was the only participant who was experimentally involved in all three treatment modalities. Subjects B and C were from the groups of voice rest and "resonant voice" respectively. These three subjects were chosen for model calibration because their data for the inflammatory mediators were considered as "valid" to give reliable analysis of the treatment effects following acute phonotrauma. Essentially, these data satisfied presuppositions "normal" baseline (derived from our data set) or increased in inflammatory mediator concentrations immediately post vocal loading. For the other six subjects in the experimental protocol, their data were not used for model calibration because the data for many of their mediators fell into "pre-inflamed", "non-responsive" and "invalid" categories. "Pre-inflamed" data referred to the mediator that showed high baseline concentrations of pro-inflammatory markers ($\geq 1$ standard deviation from our data set). "Non-responsive" data referred to the mediator that showed normal baseline concentrations of markers (<1 standard deviation from our data set), but paradoxically decreasing post loading. Lastly, a limited number of data points were considered as "invalid" due to thick secretions that compromised any believable results from the ELISA.

Due to the inherent stochasticity of the ABM framework, we performed ten runs of the calibrated ABM up to five simulated days under the condition of (1) each subject's original treatment group and (2) the effect of randomization to either of the other two treatment groups for all 9 human subjects. Again, Subject A was the only subject who originally involved in all three treatment groups. Moreover, only the cytokine levels of the first three time points from Subjects A-C were used for model calibration. The means and standard deviations of model variables (concentrations of inflammatory cells, mediators, and tissue damage) were computed at each time point for subsequent analysis. To validate the ABM, the predicted cytokine levels were compared with the empirical cytokine levels at 24 hr for each subject.

Statistical Analysis

First, a generalized linear mixed model for repeated measures was used to compare the predicted levels of IL-1β, TNF-α, IL-10 and tissue damage for each time point across the three treatment conditions (spontaneous speech, voice rest and resonant voice) post-phonotrauma. Second, binomial testing was carried out to compare the human empirical data and the model predicted data of IL-1β, TNF-α, IL-10 at the 24-hr time point.

Results

FIGS. 12 and 13 display both predicted and empirical mediator trajectories for each subject's original treatment group for Subjects 1-3. FIG. 12 represents the data of the within-single subject, i.e., Subject 3, following the three treatment programs. FIG. 13 represents the between-group data, i.e., Subject 3 for the spontaneous speech group, Subject 1 for the voice rest group and Subject 2 for the "resonant voice" exercise group. In panels A-I, the dark circles represent data on inflammatory mediators used for calibration of each patient-specific ABM, while the empty circles represent data withheld from the model and used for comparison to model prediction.

Figure 14:
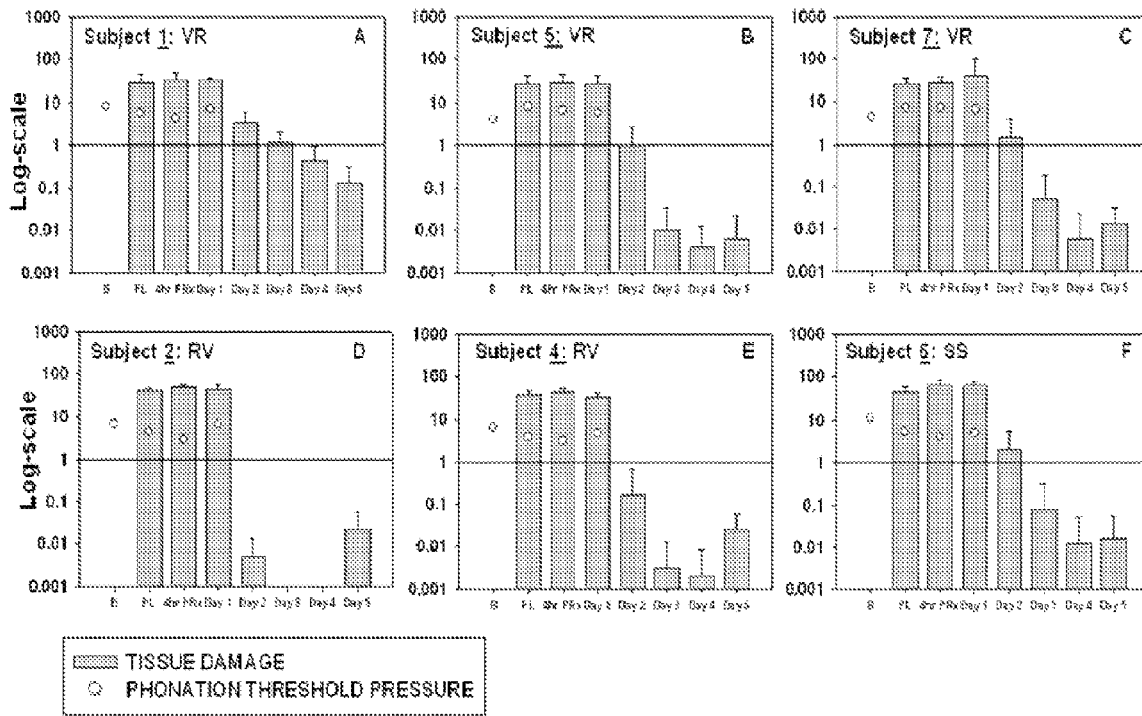
FIG. 14. Human data of phonation threshold pressure (cm/$H_2O$ in log scale) and predictions of simulated tissue damage (arbitrary unit in log scale) following acute phonotrauma in six subjects following voice rest (Subject 1: Panel A; Subject 5: Panel B; Subject 7: Panel C), resonant voice (Subject 2: Panel D; Subject 4: Panel E) and spontaneous speech (Subject 6; Panels F). The grey bars represent the means from the simulated data of tissue damage, and the error bars represent the standard deviation from the simulated data of tissue damage. The empty circles represent the validation data of the four time-points (baseline, post vocal loading, following a 4-hr treatment and 24-hr post baseline) from the clinical measure of phonation threshold pressure in the human subjects. B: baseline; PL: post vocal loading; 4 hrPRx: following a 4-hr treatment. Note that validation data for Days 2-5 have not yet been generated.

FIG. 14 shows human data of phonation threshold pressure ($cm/H_2O$ in log scale) and predictions of simulated tissue damage (arbitrary unit in log scale) following acute phonotrauma in six subjects following voice rest (Subject 1: Panel A; Subject 5: Panel B; Subject 7: Panel C), resonant voice (Subject 2: Panel D; Subject 4: Panel E) and spontaneous speech (Subject 6; Panels F). The grey bars represent the means from the simulated data of tissue damage, and the error bars represent the standard deviation from the simulated data of tissue damage. The empty circles represent the validation data of the four time-points (baseline, post vocal loading, following a 4-hr treatment and 24-hr post baseline) from the clinical measure of phonation threshold pressure in the human subjects. B: baseline; PL: post vocal loading; 4 hrPRx: following a 4-hr treatment. Note that validation data for Days 2-5 have not yet been generated.

Figure 15:
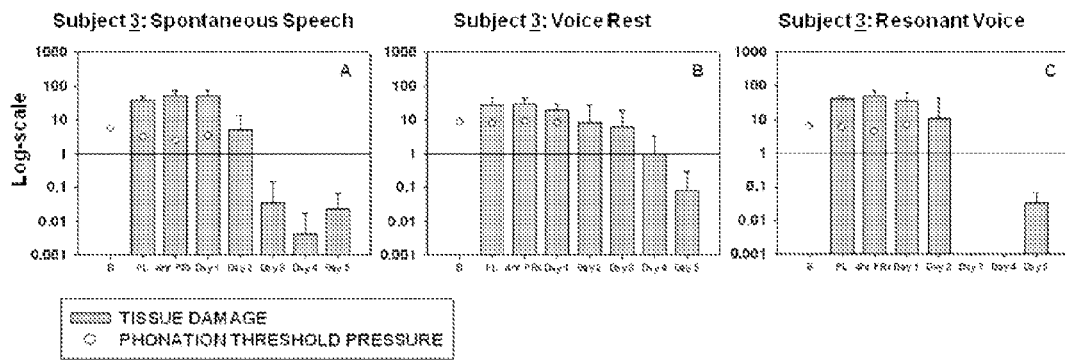
FIG. 15. Human data of phonation threshold pressure (cm/ $H_2O$ in log scale) and predictions of simulated tissue damage (arbitrary unit in log scale) following acute phonotrauma in a single human subject (Subject 3) following spontaneous speech (Panel A), voice rest (Panel B) and resonant voice (Panel C). The grey bars represent the predictions of simulated tissue damage. The empty circles represent the validation data of the four time-points (baseline, post vocal loading, following a 4-hr treatment and 24-hr post baseline) from the clinical measure of phonation threshold pressure in the human subjects. B: baseline; PL: post vocal loading; 4 hrPRx: following a 4-hr treatment.
Figures 1, 14:
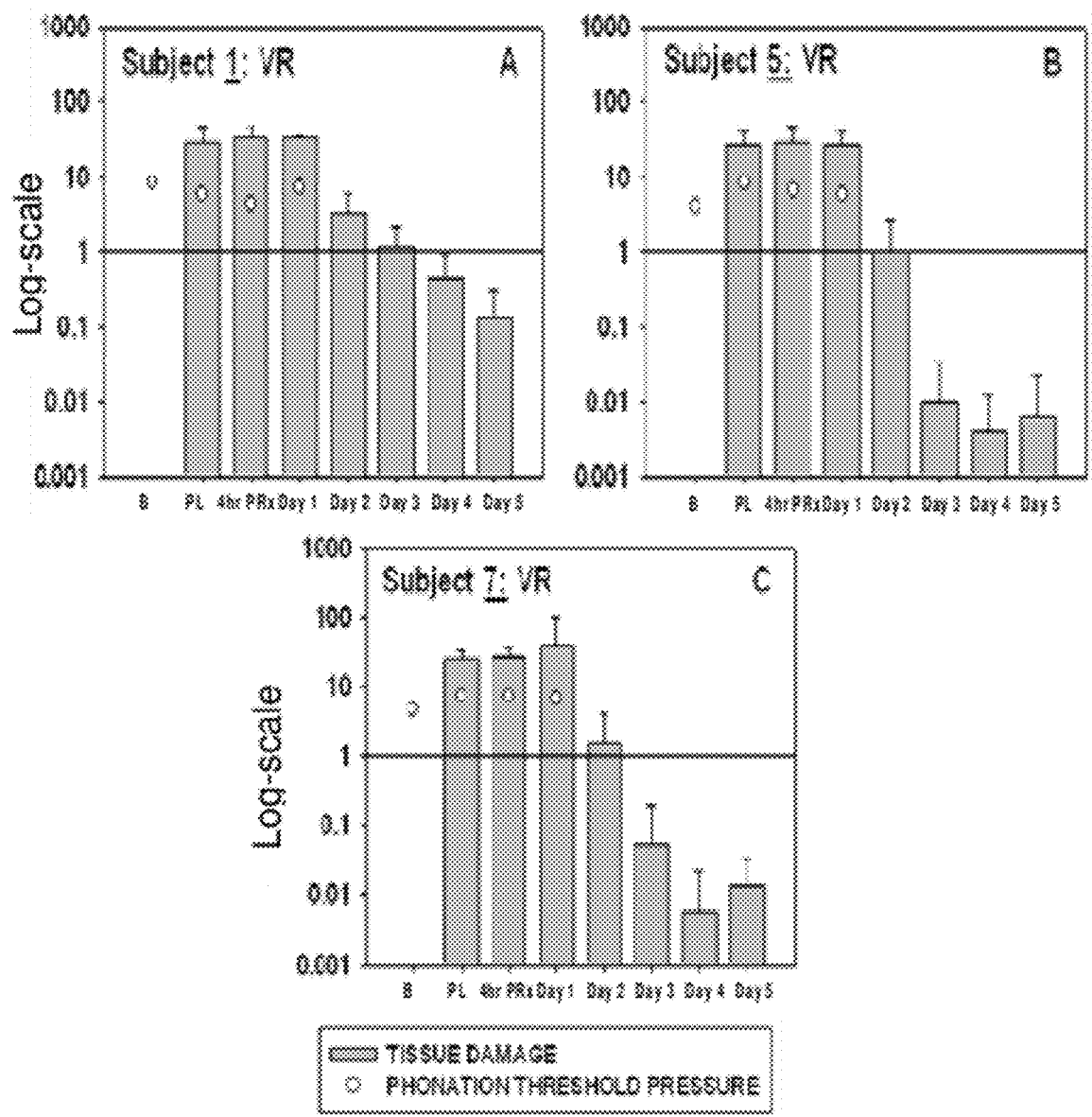
Figures 2, 14:
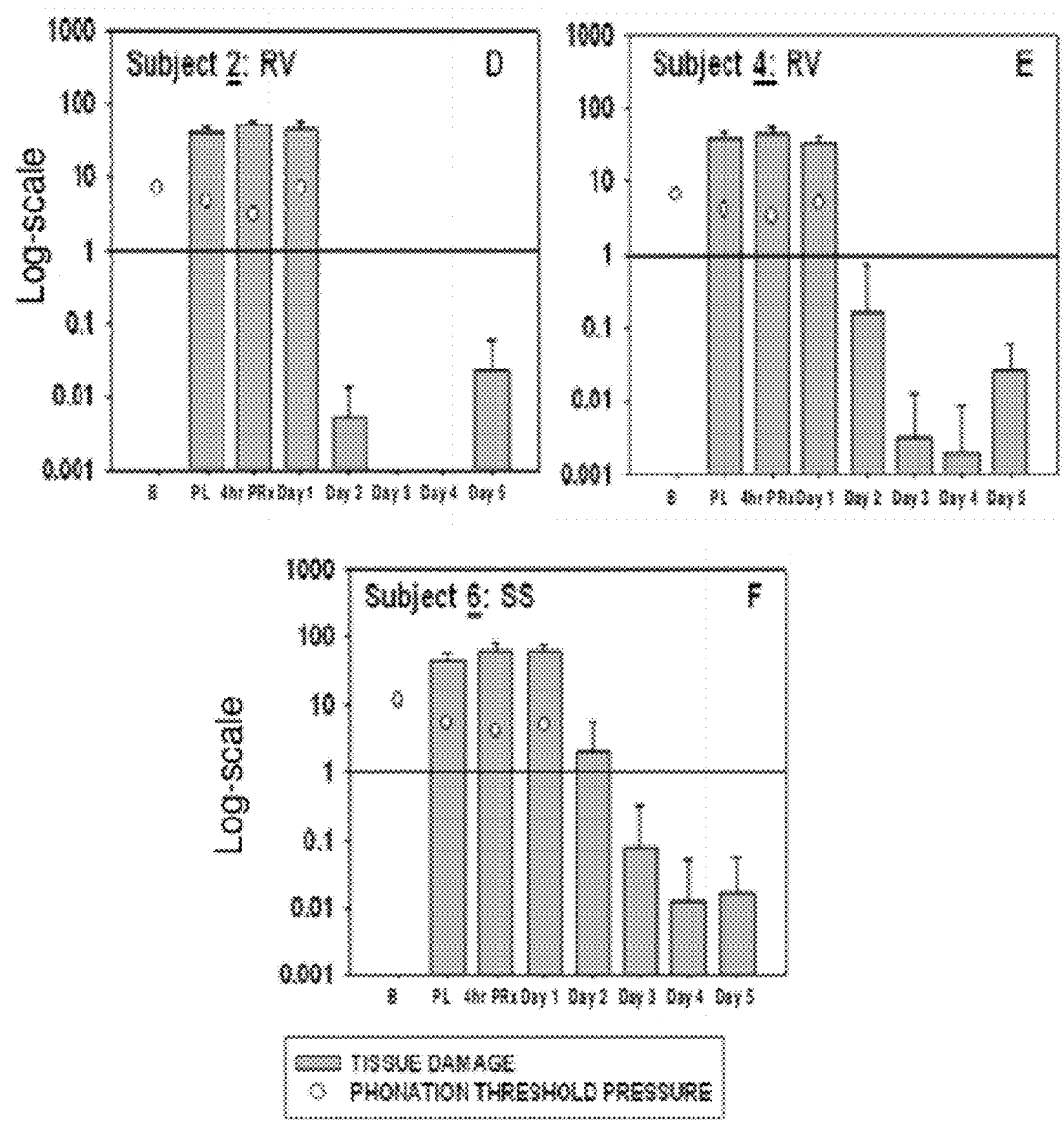
Figure 15:
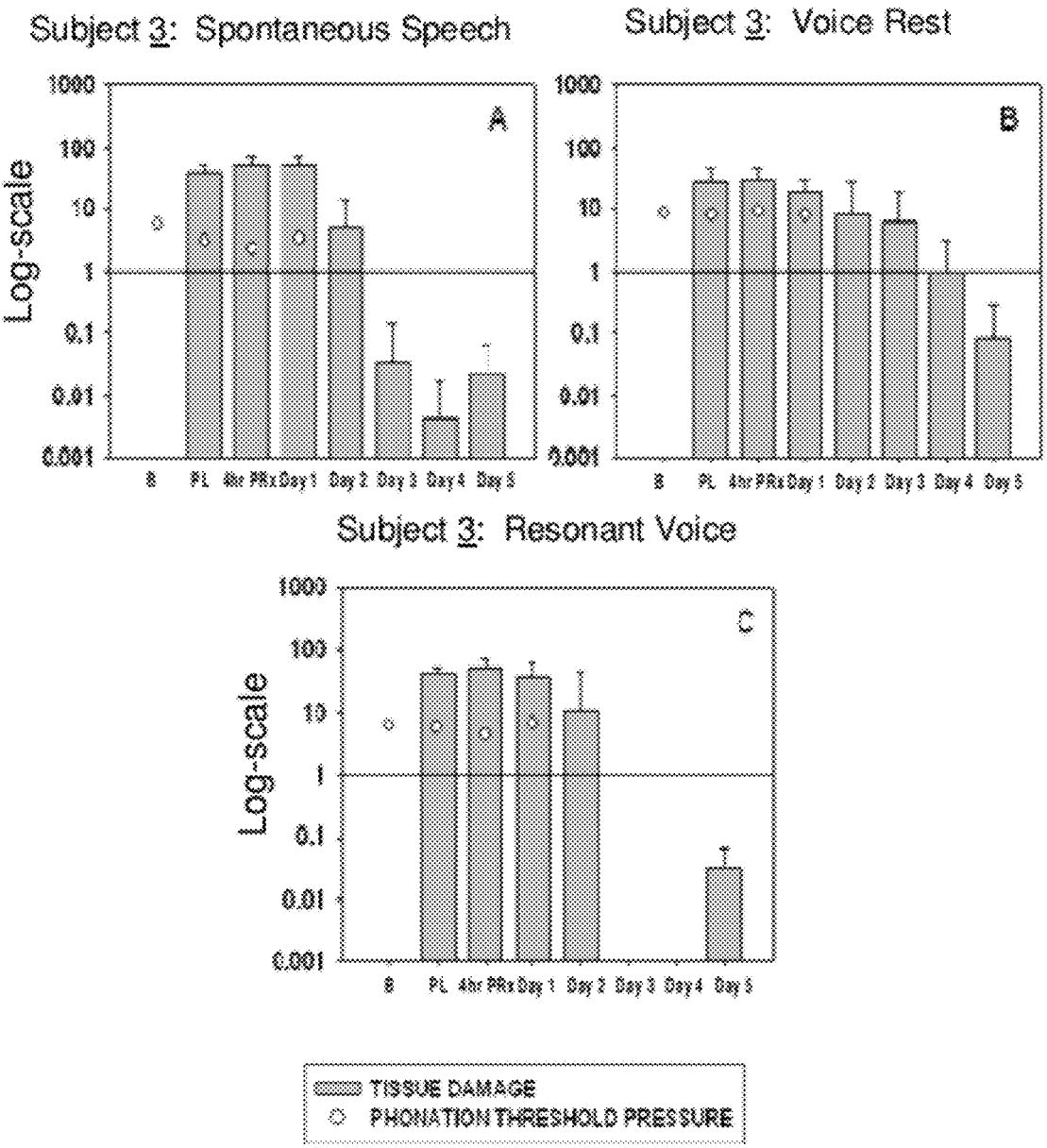

FIG. 15 shows human data of phonation threshold pressure ($cm/H_2O$ in log scale) and predictions of simulated tissue damage (arbitrary unit in log scale) following acute phonotrauma in a single human subject (Subject 3) following spontaneous speech (Panel A), voice rest (Panel B) and resonant voice (Panel C). The grey bars represent the predictions of simulated tissue damage. The empty circles represent the validation data of the four time-points (baseline, post vocal loading, following a 4-hr treatment and 24-hr post baseline) from the clinical measure of phonation threshold pressure in the human subjects. B: baseline; PL: post vocal loading; 4 hrPRx: following a 4-hr treatment.

Figure 16:
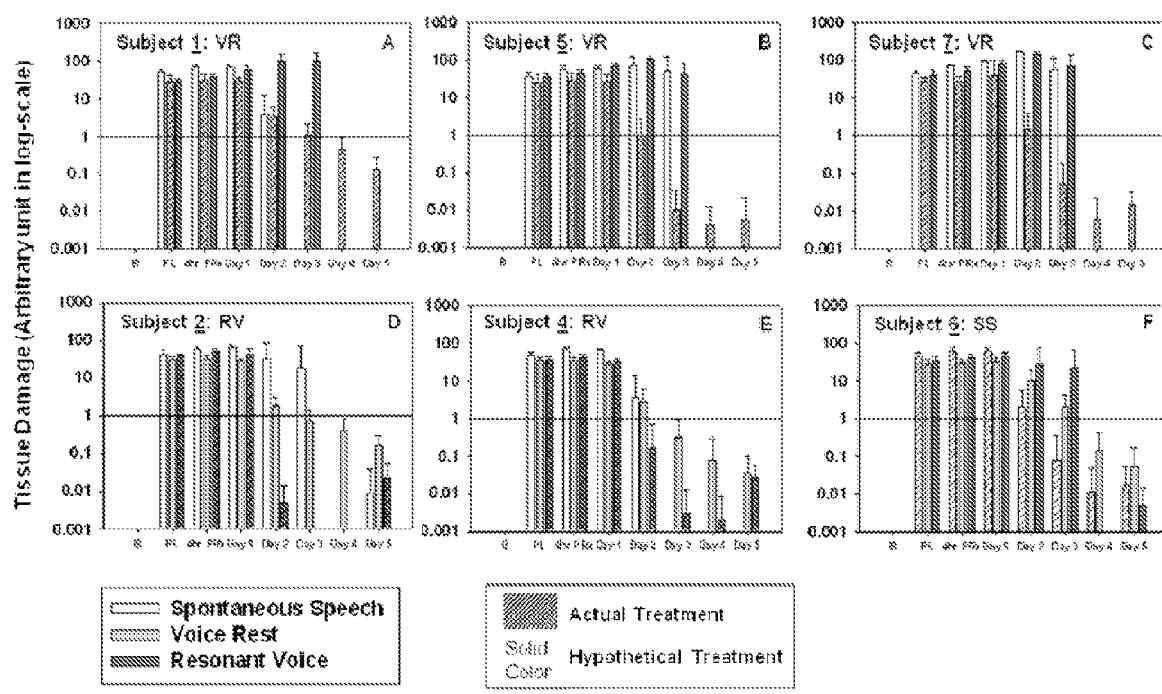
FIG. 16. Predictions of simulated tissue damage (arbitrary unit in log scale) under (1) the subject's actual treatment group and (2) the other two treatment groups (hypothetical treatment) that the subject was not exposed to in 6 human subjects (Subject 1: Panel A; Subject 5: Panel B; Subject 7: Panel C; Subject 2: Panel D; Subject 4: Panel E; Subject 6: Panel F). The bars represent the means from the simulated data of tissue damage, and the error bars represent the standard deviation from the simulated data of tissue damage. The patterned bars represent the actual treatment that the subject received in the experiment. The solid-color bars represent the hypothetical treatment of what if the subject received in the experiment. The white, light grey and dark grey bars represent spontaneous speech, voice rest and resonant voice treatment respectively. B: baseline; PL: post vocal loading; 4 hrPRx: following a 4-hr treatment.
Figures 1, 16:
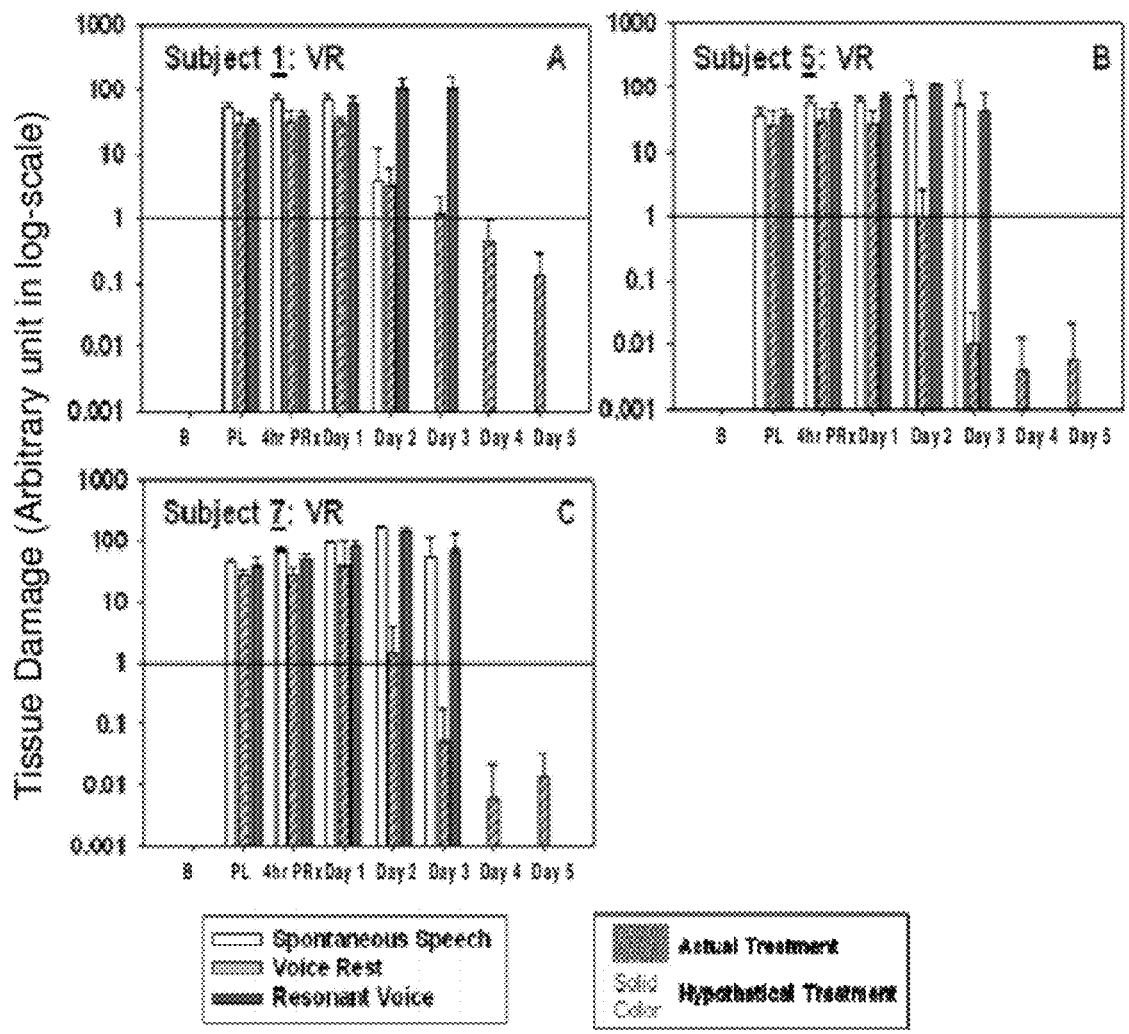
Figures 2, 16:
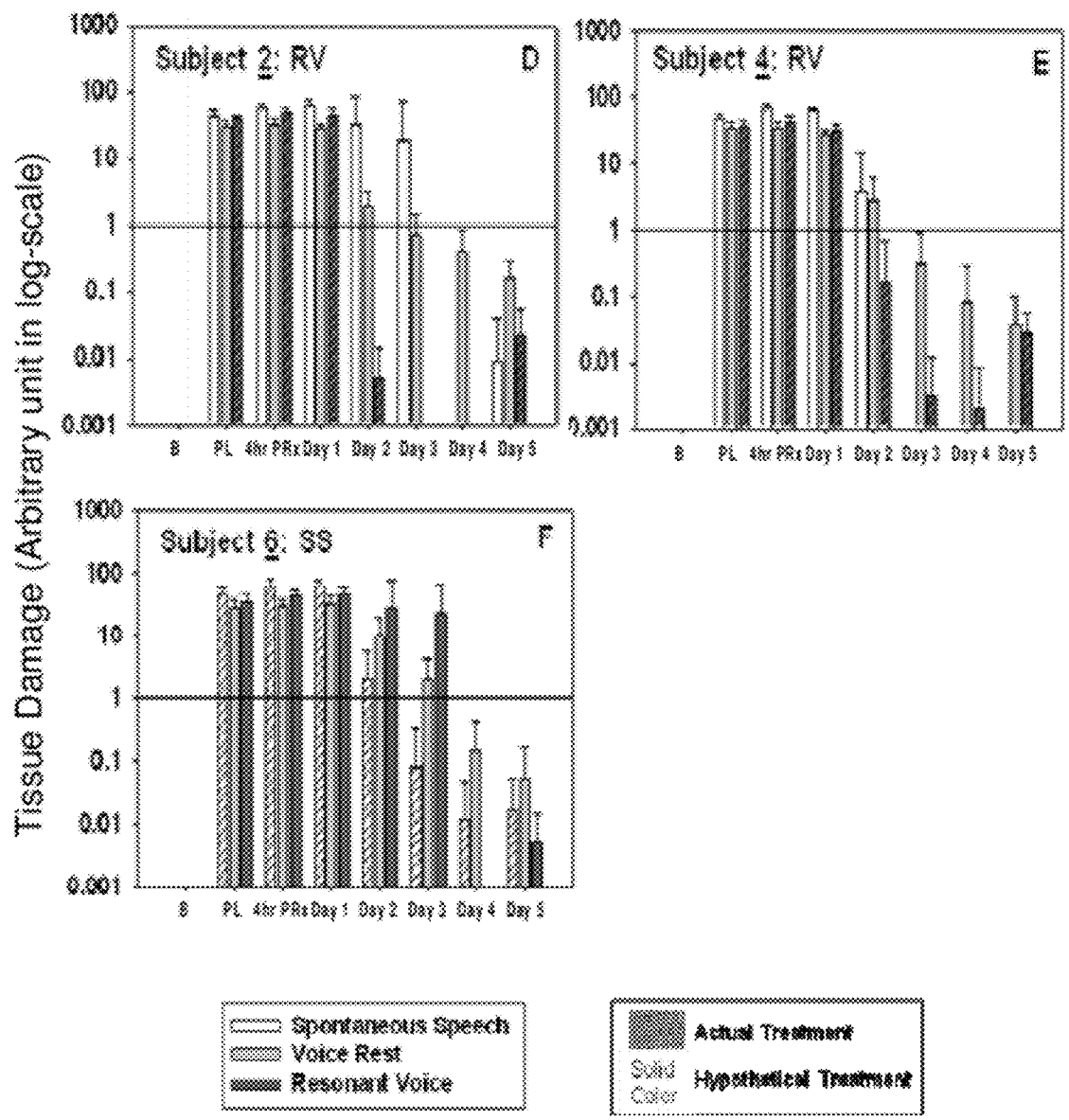

FIG. 16 shows predictions of simulated tissue damage (arbitrary unit in log scale) under (1) the subject's actual treatment group and (2) the other two treatment groups (hypothetical treatment) that the subject was not exposed to in 6 human subjects (Subject 1: Panel A; Subject 5: Panel B; Subject 7: Panel C; Subject 2: Panel D; Subject 4: Panel E; Subject 6: Panel F). The bars represent the means from the simulated data of tissue damage, and the error bars represent the standard deviation from the simulated data of tissue damage. The patterned bars represent the actual treatment that the subject received in the experiment. The solid-color bars represent the hypothetical treatment of what if the subject received in the experiment. The white, light grey and dark grey bars represent spontaneous speech, voice rest and resonant voice treatment respectively. B: baseline; PL: post vocal loading; 4 hrPRx: following a 4-hr treatment.

Predicted Trajectories of Inflammatory Mediators

Both empirical and simulation data show that the concentrations of pro-inflammatory mediators (IL-1β and TNF-α) spiked immediately following the 1-hr vocal loading, whereas the anti-inflammatory mediator (IL-10) showed a later time-point expression. Following the 4-hr treatment, the inflammatory mediators were predicted to have differentiated temporal and magnitude expression patterns across treatment groups. For the spontaneous speech condition, the ABM predicted that the inflammatory response would be further escalated, i.e., massive secretion of both pro- and anti-inflammatory mediators following the 4-hr treatment. The concentrations of pro-inflammatory mediators (IL-1β and TNF-α) reached their peaks at Day 1 post-injury and resolved to baseline concentrations around Day 2-3 post-injury. The anti-inflammatory mediator, IL-10, was also predicted to be secreted in great quantities by wound macrophages during the first 5 days post-injury. On the other hand, under the conditions of voice rest and tissue mobilization exercise, the concentrations of the pro-inflammatory mediators dropped rapidly after the 4-hour treatment and then remained low at the end of simulation, i.e., Day 5. In contrast, the anti-inflammatory mediator IL-10 was predicted to be secreted rapidly after the 4-hr treatment and remain elevated up to Day 3 post-injury.

In general, the ABM was able to reproduce and predict subject-specific cytokine trajectories as seen in the human data. For Subjects 1-3, 80% (12/15; $p<0.05$) of the times, the ABM predicted empirically-obtained cytokine values—not used for model calibration—at 24 hr. For the other 6 subjects (none of their cytokine data were used for model calibration), the ABM predicted empirically obtained cytokine values at 24 hr (1) 75% (3/4; p<0.05) of the times for those "valid" data and (2) 50% (7/14; p<0.05) of the time for those "pre-inflamed/non-responsive/invalid" data.

Using a generalized linear mixed model to account for repeated measures, the predicted levels of IL-1β, TNF-α, IL-10 and tissue damage ensuing from spontaneous speech following phonotrauma were significantly different from both voice rest and tissue mobilization exercise (p<0.05 for both comparisons). The predicted levels of cytokines and tissue damage ensuing from voice rest and tissue mobilization exercise were not statistically different.

Predicted Outcomes of Tissue Damage

Our previous work on computational simulations in sepsis, trauma and deranged healing suggested that the main index to be considered is the overall status of the tissue or the global health of the organism, rather than specific inflammatory markers. The predicted outcome of tissue damage is therefore the main index that we considered when comparing treatment scenarios. Tissue damage in this model was unitless and could be described as a proxy for "alarm/danger" signals, which are constitutive cellular components that promote inflammation during settings of stress or disruption of homeostasis. These signals would then be expected to stimulate inflammation and to drive the subsequent wound healing cascade. Under the spontaneous speech condition, indices of tissue damage were predicted to be elevated to a great extent if the subject was not prescribed voice rest or tissue mobilization exercise following acute phonotrauma. Generally, damage was predicted to persist at a high level up to Day 3 post-injury. On the other hand, if the subjects were prescribed voice rest or tissue mobilization exercise, damage was predicted to diminish by approximately Day 2 post-injury.

Discussion

Four studies have been published on the development of a novel method for obtaining quantitative information about the inflammatory status of the larynx from laryngeal secretions. The first study sampled secretions from the vocal fold surfaces of an adult female before and after one hour of vocal loading. Samples were subjected to ELISAs for IL-1β, TGF-β1, TNF-α, prostaglandin E2 (PGE-2), and matrix metalloprotease 8 (MMP-8). The results showed that pre- to post-loading shifts in mediator concentrations were clearly evident at 10 and 20 min post-loading for IL-β, TNF-α, and MMP-8, reflecting the presence of acute phonotrauma. In contrast, concentration shifts were not shown for TGF-β1 or PGE-2 (Verdolini K, Rosen C A, Branski R C, Hebda P A (2003) Shifts in biochemical markers associated with wound healing in laryngeal secretions following phonotrauma: A preliminary study. Annals of Otology, Rhinology, & Laryngology 112: 1021-1025). Another intraoperative human study used the same methodology to look at the inflammatory profile for chronic phonotrauma versus acute inflammatory disease (papilloma and epithelial cancer), and confirmed that IL-1β was an indicator of acute inflammation, whereas PGE-2 characterized chronic wounds (Branski R C, Verdolini K, Rosen C A, Hebda P A (2004) Markers of wound healing in vocal fold secretions from patients with laryngeal pathology. Annals of Otology, Rhinology, and Laryngology 113: 23-29). A third study used a rabbit surgical trauma model to assess fluctuations in inflammatory profiles from laryngeal secretions over a 3-week pre-post surgical time period. Again, IL-1β was shown to be an early indicator of inflammation, and PGE-2 was a later indicator of wound healing (Branski R C, Rosen C A, Verdolini K, Hebda P A (2005) Biochemical markers associated with acute vocal fold wound healing: a rabbit model. J Voice 19: 283-289). That is, both mediators were increased 24 hour after injury. However, the initial IL-1β spike was greater, and values resolved to baseline by Day 7 post-injury. In contrast, PGE-2 concentrations increased gradually from Day 1 to Day 7, and stayed high until the final data collection point at 3-week post-injury follow-up. Finally, a fourth publication assessed the degree to which assays of laryngeal secretions may reflect wound healing processes deep to the epithelium (Branski R C, Rosen C A, Verdolini K, Hebda P A (2005) Acute vocal fold wound healing in a rabbit model. Ann 0 to 1 Rhinol Laryngol 114: 19-24). That study, which used the same surgical rabbit model, showed that the time point associated with spikes in IL-1β (24 hour) corresponded to the presence of fibrinous clot. The time point associated with maximum PGE-2 levels (7 days) was associated with the presence of mature collagen. Massive cellular infiltration and complete epithelial coverage were found at intermediate time points.

Taken together, these studies provide robust evidence that secretions from the laryngeal surfaces can provide a quantitative window into the current inflammatory and wound healing state of vocal fold tissue. The attractiveness of the marginally invasive technology is that it can be readily used in human subjects—although not without some difficulties on the part of both subjects and examiners—and thus the data gain external validity over data obtained from more invasive technologies involving animal subjects.

This Example describes the development of an ABM that reproduces diverse trajectories of inflammatory mediators in human subjects at early time points post-phonotrauma, and furthermore was capable of predicting the levels of these mediators at 24 hrs. The subject-specific ABMs were further used to explore the effects of treatment regiments to which the individuals were not subjects and the predicted vocal fold damage under each condition was compared. The model predicted that the wound healing outcomes as informed by the cytokine trajectories and tissue damage would be dramatically different given variations in the initial cytokine profile and the treatment prescribed following phonotrauma.

Under ideal conditions, the inflammatory response would be limited by the antagonistic interactions among the various pro- and anti-inflammatory agents, followed by a transition to the later healing process in an orderly fashion. However, if repeated or chronic injuries occur over a period of time, the normal healing process would be disrupted. For instance, the ABM predicted that the secretion of pro-inflammatory mediators would be both prolonged and elevated subsequent to continuous speech following an episode of phonotraumatic injury. This prolongation would be due to a positive feedback loop involving "Pro-inflammation→Damage→Pro-inflammation," thereby delaying the transition to the subsequent healing process. Clinically, visible vocal fold inflammation would be expected. On the other hand, under conditions of either voice rest or tissue mobilization, the ABM predicted that the pro-inflammatory response would be attenuated and the anti-inflammatory response would be escalated. This prediction suggests that the repair process would bypass the Pro-inflammation→Damage→Pro-inflammation positive feedback loop and would lead to rapid healing. As a result, a reparative repair (as opposed to constructive repair) of mucosal structure and function would be observed clinically.

The model is under continuous revision and augmentation, with the ultimate, long-term goal of generating in silico models that can be queried to identify biomechanical treatments that will optimize the wound healing process in the vocal folds, as a function of patient-specific inflammatory profiles. Although these results are encouraging in terms of the potential translational utility of ABM in the setting of vocal fold inflammation, at least five limitations can be noted in our study.

First, the current ABM mainly simulated (1) inflammation, (2) proliferation and (3) collagen formation. The model did not account for a final phase of the wound healing process, which involves extracellular matrix (ECM) reorganization. According to the literature on dermal wound healing, ECM reorganization is initiated once neo-matrix such as collagen is deposited at the wound site [61,62,64]. Collagen is indeed a core component of the ECM, and undergoes remodeling that is dependent on both continued collagen synthesis and compensatory collagen degradation. The degradation of wound collagen is controlled by a variety collagenase enzymes, and the net increase in wound collagen is determined by the balance of these opposing mechanisms. Compared to the large body of literature on dermal wound healing, research on ECM reorganization in vocal fold wound healing is sparse. No in vivo measurement of collagen remodeling in human vocal folds is currently available. Thus, in its use of empirical data obtained from non-destructive methodologies only, the current model did not incorporate aspects of collagen remodeling that might prove to be important. The ABM predicted that net collagen increase reaches its maximum on Day 9 post-injury and then starts to decrease. That prediction must at some point be validated experimentally.

A second limitation in the current study is that healing outcomes in this ABM were primarily informed by interactions among inflammatory mediators and cells. However, a growing literature supports the idea that several ECM components such as fibronectin, hyaluronic acid, and decorin could also be involved in regulating the wound healing process. Studies to date have shown that aberrant scarring/fibrosis is at least partly due to the response of fibroblasts in the wound to both inflammatory mediators and extracellular matrix components, some of which are known to constitute alarm/danger signals (e.g. hyaluronic acid) and therefore may be currently abstracted under the "damage" variable in our model. Future iterations of the ABM could be augmented with rules around the interactions among inflammatory mediators, cells and ECM components to yield more precise predictions.

Third, this model assumes that biomechanical stresses during phonation cause mucosal damage. However, the current biologically-based ABM lacks the ability to receive input from physical models of phonation, because data are lacking regarding the link between the output of physical models—i.e. distributed tissue stresses (and the biological consequences of those stresses. Although biochemical networks may be reasonably modeled by using stochastic simulations, many cellular biological phenomena relating to wound healing require the calculation of biophysical processes, such as tissue deformation and disruption of intracellular adhesion. Ideally, the synthesized biochemical networks should be coupled with these biophysical processes to yield a more complete picture of vocal fold wound healing in response to biomechanical stresses during phonation.

A fourth limitation relates to the inclusion of the multi-functional anti-inflammatory mediator TGF-$\beta$1 in the model, although earlier work on assaying biochemical markers of vocal fold wound healing failed to detect this mediator in laryngeal secretions pre- or post-traumatically (Branski R C et al. (2004) Annals of Otology, Rhinology, and Laryngology 113: 23-29). TGF-$\beta$1 is known to be involved in the regulation of cell proliferation, cell differentiation and extracellular matrix formation in all phases of inflammation and wound healing. This mediator exerts both anti-inflammatory and pro-fibrotic effects that could convert an active site of inflammation into a site dominated by subsequent tissue repair. It is suspected that TGF-$\beta$1 might be highly cell-associated, and that this property might have led to our inability to detect this cytokine in vocal fold secretions (Branski R C et al. (2004) Annals of Otology, Rhinology, and Laryngology 113: 23-29). To determine if TGF-$\beta$1 is necessary for a correct simulation of inflammation and wound healing in the vocal folds, a qualitative validation procedure was carried out to determine what the simulated data would show in the presence or absence of TGF-$\beta$1. In the latter case, the ABM predicted that no cellular and molecular events would be triggered for any ranges of initial damage (data not shown). In the presence of TGF-$\beta$1, the ABM predicted different inflammatory and wound healing curves that vary with initial magnitude of mucosal damage (FIGS. 12 and 13). These results indicated that TGF-$\beta$1 (or a qualitatively similar cytokine) is essential for the wound healing process and should be included in the ABM structure.

The fifth, and perhaps most important, limitation concerns the validation of the ABM predictions with regard to the different treatment modalities. In this study data for nine humans is shown along with the capacity of the ABM to predict mid-term (24-hr) inflammation based on short-term assays. We have not, however, verified in a large cohort of patients that validity of ABM predictions with regard to treatment outcome. It should be noted that such studies in humans are complex from regulatory, practical, and ethical points of view. We have embarked on a large-scale study to validate the ABM described herein. Indeed, clinical management of phonotrauma remains a challenge to clinicians. Large clinical trials are needed to establish optimized patient-specific treatment interventions. We suggest that a systems biology approach that involves modeling is integral to sorting through the perplexing array of factors that dictate success or failure of clinical trials for complex diseases. Ultimately, this process would be augmented by the inclusion of genetic variability in inflammatory and wound healing components, typically mediated via single-nucleotide gene polymorphisms in relevant genes.

In summary, this study suggests for the first time that patient-specific, individualized models of inflammation and healing are possible. This demonstration extends the power of translational simulations of acute inflammation beyond the responses of idealized organisms, quantitative prediction of inflammation occurring in experimental animals, and simulations of populations (clinical trials). This work will hopefully point the way to addressing other complex disease processes.

EXAMPLE 3

Necrotizing Enterocolitis (NEC)

The pathogenesis of NEC is a problem ideally suited to mathematical modeling approaches at various levels, because of the unique combination of development, inflammation, and healing in a remote organ system with systemic manifestations.

Approaching intricate biological systems with a reductionist mentality falls short in that simple individual elements do not always act linearly, can proceed through sometimes-redundant pathways, and can be functionally diverse under variable circumstances (Csete, M E Doyle, J C: Reverse engineering of biological complexity. Science, 2002; 295(5560):

p. 1664-9 and Kitano, H: Systems biology: a brief overview. Science, 2002; 295(5560): p. 1662-4). This issue is best highlighted through our attempts to understand and modulate the multi-organ failure that may result from acute inflammatory responses to infection, traumatic injury, hemorrhagic/septic shock, and NEC. Although much has been learned about cellular mechanisms and molecular mediators that initiate and drive the inflammation and tissue repair in these disease states, treatment with multiple anti-inflammatory agents (anti-TNF, Il-1b, PAF, bradykinin, etc.) showed no survival benefit in clinical trials (Freeman, B D Natanson, C: Anti-inflammatory therapies in sepsis and septic shock. Expert Opin Investig Drugs, 2000; 9(7): p. 1651-63). The likely explanation for this is that acute inflammation is a complex process, and that pointed manipulation of single pathways or mediators within the system cannot be adequately predicted from knowledge of those pathways or mediators in isolation (Buchman, T G, Cobb, J P, Lapedes, A S, et al: Complex systems analysis: a tool for shock research. Shock, 2001; 16(4): p. 248-51; Tjardes, T Neugebauer, E: Sepsis research in the next millennium: concentrate on the software rather than the hardware. Shock, 2002; 17(1): p. 1-8 and Vodovotz, Y, Clermont, G, Chow, C, et al: Mathematical models of the acute inflammatory response. Curr Opin Crit. Care, 2004; 10(5): p. 383-90). In addition, the correct therapy may depend on the exact chronological stage and trajectory of the disease.

Robustness is an essential part of biological systems, and must be tested to ensure veracity. The properties exhibited by robust systems can be classified into three areas according to Kitano (Kitano, H: *Systems biology: a brief overview. Science,* 2002; 295(5560): p. 1662-4): (i) adaptation, which denotes the ability to cope with environmental changes; (ii) parameter insensitivity, which indicates a system's relative insensitivity to specific kinetic parameters; and (iii) graceful degeneration, which reflects the characteristic slow degradation of a system's functions after damage, rather than catastrophic failure (2). Such properties are achieved through feedback loops, modularity, redundancy, and structural stability, ensuring that robust systems remain homeostatic even when internal parameters or external environmental influences are altered.

Systems level analysis is being increasingly applied to a growing number of biological models, being made possible by a number of rapidly growing advances in quantitative molecular biology that make possible the large amount of high throughout experimental data. Below, we describe our variation on this approach.

Systems Biology Approach to Acute Inflammation and NEC

To examine what cellular and molecular mechanisms contribute to the pathogenesis of NEC, we developed a mathematical model incorporating major components of the acute inflammatory response using input elements from documented experimental data. We propose that modeling will characterize the complex interplay of the network and provide insight into the global consequences of manipulating individual components of inflammation.

Our NEC mathematical model is comprised of two compartments, tissue and blood. Cell types include macrophages, neutrophils, dendritic cells, T-helper (TH1 and TH2) cells, and pathogens (with macrophages and neutrophils in either an active or resting state). Macrophages are confined to the tissue, while neutrophils are confined to the blood until they are activated. Dendritic cells (DC) travel to lymph nodes, where they activate TH1 or TH2 cells depending on the cytokine milieu. There are several diffusible compounds, namely pro- and anti-inflammatory cytokines, free radicals (which cause tissue damage), and lipopolysaccharides (LPS) produced by the bacteria, all of which can cross through the endothelial boundary between the tissue and the blood. Further, inflammation caused by pro-inflammatory cytokines leads to tissue death. This in turn results in an increase in the diffusivity of the small molecules. The aforementioned model is easily adaptable to previously described inflammation models. Notable differences include the normal acquisition of bacteria in the lumen of the intestine (a.k.a. succession) and the normal "leakiness" of the premature intestinal barrier that becomes less permeable over time.

We initially approached this complex model by breaking the system into smaller pieces that are amenable to mathematical analysis. For example, consider the damage-induced increase in cross-endothelial diffusion of small molecules. This increase in diffusion allows more cytokines to enter the blood from the tissue pool, which activates more resting neutrophils. The active neutrophils enter the tissue, causing damage that increases the diffusion. This is a key positive feedback loop, which we think underlies the inflammatory response. To see what is needed for diffusion-dependent bistability (between healthy and inflamed states), we extract the part of the full model involving neutrophils and inflammatory cytokines; this is a time-tested approach in dynamical systems modeling, which allows for analysis of otherwise essentially impenetrable differential equation-based models. We have used this approach successfully in the past to address aspects of the biology of sepsis (Kumar, R, Clermont, G, Vodovotz, Y, et al: The dynamics of acute inflammation. J Theor Biol, 2004; 230(2): p. 145-55; Reynolds, A, Rubin, J, Clermont, G, et al: A reduced mathematical model of the acute inflammatory response: I. Derivation of model and analysis of anti-inflammation. J Theor Biol, 2006 and Day, J, Rubin, J, Vodovotz, Y, et al: A reduced mathematical model of the acute inflammatory response II. Capturing scenarios of repeated endotoxin administration. J Theor Biol, 2006). Equation 1 demonstrates this approach.

$$n'_a = f(c_b) - v \cdot n_a \qquad \text{Equation 1}$$

$$c'_b = \gamma c_b + \frac{d}{d+\eta}(r \cdot n_a - \eta c_b)$$

Figure 18:
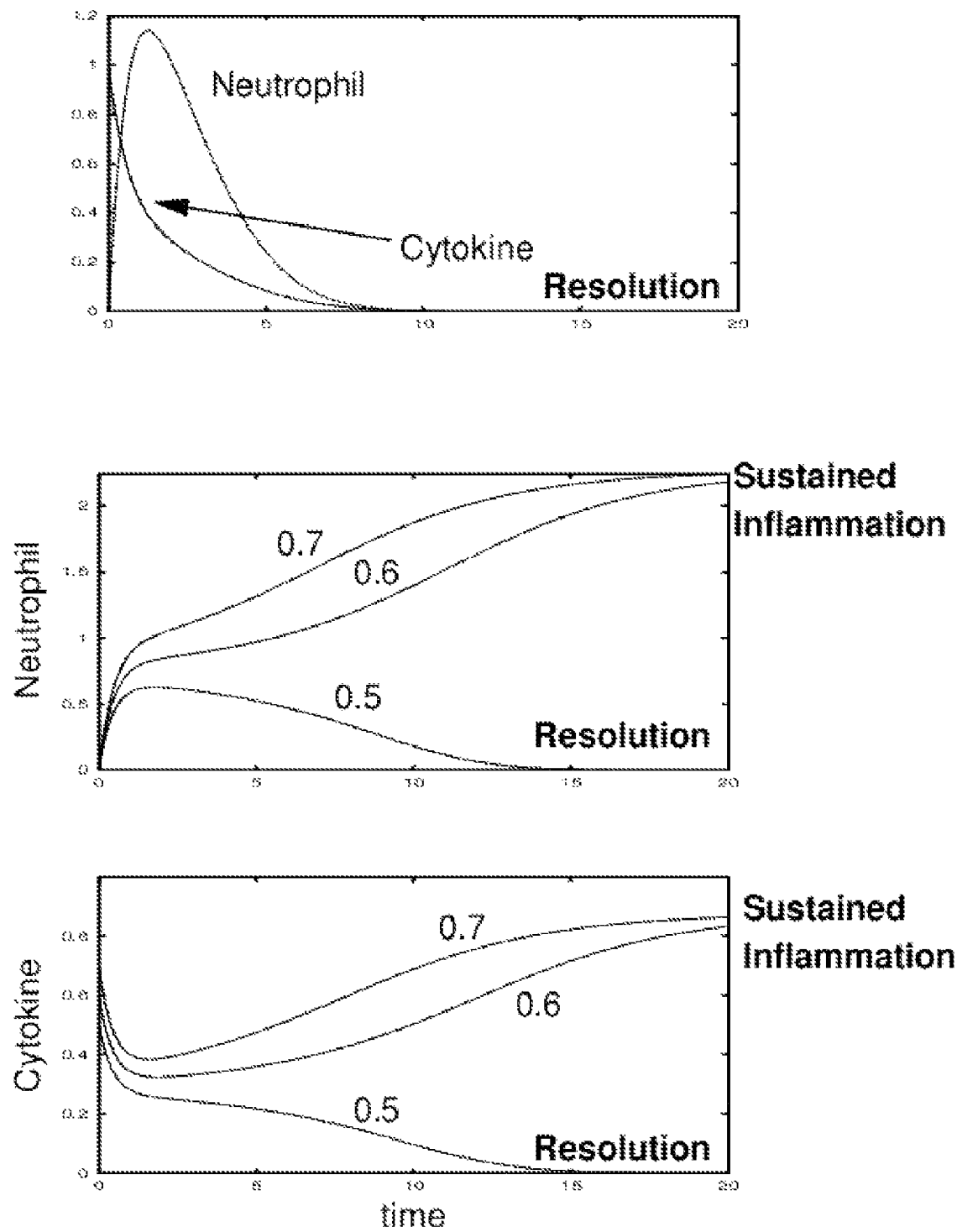
FIG. 18 shows modeling of Neutrophil/Cytokine interactions and their effect on intestinal permeability. Top panel: A representation of the interaction among neutrophils and cytokines in a setting of low damage. Low damage is associated with a low level of leakiness of the intestinal epithelial barrier following exposure to a small amount of pro-inflammatory cytokines (prototypically TNF-α). Middle and Bottom panels: At higher damage, a larger degree of epithelial barrier leakiness occurs following exposure to a small amount of pro-inflammatory cytokines, leading to increased activation of neutrophils (Panel B) and consequent production of pro-inflammatory cytokines (Panel C). These events lead to bistable behavior (sustained inflammation vs. resolution of inflammation) depending on exact conditions. The numbers (0.5, 0.6, 0.7) are the initial values of the pro-inflammatory cytokine. For low values there is resolution but for higher values, there is enough feedback to cause a sustained response. Panels A-C: all numbers are unitless.

By setting some of the variables to their steady-states, we obtain a simple two-variable model involving the active neutrophils in the tissue $n_a$ and the blood level of inflammatory cytokines $c_b$, where $f(c_b)$ is a sigmoidal function representing the combined production of activated neutrophils by inflammatory cytokines and transport of activated neutrophils to the tissue compartment. The parameters $v$, $\gamma$, $\eta$ are degradation rates of the neutrophils, blood cytokines and tissue cytokines respectively; $r$ is the rate of production of cytokine by the neutrophils in the tissue in response to initial tissue damage (e.g. from hypoxia) and bacterial translocation. The parameter $d$ is the diffusivity of the cytokines from the blood to the tissue. When $d$ is small, the only state is the resting state. As $d$ increases, the system is bistable with a new inflamed state. These interactions are shown graphically in FIG. 18.

The inflamed state is very easy to achieve once the diffusion passes a critical value. Another sub-module in the large model involves the transient production of TNF-α in the tissue by the macrophages. This product is transient because of the inhibitory effect of IL-10 on the macrophage activation. Thus, the module involves resting macrophages, activated macrophages, TNF-α and IL-10. As above, by setting both macrophage populations to steady-state levels, the model reduces to two equations for TNF (X) and IL-10 (Y) tissue concentrations (Equation 2).

$$\frac{dX}{dt} = -\mu X + k_X F(X, Y)$$
$$\frac{dY}{dt} = -\nu Y + k_Y F(X, Y)$$
$$F(X, Y) = \frac{X^2}{(1+X^2)(1+Y)}$$

Equation 2

Figure 19:
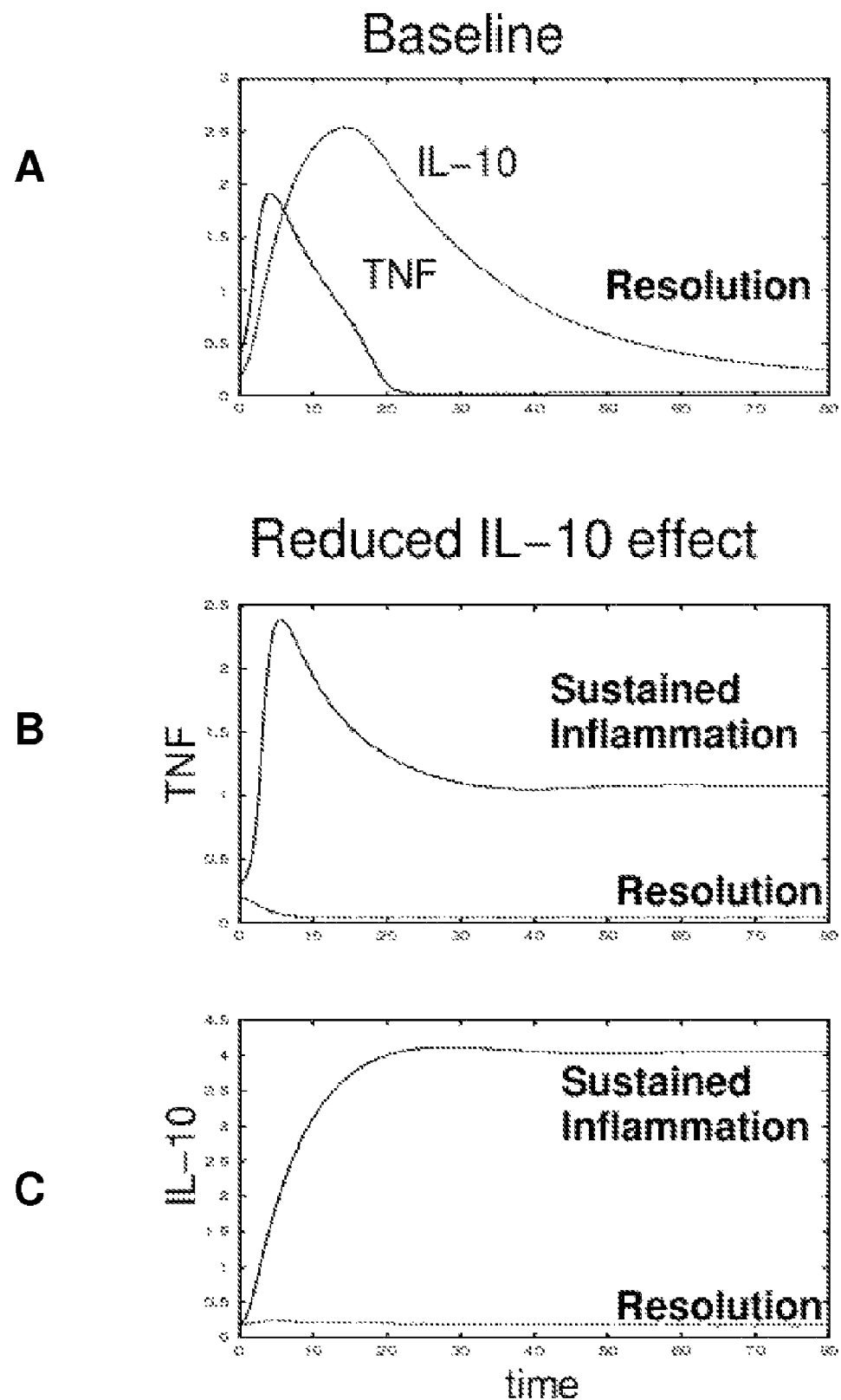
FIG. 19 shows modeling interactions between TNF-α, and IL-10 in the setting of intestinal inflammation. Panel A: At baseline, exposure to a small amount of TNF-α can lead to an amplification of the inflammatory response, but the anti-inflammatory actions of IL-10 result in a return to the baseline state. Panels B and C: The effectiveness of IL-10 on suppressing TNF-α is simulated to be degraded by half. The result is bistability between a stable rest state and an inflamed state, differing only by the initial amount of TNF. Panel B shows the effects of this scenario on TNF-α. Panel C shows the effects of this scenario on IL-10. Panels A-C: all numbers are unitless.

Here, several variables have been rescaled to eliminate some of the parameters. This is a classic activator-inhibitor system, where X is self-activating and Y inhibits. The main point is that if the IL-10 production is slower than that of TNF, then with appropriate choices of $k_X, k_Y$, this system is excitable and there is a transient increase in TNF before returning to rest. If IL-10 is blocked or reduced, then bistability between a healthy state and an inflamed state is possible, as depicted graphically in FIG. 19.

Calibration of Inflammation Models to Experimental Data

A central part of our long-term modeling approach is the calibration of existing mathematical models of inflammation (Chow, C C, Clermont, G, Kumar, R, et al: *The acute inflammatory response in diverse shock states*. Shock, 2005; 24(1): p. 74-84) to data in rodent and human NEC. In previous work, it was hypothesized that the machinery linking different components of the early inflammatory was "hard-wired" and independent of the specific stress encountered (Chow, C C, Clermont, G, Kumar, R, et al: *The acute inflammatory response in diverse shock states*. Shock, 2005; 24(1): p. 74-84). However, the response would have different expressions given that different types of stress provided different initial conditions to an otherwise unified system. Using this underlying assumption, the mathematical model was calibrated to various species of pre-clinical relevance: mice (subjected to LPS, surgical trauma, and surgery followed by hemorrhagic shock (Chow, C C, Clermont, G, Kumar, R, et al: *The acute inflammatory response in diverse shock states*. Shock, 2005; 24(1): p. 74-84); rats (subjected to endotoxemia, surgical trauma, and surgery+endotoxemia [Lagoa et al, manuscript in preparation], as well as true bacterial sepsis [Lagoa et al, manuscript in preparation]); and swine (based on literature data and including interactions of inflammatory cytokines with matrix metalloproteases (MMP's) in the setting of endotoxemia (Nieman, G, Bartels, J, Wei, J, et al: *Mathematical simulation of inflammation in porcine septic shock and ARDS*. Shock, 2005; 23 (Supplement 3:3)). We have also begun to calibrate the inflammation model in humans, using data on human endotoxemia (Day, J, Rubin, J, Vodovotz, Y, et al: *A reduced mathematical model of the acute inflammatory response II. Capturing scenarios of repeated endotoxin administration*. J Theor Biol, 2006). We have begun to collect dense inflammatory biomarker data in our neonatal rat model of NEC described above, which will be used to calibrate our mathematical model for systemic inflammation in the setting of NEC (Zamora, R, Vodovotz, Y, Ford, H, et al. *Plasma cytokine levels in experimental necrotizing enterocolitis: a mathematical model is needed. in 4th International Conference on Complexity in Acute Illness*. 2005. Cologne, Germany).

Spatial Modeling of NEC

In addition to its dynamic behavior, the inflammation process in NEC exhibits a number of spatial characteristics, such as diffusion of inflammatory agents, chemotaxis, and epithelial cell migration. We have developed a model for NEC, which includes four compartments—lumen, epithelial layer, organ tissue, and blood. The model allows for spatial distribution and movement of the system components. This is achieved by including spatial derivatives in the differential equations. Each compartment is assigned specific diffusion parameters, which affect the movement of inflammatory agents.

The ability of lumen bacteria to infiltrate the organ tissue critically depends on the integrity of the epithelial wall, which is affected by factors such as cell migration and strength of tight junctions. The ability of a damaged wall to heal depends on the level of infection via the amount of LPS present in the system. Tight junction proteins can be destroyed by the presence of NO, which is produced by the inflammatory reactions.

Figure 20:
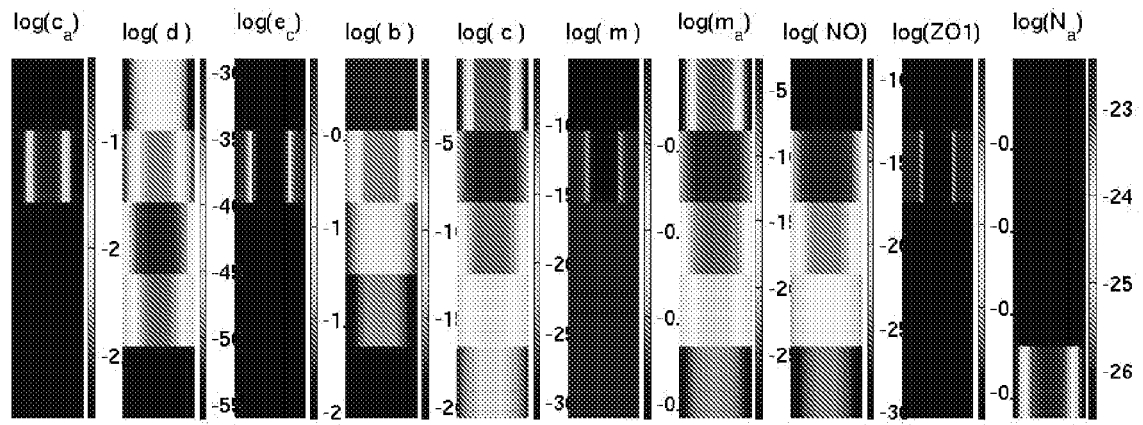
FIGS. 20, 21 and 22 show a spatial model of NEC.
Figure 21:
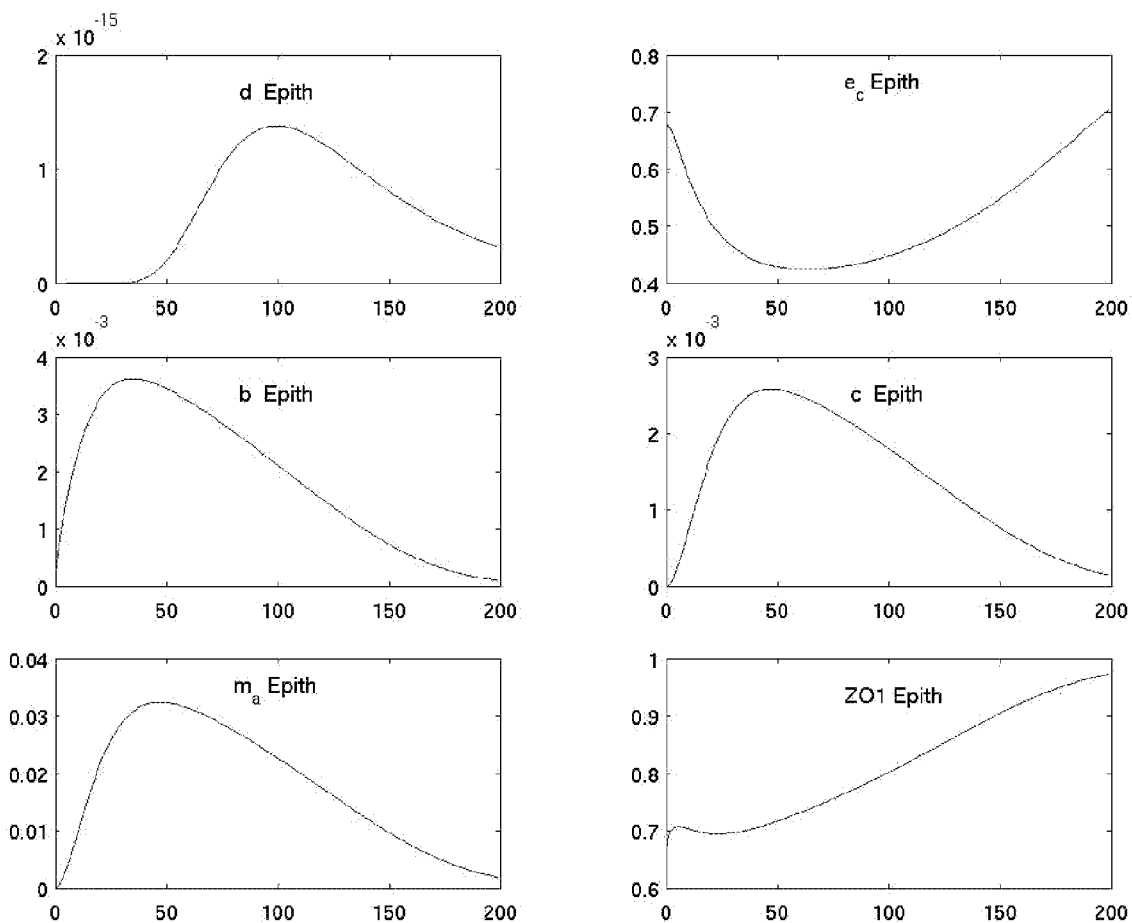
Figure 22:
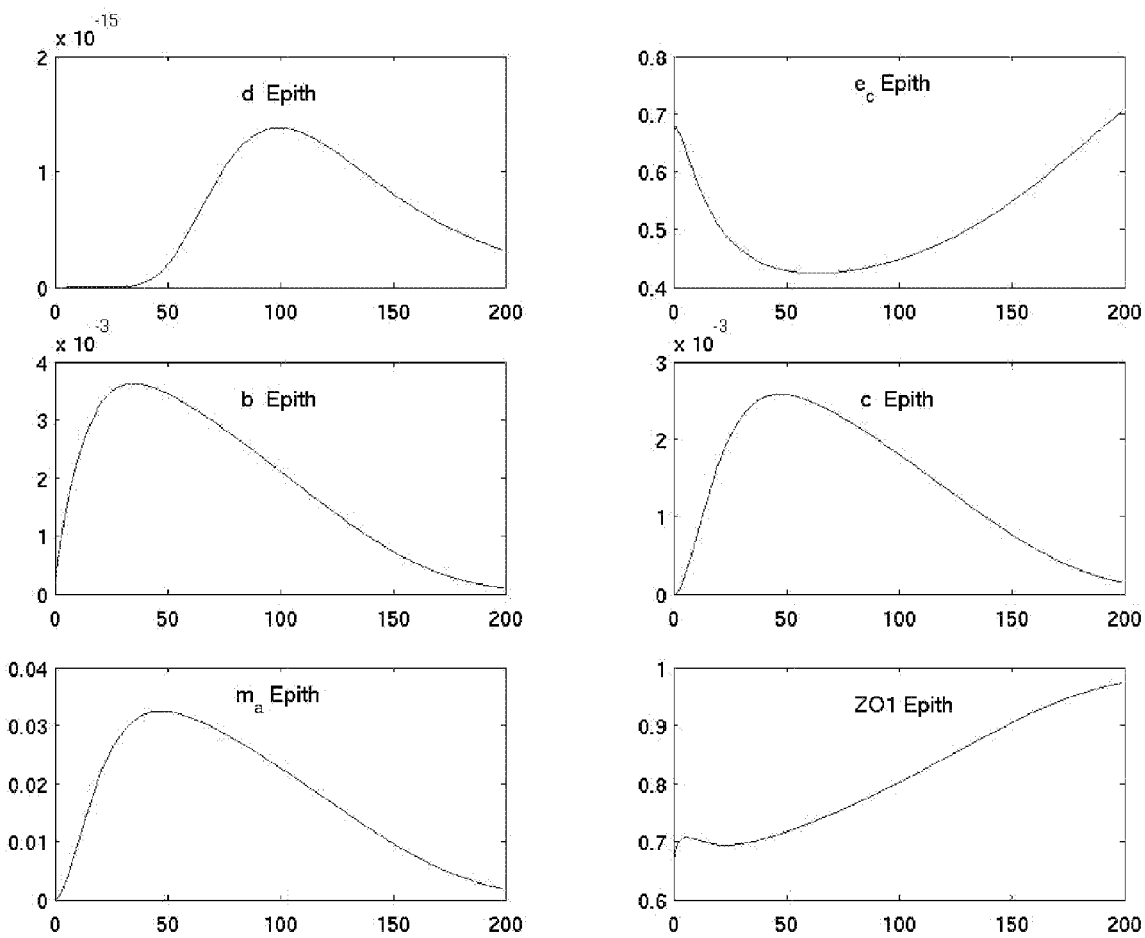

We present simulation results that show that even normally harmless bacteria in the lumen can penetrate damaged epithelial wall and cause serious infection. The level of damage may affect the outcome, leading to either healthy state or persistent inflammation. In FIGS. 20-22, we show results from two simulations, first with a partially damaged epithelial wall, and second with a completely missing portion of the wall. In the first case, although some bacteria enter the tissue and start an inflammatory process, it is eventually killed and the wall is healed. In the second case, a larger amount of bacteria penetrates into the tissue, leading to a more severe inflammatory response, which in turn affects the ability of the wall to heal. FIG. 20 shows the state of the system in the first case, at the peak of the inflammatory process.

In sum, necrotizing enterocolitis is a multifactorial disease largely affecting premature infants. Many inflammatory mediators are implicated in NEC pathogenesis but no set of biomarkers delineates infants that will go on to develop NEC. Animal models shed some light on mediators that may contribute to NEC but fall short in predicting biomarkers that may determine susceptibility. Mathematical modeling is an alternative strategy employed in understanding complex inflammatory diseases and it holds promise in helping investigators to understanding the pathogenesis of NEC.

EXAMPLE 4

Restenosis

An agent-based model of the response to arterial injury was created. This simulation currently mimics the response of porcine arteries to balloon overstretch, a well-accepted pre-clinical model used for testing of devices and therapeutics for restenosis (Karas, S. P. et al. Coronary intimal proliferation after balloon injury and stenting in swine: an animal model of restenosis. *J. Am. Coll. Cardiol.* 20, 467-474 (1992) and Robinson, K. A. Pig coronary artery model of post-angioplasty restenosis in *Vascular Brachytherapy* (eds. Waksman, R., King, S. B., Crocker, I. R. & Mould, R. F.) 30-40 1996). In this model, an initially intact vessel (FIG. 23A, note intact endothelium [dark gray], media [light gray, containing quiescent smooth muscle cells (SMC)], and adventitia [medium gray, containing quiescent fibroblasts and resting macrophages]). The ABM also includes platelets, which aggregate at the site of endothelial damage; the cytokine transforming growth factor-β1 (TGF-β1), released from platelets upon activation and a stimulant of smooth muscle cells. When the vessel is injured (FIG. 23B), the dark gray endothelium becomes black, indicating the area of rupture of endothelium following balloon angioplasty. Each subsequent figure (FIGS. 23A-O) represent the evolution of the response to this balloon overstretch injury, with 100 time steps in the ABM representing approximately one day. The ABM reproduces realistic time courses of restenosis, with the following features:

By day 3 (FIG. 23E), one observes the formation of thrombus (dark grey infiltrate in the vessel lumen) and the beginnings of smooth muscle cell proliferation and neointima formation.

By day 7 (FIG. 23I), restenosis is evident (the lumen is getting smaller) with continuing evidence of thrombus.

By day 14 (FIG. 23N), restenosis is evident, smooth muscle cells are proliferating there is continuing evidence of thrombus, and the endothelium is regenerating (dark gray).

By day 15 (FIG. 23O), restenosis is evident, there is continuing evidence of thrombus, and the endothelium is regenerating (dark gray).

Importantly these responses are driven by tissue damage (the denuded endothelium), which stimulates inflammation through the chemoattraction of macrophages and smooth muscle cells. The following are the rules for Restenosis Model created in Netlogo.

Figure 23A:
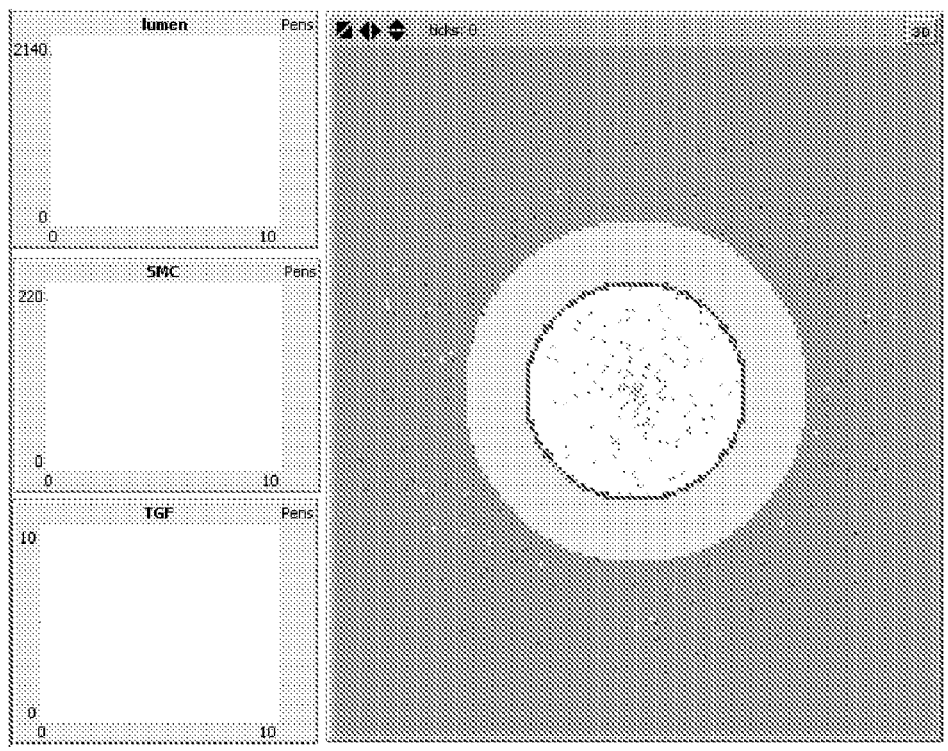
FIGS. 23A-23O show the evolution of the response to balloon overstretch injury in one embodiment of an ABM restenosis model.
Figure 23B:
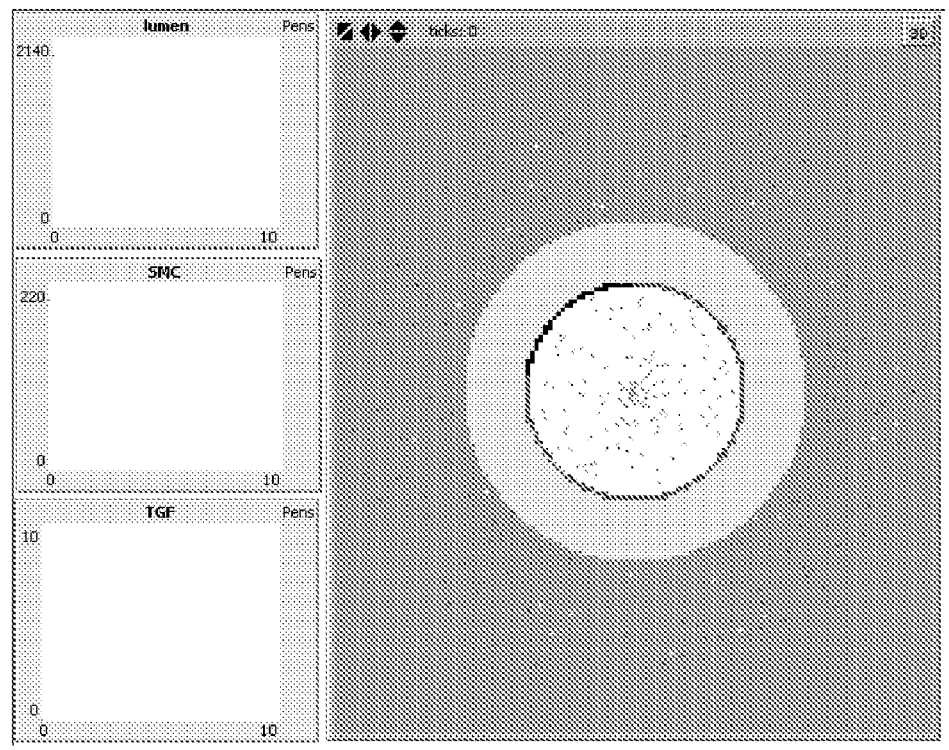
Figure 23C:
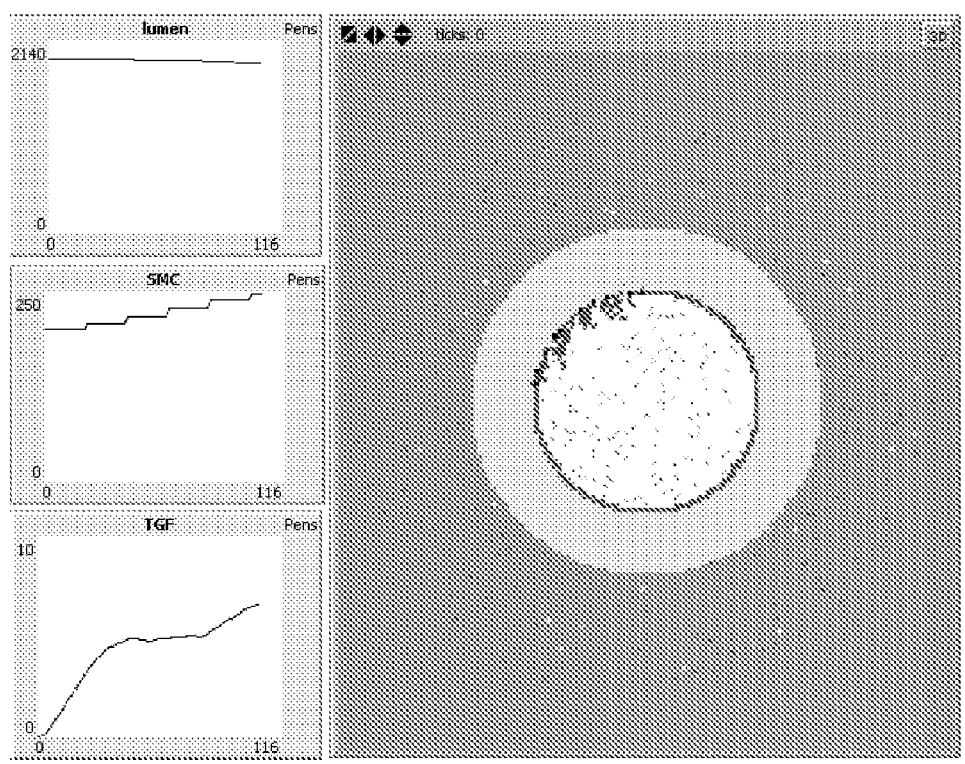
Figure 23D:
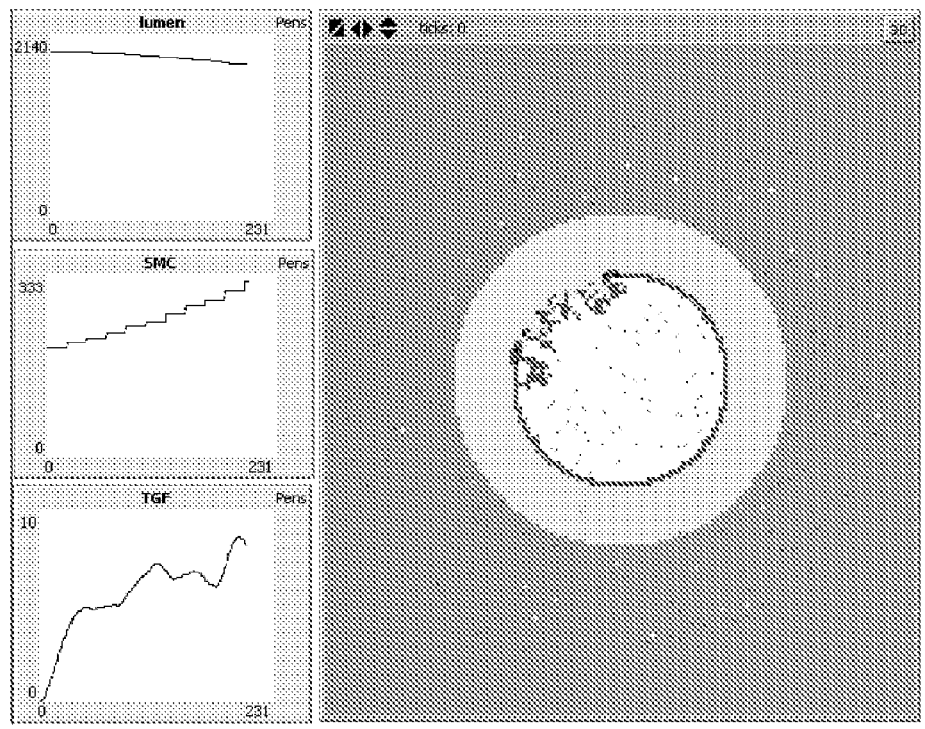
Figure 23E:
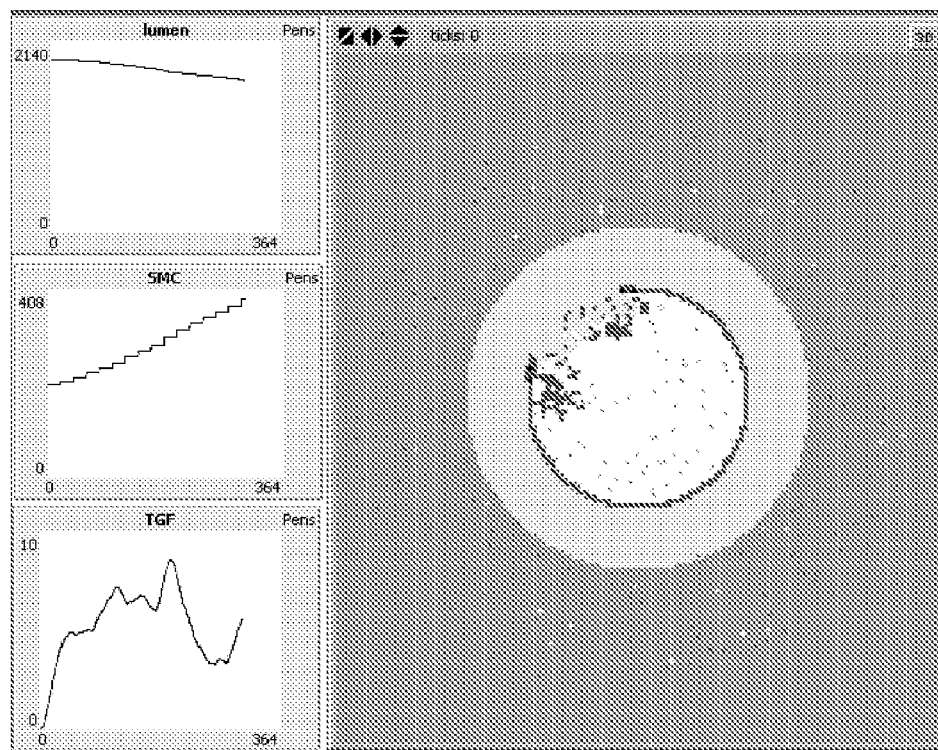
Figure 23F:
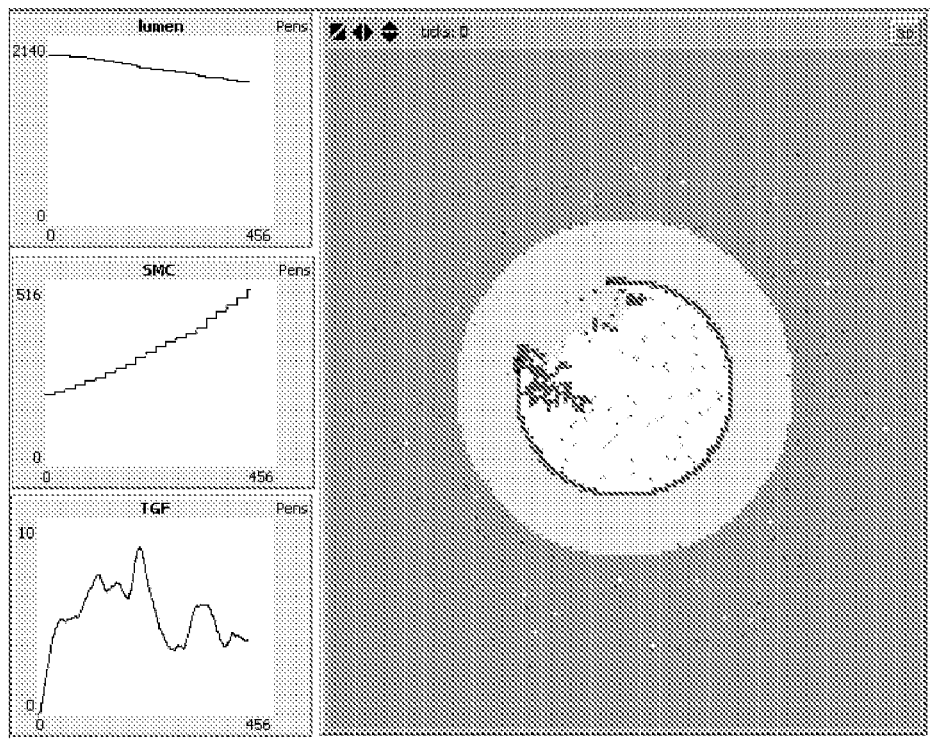
Figure 23G:
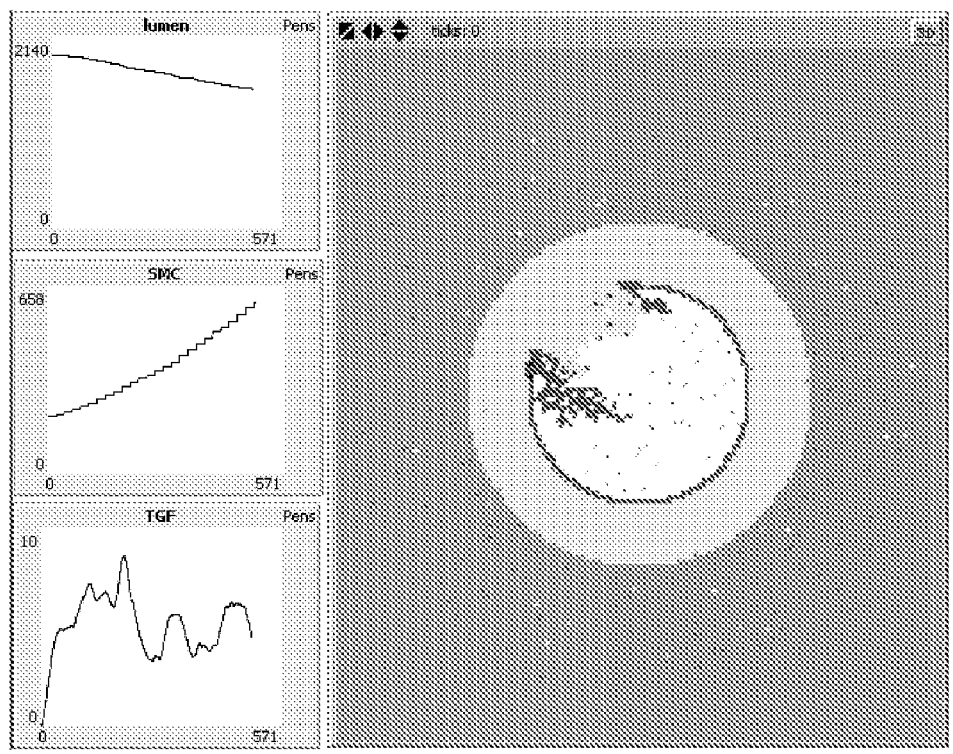
Figure 23H:
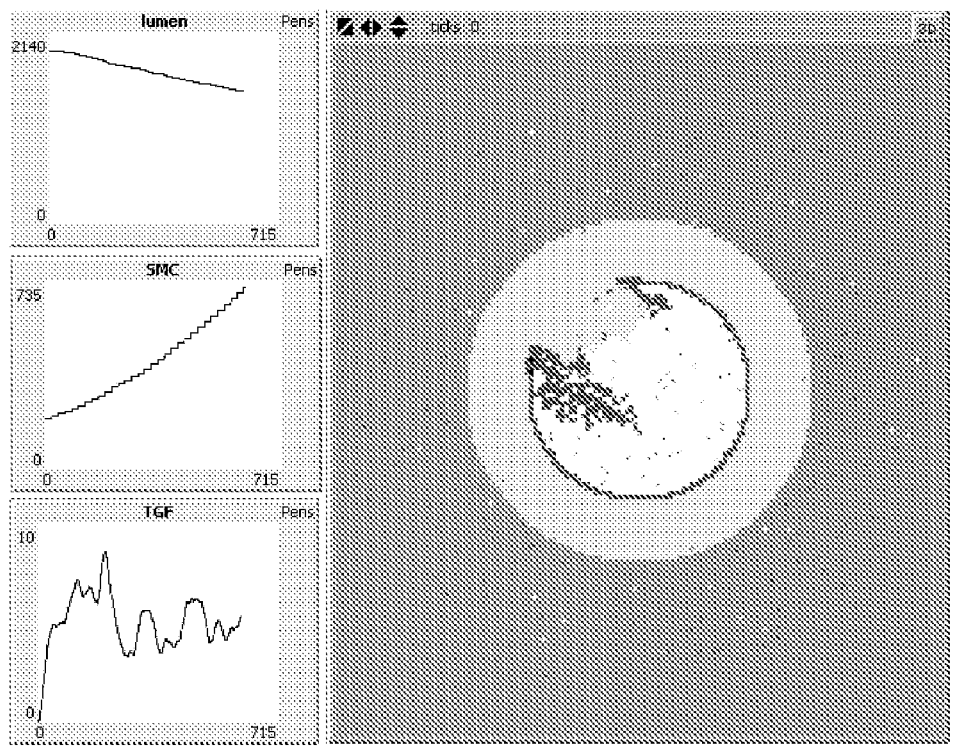
Figure 23I:
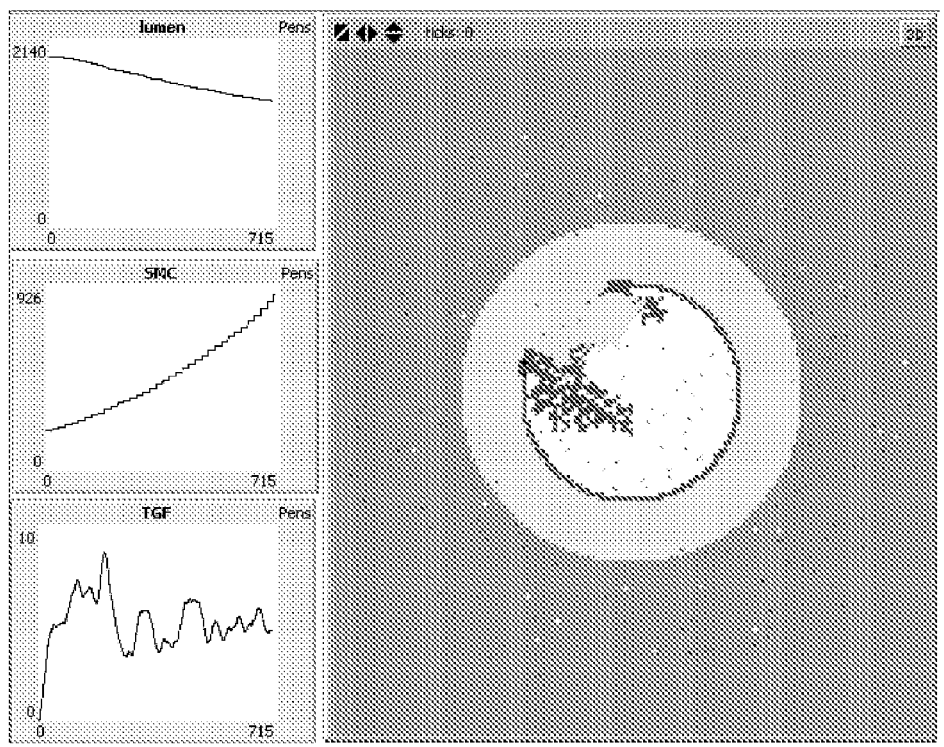
Figure 23J:
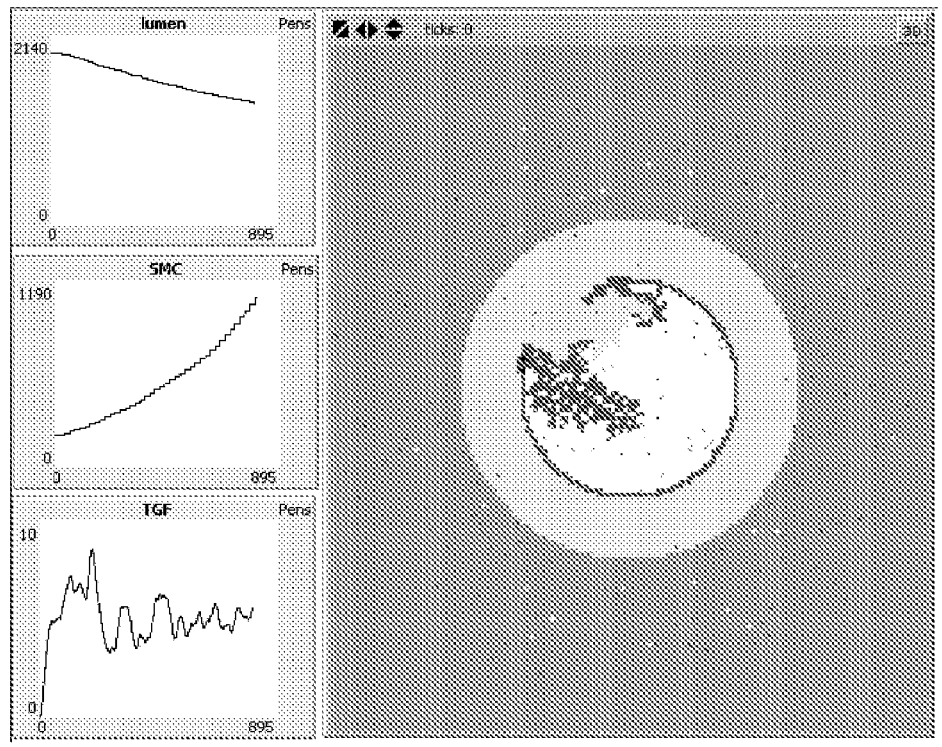
Figure 23K:
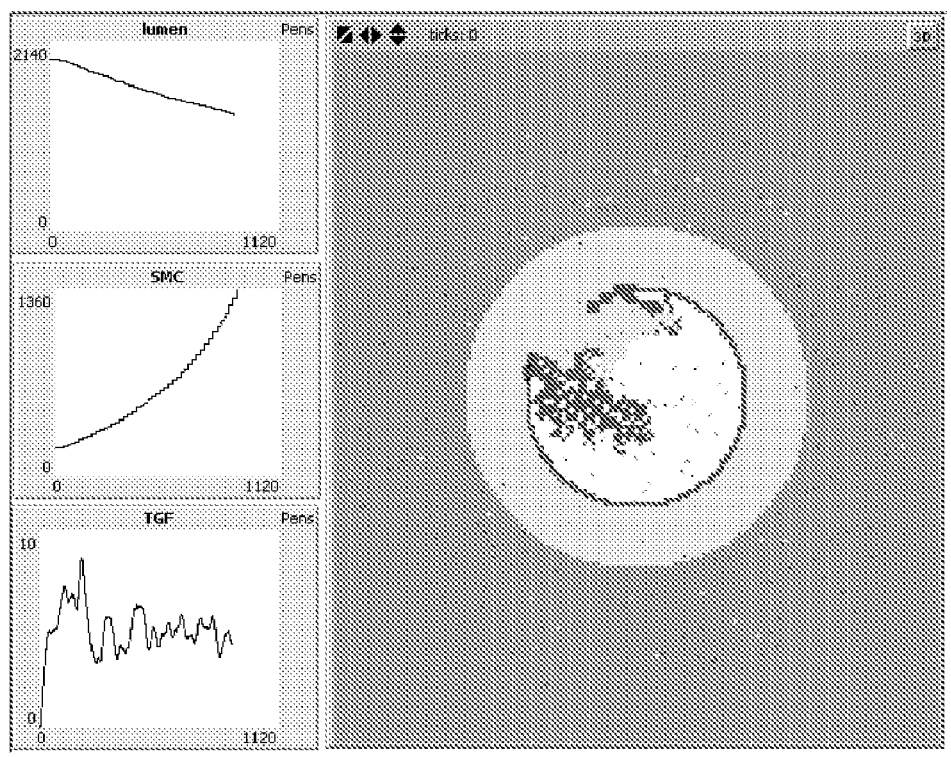
Figure 23L:
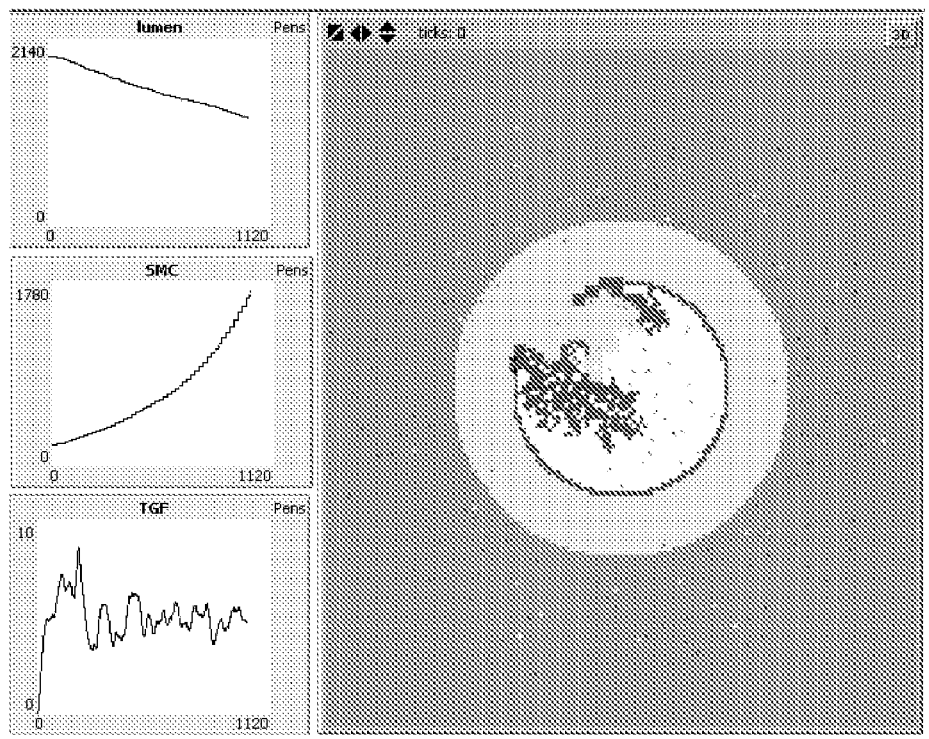
Figure 23M:
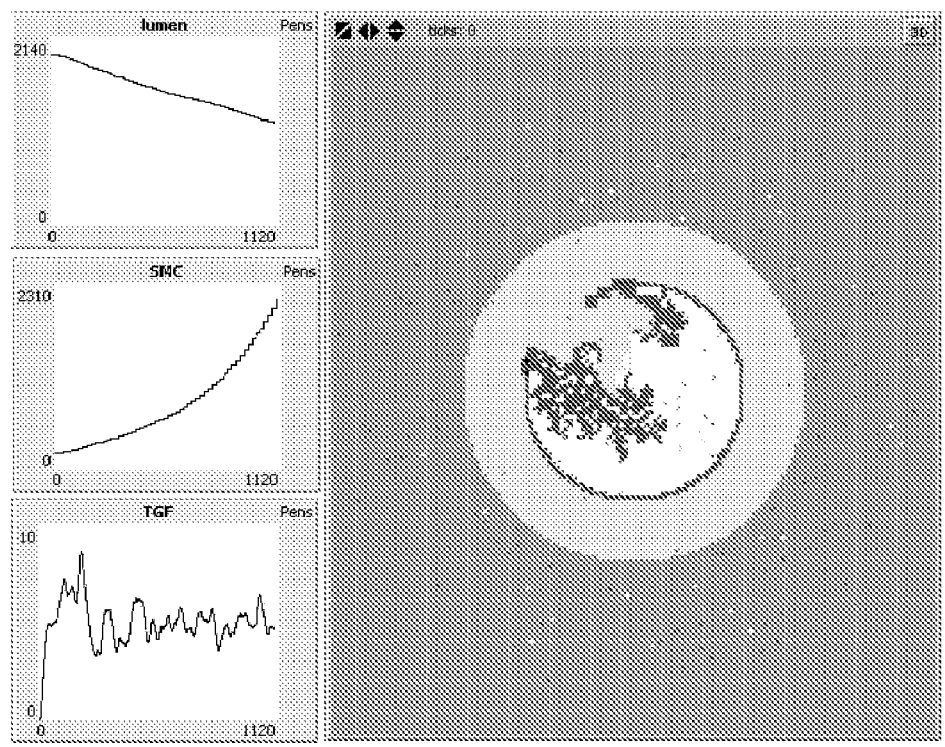
Figure 23N:
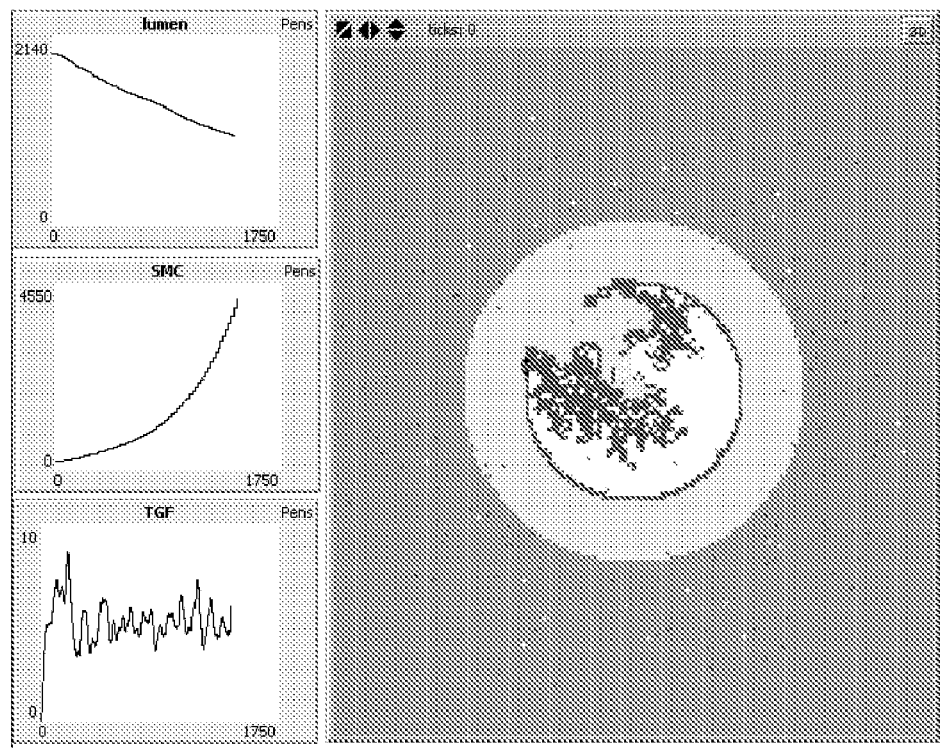
Figure 23O:
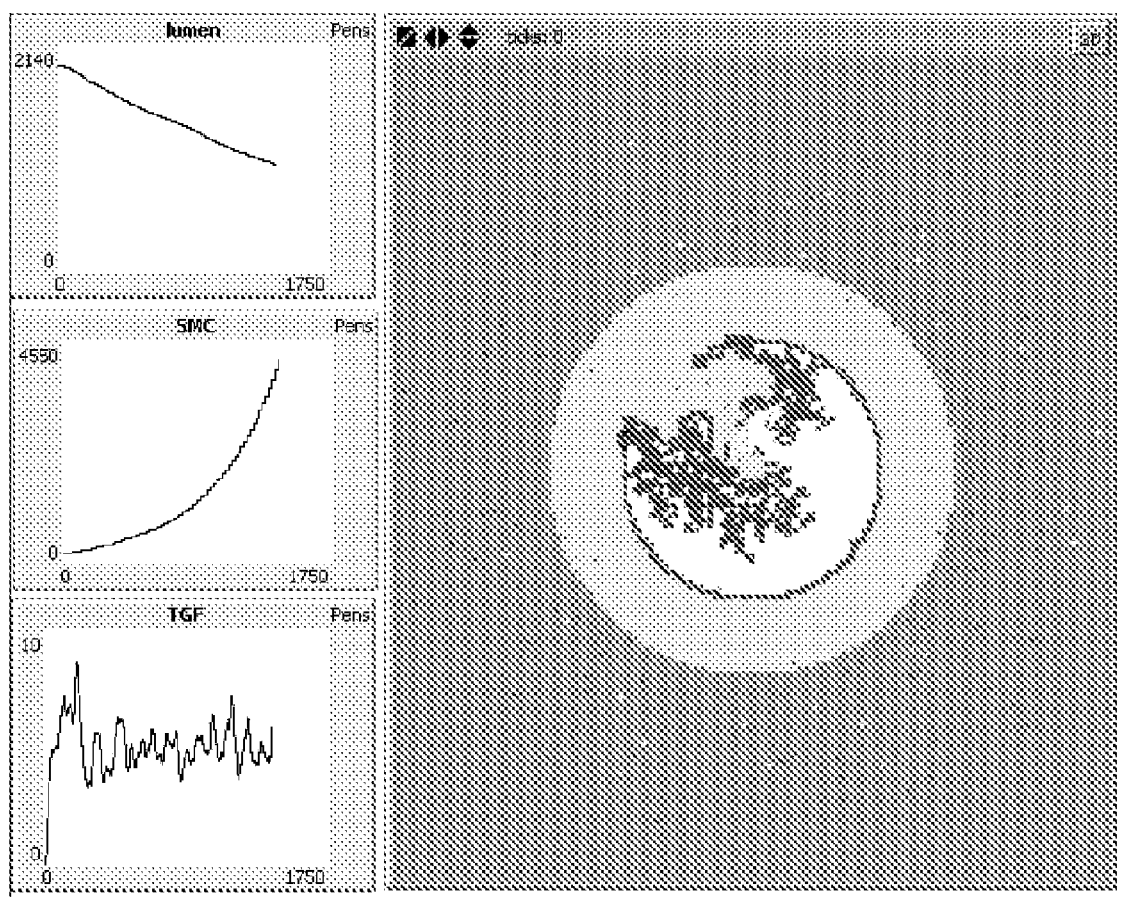

World: The model consists of 141×161=22701 patches. Initially, it has four compartments, as shown in FIG. 23A: lumen (white area, radius from 0 units to 25 units), endothelial cell layer (dary gray area, radius from 25 units-26 units), media (smooth muscle cell layer; light gray area, radius from 26 units-40 units), and adventitia (medium gray area, elsewhere).

Time scale: It is assumed in the model that 100 steps in the simulation represent approximately 1 day.

TGF-β1: 1. Produced by activated platelet. The dynamics are calculated by the equation: TGF=TGF+2; 2. TGF-β1 diffuses in the following sense: periodically (every 0.1 s) each patch shares 100 percent of the value of the patch with its 8 neighboring patches.

Platelets: Initially, there are 160 resting platelets randomly distributed in the lumen and they can not move through the endothelial layer. The life spans of the platelets are randomly chosen between 180 time steps and 200 steps (~1.8-2 days). Source: every 20 steps, 15 resting platelets are created in the lumen. Activation: when they migrate to the injury sites, they are activated. Chemoattraction: A platelet is chemoattracted by TGF-β1. Death rate: in every step, if platelet-age>0, then platelet-age=platelet-age-1, else die.

Activated platelets: 1. Activated platelets ("aplatelet") produce TGF-β1. Once the platelets are activated, they adhere to each other at the injury site(s), thereby eventually forming a thrombus. The life spans of the platelets are randomly distributed between 15 and 25 time steps (~0.15-0.25 days). Death rate: in every step, if aplatelet-age>0, then aplatelet-age=aplatelet-age−1, else die.

Smooth muscle cells: Initially, there are 200 smooth muscle cells randomly distributed in the yellow area. They are chemoattracted by TGF-β1. They can migrate into the lumen only through the injury sites. They move randomly every 20 steps. Proliferation: every 20 steps, the smooth muscle cells in the area (radius 26 units-40 units) has a 5 percent probability to hatch a new smooth muscle cell (i.e to proliferate).

Endothelial cells: Every 60 steps, the endothelial cells that are at the periphery of the wound will migrate to the wound edge to close the wound.

Macrophage: Initially, there are 80 macrophages randomly distributed in the adventitia. They move randomly in the adventitia.

Neutrophil: Initially, there are 80 neutrophils randomly distributed in the adventitia. 2. They move randomly in the adventitia.

Fibroblast: Initially, there are 30 fibroblasts randomly distributed in the adventitia. They move randomly in the adventitia.

We claim:

1. A method of simulating tissue healing, comprising using a computer to model the interrelated effects of inflammation, tissue damage or dysfunction and tissue healing to predict an outcome of healing of damaged tissue in silico, the model comprising an agent-based model comprising a pro-inflammatory agent, a tissue damage component and a feed-forward loop of inflammation to damage to inflammation regulated by one or more anti-inflammatory agents, thereby predicting the outcome of healing of damaged tissue in vivo.

2. The method of claim 1, in which an agent-based model is used to simulate one or more elements of inflammation, tissue damage or dysfunction and tissue healing.

3. The method of claim 1, wherein the agent-based model comprises
   a representation of a tissue;
   an initiating event that induces both inflammation and anti-inflammation activities in the tissue;
   an inflammatory component that produces tissue damage and anti-inflammatory activity;
   an anti-inflammatory component that suppresses inflammatory activity, suppresses tissue damage and promotes tissue healing; and
   a tissue damage component comprising an alarm/danger signal that is caused by inflammation and which causes additional inflammation in a feed-forward loop of inflammation to tissue damage to inflammation.

4. The method of claim 1, wherein the model comprises an anti-inflammatory agent as an element.

5. The method of claim 4, wherein the anti-inflammatory agent is one of active TGF-β1, latent TGF-β1 and IL-10.

6. The method of claim 1, wherein the model comprises a pro-inflammatory agent as an element.

7. The method of claim 1, wherein the computer-based model is developed using an agent-based modeling software platform.

8. The method of claim 1, wherein one or more of: active TGF-β1; latent TGF-β1; a TGF-β1 binding protein; IL-1β; TNF; TGF; IL-6; IL-8; IL-12; IFN-γ; VEGF; IL-10; TGF α; EGF; IGF-1; basic FGF; acidic FGF; a prostaglandin, PGE2, a matrix metalloproteinase; MMP-2, MMP-8, MMP-9 and their precursors; a pro-inflammatory factor; an anti-inflammatory factor; tissue inhibitor of a metalloproteinases; TIMP-1; TIMP-2; HMGB1; RAGE; an alarm/danger signal; urate crystals; a biological correlate of tissue damage; heat shock protein 70; extracellular matrix fragments; hyaluronic acid; advanced glycation endproducts; a soluble receptor for a biological agent; platelets; macrophages; neutrophils; B-cells; T-cells; dendritic cells; fibroblasts; keratinocytes; endothelial cells; smooth muscle cells; a microbe; and collagen is an element of the model.

9. The method of claim 1, wherein the model comprises a therapeutic or diagnostic agent as an element.

10. The method of claim 1, wherein the model simulates the impact of a therapeutic strategy for a disease or condition involving the interrelations among inflammation, tissue damage or dysfunction and tissue healing.

11. The method of claim 10, wherein the disease or condition is one of: diabetes, diabetic foot ulcers, necrotizing enterocolitis, ulcerative colitis, Crohn's disease, inflammatory bowel disease, restenosis (post-angioplasty or stent implantation), incisional wounding, excisional wounding, surgery, accidental trauma, pressure ulcer, stasis ulcer, tendon rupture, vocal fold phonotrauma, otitis media and pancreatitis.

12. The method of claim 1, further comprising using the model to rationally design a drug, device, diagnostic, prophylaxis or therapeutic strategy for a disease or condition involving the interrelations among inflammation, tissue damage or dysfunction and tissue healing.

13. The method of claim 12, wherein the disease or condition is one of: diabetes, diabetic foot ulcers, necrotizing enterocolitis, ulcerative colitis, Crohn's disease, inflammatory bowel disease, restenosis (post-angioplasty or stent implantation), incisional wounding, excisional wounding, surgery, accidental trauma, pressure ulcer, stasis ulcer, tendon rupture, vocal fold phonotrauma, otitis media and pancreatitis.

14. The method of claim 1, further comprising using the model in the diagnosis of a disease involving the interrelations among inflammation, tissue damage or dysfunction and tissue healing.

15. The method of claim 14, wherein the disease or condition is one of: diabetes, diabetic foot ulcers, necrotizing enterocolitis, ulcerative colitis, Crohn's disease, inflammatory bowel disease, restenosis (post-angioplasty or stent implantation), incisional wounding, excisional wounding, surgery, accidental trauma, pressure ulcer, stasis ulcer, tendon rupture, vocal fold phonotrauma, otitis media and pancreatitis.

16. The method of claim 1, wherein the tissue healing in one or more of: diabetes, diabetic foot ulcers, necrotizing enterocolitis, ulcerative colitis, Crohn's disease, inflammatory bowel disease, restenosis (post-angioplasty or stent implantation), incisional wounding, excisional wounding, surgery, accidental trauma, pressure ulcer, stasis ulcer, tendon rupture, vocal fold phonotrauma, otitis media and pancreatitis is simulated.

17. The method of claim 1, wherein the model simulates tissue healing in a diabetic foot ulcer.

18. The method of claim 17, wherein the model comprises TNF as a pro-inflammatory agent, TGF-$\beta$1 as an anti-inflammatory agent, and advanced glycation end products as alarm/danger signals (markers of tissue damage).

19. The method of claim 1, wherein the model simulates tissue healing in vocal folds.

20. The method of claim 19, wherein the model comprises IL-1$\beta$ and TNF as pro-inflammatory elements and IL-13 as an anti-inflammatory element.

21. The method of claim 1, wherein the model simulates tissue healing in necrotizing enterocolitis.

22. The method of claim 21, wherein the model comprises TNF as a pro-inflammatory element, IL-10 as an anti-inflammatory element, and HMGB1 as an alarm/danger signal (marker of tissue damage).

23. The method of claim 1, wherein the model simulates tissue healing in post-angioplasty or post-stenting restenosis.

24. The method of claim 23, wherein the model comprises TNF as a pro-inflammatory element, TGF-$\beta$1 as an anti-inflammatory element, and advanced glycation end products as alarm/danger signals.

25. The method of claim 1, wherein the model simulates tissue healing in an inflammatory bowel disease.

26. The method of claim 25, wherein the model comprises TNF as a pro-inflammatory element, TGF-$\beta$1 as an anti-inflammatory element, and HMGB1 as an alarm/danger signal.

27. The method of claim 25, wherein the inflammatory bowel disease is Crohn's disease or ulcerative colitis.

28. The method of claim 1, wherein the model simulates tissue healing in pancreatitis.

29. The method of claim 28, wherein the model comprises TNF as a pro-inflammatory element, IL-10 as an anti-inflammatory element, and hyaluronic acid as an alarm/danger signal.

30. The method of claim 1, wherein the model simulates tissue healing in external tissue trauma.

31. The method of claim 30, wherein the model comprises TNF as a pro-inflammatory element, IL-10 as an anti-inflammatory element, and HMGB1 as an alarm/danger signal.

32. The method of claim 1, wherein the model simulates healing of connective tissues of skin, mucosa, and other soft tissues.

33. The method of claim 32, wherein the model comprises TNF and IL-1$\beta$ as pro-inflammatory elements, PGE$_2$ as an anti-inflammatory element, and HMGB1 as an alarm/danger signal.

34. The method of claim 1, wherein the model simulates healing of connective tissues of skin, mucosa, and other soft tissues.

35. The method of claim 34, wherein the model comprises TNF and IL-1$\beta$ as pro-inflammatory elements, PGE$_2$ as an anti-inflammatory element, and HMGB1 as an alarm/danger signal.

36. A computing device comprising a processor and implementing a process implementing a computer model of the interrelated effects of inflammation, tissue damage or dysfunction and tissue healing to predict an outcome of healing of damaged tissue in silico, the model comprising an agent-based model comprising a pro-inflammatory agent, a tissue damage component and a feed-forward loop of inflammation to damage to inflammation regulated by one or more anti-inflammatory agents, thereby predicting the outcome of healing of damaged tissue in vivo.

37. The computing device of claim 36, in which an agent-based model is used to simulate one or more elements of inflammation, tissue damage or dysfunction and tissue healing.

38. The computing device of claim 36, wherein the agent-based model comprises:
a representation of a tissue;
an initiating event that induces both inflammation and anti-inflammation activities in the tissue;
an inflammatory component that produces tissue damage and anti-inflammatory activity;
an anti-inflammatory component that suppresses inflammatory activity, suppresses tissue damage and promotes tissue healing; and
a tissue damaage component comprising an alarm/danger signal that is caused by inflammation and which causes additional inflammation in a feed-forward loop of inflammation to tissue damage to inflammation.

39. The computing device of claim 36, wherein the model comprises an anti-inflammatory agent as an element.

40. The computing device of claim 39, wherein the anti-inflammatory agent is one of active TGF-$\beta$1, latent TGF-$\beta$1 and IL-10.

41. The computing device of claim 36, wherein the model comprises a pro-inflammatory agent as an element.

42. The computing device of claim 36, wherein the computer-based model is developed using an agent-based modeling software platform.

43. The computing device of claim 36, wherein one or more of: active TGF-$\beta$1; latent TGF-$\beta$1; a TGF-$\beta$1 binding protein; IL-1β; TNF; TGF; IL-6; IL-8; IL-12; IFN-γ; VEGF; IL-10; TGF α; EGF; IGF-1; basic FGF; acidic FGF; a matrix metalloproteinase; MMP-2, MMP-8, MMP-9 and their precursors; a pro-inflammatory factor; an anti-inflammatory factor; tissue inhibitor of a metalloproteinases; TIMP-1; TIMP-2; HMGB1; RAGE; an alarm/danger signal; urate crystals; a biological correlate of tissue damage; heat shock protein 70; extracellular matrix fragments; hyaluronic acid; advanced glycation endproducts; a soluble receptor for a biological agent; platelets; macrophages; neutrophils; B-cells; T-cells; dendritic cells; fibroblasts; keratinocytes; endothelial cells; smooth muscle cells; a microbe; and collagen is an element of the model.

44. The computing device of claim 36, wherein the model comprises a therapeutic or diagnostic agent as an element.

45. The computing device of claim 36, wherein the model simulates the impact of a therapeutic strategy for a disease or condition involving the interrelations among inflammation, tissue damage or dysfunction and tissue healing.

46. The computing device of claim 45, wherein the disease or condition is one of: diabetes, diabetic foot ulcers, necrotizing enterocolitis, ulcerative colitis, Crohn's disease, inflammatory bowel disease, restenosis (post-angioplasty or stent implantation), incisional wounding, excisional wounding, surgery, accidental trauma, pressure ulcer, stasis ulcer, tendon rupture, vocal fold phonotrauma, otitis media and pancreatitis.

47. The computing device of claim 36, further comprising using the model to rationally design a drug, device, diagnostic, prophylaxis or therapeutic strategy for a disease or condition involving the interrelations among inflammation, tissue damage or dysfunction and tissue healing.

48. The computing device of claim 47, wherein the disease or condition is one of: diabetes, diabetic foot ulcers, necrotizing enterocolitis, ulcerative colitis, Crohn's disease, inflammatory bowel disease, restenosis (post-angioplasty or stent implantation), incisional wounding, excisional wounding, surgery, accidental trauma, pressure ulcer, stasis ulcer, tendon rupture, vocal fold phonotrauma, otitis media and pancreatitis.

49. The computing device of claim 36, further comprising using the model in the diagnosis of a disease involving the interrelations among inflammation, tissue damage or dysfunction and tissue healing.

50. The computing device of claim 49, wherein the disease or condition is one of: diabetes, diabetic foot ulcers, necrotizing enterocolitis, ulcerative colitis, Crohn's disease, inflammatory bowel disease, restenosis (post-angioplasty or stent implantation), incisional wounding, excisional wounding, surgery, accidental trauma, pressure ulcer, stasis ulcer, tendon rupture, vocal fold phonotrauma, otitis media and pancreatitis.

51. The computing device of claim 36, wherein tissue healing in one or more of: diabetes, diabetic foot ulcers, necrotizing enterocolitis, ulcerative colitis, Crohn's disease, inflammatory bowel disease, restenosis (post-angioplasty or stent implantation), incisional wounding, excisional wounding, surgery, accidental trauma, pressure ulcer, stasis ulcer, tendon rupture, vocal fold phonotrauma, otitis media and pancreatitis is simulated.

52. The computing device of claim 36, wherein the model simulates tissue healing in a diabetic foot ulcer.

53. The computing device of claim 52, wherein the model comprises TNF as a pro-inflammatory agent, TGF-β1 as an anti-inflammatory agent, and advanced glycation end products as alarm/danger signals (markers of tissue damage).

54. The computing device of claim 36, wherein the model simulates tissue healing in vocal folds.

55. The computing device of claim 54, wherein the model comprises IL-1β and TNF as pro-inflammatory elements and IL-13 as an anti-inflammatory element.

56. The computing device of claim 36, wherein the model simulates tissue healing in necrotizing enterocolitis.

57. The computing device of claim 56, wherein the model comprises TNF as a pro-inflammatory element, IL-10 as an anti-inflammatory element, and HMGB1 as an alarm/danger signal (marker of tissue damage).

58. The computing device of claim 36, wherein the model simulates tissue healing in post-angioplasty or post-stenting restenosis.

59. The computing device of claim 58, wherein the model comprises TNF as a pro-inflammatory element, TGF-β1 as an anti-inflammatory element, and advanced glycation end products as alarm/danger signals.

60. The computing device of claim 36, wherein the model simulates tissue healing in an inflammatory bowel disease.

61. The computing device of claim 60, wherein the model comprises TNF as a pro-inflammatory element, TGF-β1 as an anti-inflammatory element, and HMGB1 as an alarm/danger signal.

62. The computing device of claim 60, wherein the inflammatory bowel disease is Crohn's disease or ulcerative colitis.

63. The computing device of claim 36, wherein the model simulates tissue healing in pancreatitis.

64. The computing device of claim 63, wherein the model comprises TNF as a pro-inflammatory element, IL-10 as an anti-inflammatory element, and hyaluronic acid as an alarm/danger signal.

65. The computing device of claim 36, wherein the model simulates tissue healing in external tissue trauma.

66. The computing device of claim 65, wherein the model comprises TNF as a pro-inflammatory element, IL-10 as an anti-inflammatory element, and HMGB1 as an alarm/danger signal.

67. The computing device of claim 36, wherein the model simulates healing of connective tissues of skin, mucosa, and other soft tissues.

68. The computing device of claim 67, wherein the model comprises TNF and IL-1β as pro-inflammatory elements, $PGE_2$ as an anti-inflammatory element, and HMGB1 as an alarm/danger signal.

69. The computing device of claim 36, wherein the model simulates healing of connective tissues of skin, mucosa, and other soft tissues.

70. The computing device of claim 69, wherein the model comprises TNF and IL-1β as pro-inflammatory elements, $PGE_2$ as an anti-inflammatory element, and HMGB1 as an alarm/danger signal.

* * * * *

UNITED STATES PATENT AND TRADEMARK OFFICE
CERTIFICATE OF CORRECTION

PATENT NO. : 8,165,819 B2
APPLICATION NO. : 11/869852
DATED : April 24, 2012
INVENTOR(S) : Gilles Clermont et al.

It is certified that error appears in the above-identified patent and that said Letters Patent is hereby corrected as shown below:

Column 62, Line 21, Claim 3, after "comprises" insert -- : --

Column 64, Line 52, Claim 38, delete "damaage :" and insert -- damage --

Signed and Sealed this
Eleventh Day of September, 2012

David J. Kappos
*Director of the United States Patent and Trademark Office*